United States Patent
Clogston

(10) Patent No.: US 9,012,605 B2
(45) Date of Patent: Apr. 21, 2015

(54) CRYSTALLINE POLYPEPTIDES

(75) Inventor: Christi L. Clogston, Camarillo, CA (US)

(73) Assignee: Amgen Inc., Thousand Oaks, CA (US)

( * ) Notice: Subject to any disclaimer, the term of this patent is extended or adjusted under 35 U.S.C. 154(b) by 1010 days.

(21) Appl. No.: 12/161,266

(22) PCT Filed: Jan. 22, 2007

(86) PCT No.: PCT/US2007/001786
§ 371 (c)(1),
(2), (4) Date: Oct. 2, 2008

(87) PCT Pub. No.: WO2007/102946
PCT Pub. Date: Sep. 13, 2007

(65) Prior Publication Data
US 2009/0221789 A1    Sep. 3, 2009

Related U.S. Application Data

(60) Provisional application No. 60/761,218, filed on Jan. 23, 2006.

(51) Int. Cl.
*C07K 14/00* (2006.01)
*A61K 9/00* (2006.01)
*A61K 9/28* (2006.01)

(52) U.S. Cl.
CPC ............. *A61K 9/0019* (2013.01); *A61K 9/2806* (2013.01)

(58) Field of Classification Search
None
See application file for complete search history.

(56) References Cited

U.S. PATENT DOCUMENTS

| | | |
|---|---|---|
| 3,691,016 A | 11/1972 | Patel et al. |
| 3,941,763 A | 3/1976 | Sarantakis |
| 3,969,287 A | 7/1976 | Jaworek et al. |
| 4,179,337 A | 12/1979 | Davis et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,289,872 A | 9/1981 | Denkewalter et al. |
| 4,301,144 A | 11/1981 | Iwashita et al. |
| 4,330,440 A | 5/1982 | Ayers et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 5,229,490 A | 7/1993 | Tam |
| 5,739,277 A | 4/1998 | Presta et al. |
| 5,869,451 A | 2/1999 | Dower et al. |
| 5,932,946 A | 8/1999 | Miyasaka et al. |
| 6,020,004 A | 2/2000 | Shah |
| 6,036,978 A | 3/2000 | Gombotz et al. |
| 6,083,534 A | 7/2000 | Wallach et al. |
| 6,245,740 B1 | 6/2001 | Goldenberg et al. |
| 6,432,449 B1 | 8/2002 | Goldenberg et al. |
| 6,451,346 B1 | 9/2002 | Shah et al. |
| 6,541,033 B1 | 4/2003 | Shah |
| 6,541,606 B2 | 4/2003 | Margolin et al. |
| 2002/0136719 A1 | 9/2002 | Shenoy et al. |

FOREIGN PATENT DOCUMENTS

| | | |
|---|---|---|
| WO | WO-93/21259 | 10/1993 |
| WO | WO-95/18858 | 7/1995 |
| WO | WO-95/21919 | 8/1995 |
| WO | WO-95/21920 | 8/1995 |
| WO | WO-95/24183 | 9/1995 |
| WO | WO-95/26746 | 10/1995 |
| WO | WO-96/32152 | 10/1996 |
| WO | WO-96/32478 | 10/1996 |
| WO | WO-97/34631 | 9/1997 |
| WO | WO-97/41833 | 11/1997 |
| WO | WO-00/24770 | 5/2000 |
| WO | WO-02/068455 | 9/2002 |
| WO | WO-2005/012353 | 2/2005 |

OTHER PUBLICATIONS

Drenth, "Principles of Protein X-Ray Crystallography", 2nd Edition, 1999 Springer-Verlag New York Inc., Chapter 1, p. 1-21.*
McPherson, A. Current Approaches to Macromolecular Crystallization. European Journal of Biochemistry. 1990. vol. 189, pp. 1-23.*
Cudney R. Protein Crystallization and Dumb Luck. The Rigaku Journal. 1999. vol. 16, No. 1, pp. 1-7.*
Akers, Excipient-drug interactions in parenteral formulations. *J. Pharm. Sci.* 91: 2283-300 (2002).
Bernstein et al., The Protein Data Bank: a computer-based archival file for macromolecular structures. *J. Mol. Biol.* 112: 535-42 (1977).
Bhatnagar et al., Structure-activity relationships of novel hematoregulatory peptides. *J. Med. Chem.* 39: 3814-19 (1996).
Bowie et al., A method to identify protein sequences that fold into a known three-dimensional structure. *Science* 253: 164-70 (1991).
Brenner et al., Population statistics of protein structures: Lessons from structural classifications. *Curr. Opin. Struct. Biol.* 7: 369-76 (1997).
Chou et al., Conformational parameters for amino acids in helical, beta-sheet, and random coil regions calculated from proteins. *Biochemistry* 13: 211-22 (1974).
Chou et al., Empirical predictions of protein conformation. *Annu. Rev. Biochem.* 47: 251-76 (1978).
Chou et al., Prediction of beta-turns. *Biophys. J.* 26: 367-84 (1979).
Chou et al., Prediction of protein conformation. *Biochemistry* 13: 222-45 (1974).
Cleland et al., The development of stable protein formulations: A close look at protein aggregation, deamidation, and oxidation. *Crit. Rev. Ther. Drug Carrier. Syst.* 10: 307-30 (1993).—Part 1.
Cleland et al., The development of stable protein formulations: A close look at protein aggregation, deamidation, and oxidation. *Crit. Rev. Ther. Drug Carrier. Syst.* 10: 331-53 (1993).—Part 2.

(Continued)

*Primary Examiner* — Suzanne M Noakes
(74) *Attorney, Agent, or Firm* — Timothy J. Gaul

(57) ABSTRACT

Crystalline formulations of therapeutic peptides, along with methods for making and using the same, are provided.

4 Claims, No Drawings

(56) References Cited

OTHER PUBLICATIONS

Cleland et al., The development of stable protein formulations: A close look at protein aggregation, deamidation, and oxidation. *Crit. Rev. Ther. Drug Carrier. Syst.* 10: 354-77 (1993).—Part 3.

Coligan (Ed.) et al., Current Protocols in Protein Science. John Wiley & Sons, Inc., pp. 17.4.1-17.4.25. (1995-2002).

Cwirla et al., Peptide agonist of the thrombopoietin receptor as potent as the natural cytokine. *Science* 276: 1696-99 (1997).

Ellison et al., The nucleotide sequence of a human immunoglobulin C gamma1 gene. *Nucl. Acids Res.* 10: 4071-79 (1982).

Gilliland et al., A biological macromolecule crystallization database: a basis for a crystallization strategy. *J. Cryst Growth* 90: 51-59 (1988).

Gribskov et al., Profile analysis. *Meth. Enzym.* 183: 146-59 (1990).

Gribskov et al., Profile analysis: detection of distantly related proteins. *Proc. Nat. Acad. Sci. USA* 84: 4355-58 (1987).

Gribskov et al., Sigma factors from *E. coli, B. subtilis,* phage SP01, and phage T4 are homologous proteins. *Nucl. Acids Res.* 14: 6745-63 (1986).

Guss et al., Structure of the IgG-binding regions of streptococcal protein G. *EMBO J.* 5: 1567-75 (1986).

Holm et al., Protein folds and families: Sequence and structure alignments. *Nucl. Acids Res.* 27: 244-7 (1999).

Jones, Progress in protein structure prediction. *Curr. Opin. Struct. Biol.* 7: 377-87 (1997).

Kyte et al., A simple method for displaying the hydropathic character of a protein. *J. Mol. Biol.* 157: 105-31 (1982).

Lindmark et al., Binding of immunoglobulins to protein A and immunoglobulin levels in mammalian sera. *J. Immunol. Meth.* 62: 1-13 (1983).

MacLennan et al., Structure-function relationships in the Ca(2+)-binding and translocation domain of SERCA1: physiological correlates in Brody disease. *Acta. Physiol. Scand.* Suppl. 643: 55-67 (1998).

McPherson, Crystallization of macromolecules: General principles. *Meth. Enzymol.* 114: 112-20 (1985).

Miller et al., Reporting results of cancer treatment. *Cancer* 47: 210-11 (1981).

Moult, The current state of the art in protein structure prediction. *Curr. Opin. Biotechnol.* 7: 422-27 (1996).

Robbins et al., Antibodies to covalent aggregates of insulin in blood of insulin-using diabetic patients. *Diabetes* 36: 838-45 (1987).

Sarmay et al., Mapping and comparison of the interaction sites on the Fc region of IgG responsible for triggering antibody dependent cellular cytotoxicity (ADCC) through different types of human Fc gamma receptor. *Molec. Immunol.* 29: 633-39 (1992).

Sasaki et al., Structure-mutation analysis of the ATPase site of *Dictyostelium* discoideum myosin II. *Adv. Biophys.* 35:1-24 (1998).

Sippl et al., Threading thrills and threats. *Structure* 4: 15-19 (1996).

Wootton et al., Analysis of compositionally biased regions in sequence databases. *Meth. Enzymol.* 266: 554-71 (1996).

\* cited by examiner

CRYSTALLINE POLYPEPTIDES

BACKGROUND OF THE INVENTION

Many therapeutic molecules are polypeptides, some of which are prone to denaturation, degradation, and/or aggregation. Aggregation of polypeptides is undesirable as it may result in immunogenicity (Cleland et al., 1993, Crit. Rev Therapeutic Drug Carrier Systems, 10: 307-377; and Robbins et al., 1987, Diabetes, 36: 838-845). Polypeptides are also subject to catalysis or conversion into inactive forms by the natural biological processes of the organisms to which they are administered. Further, therapeutic polypeptides may be produced as a heterogeneous mixture of forms, varying in the extent of glycosylation or in other aspects of their three-dimensional conformation.

Crystallization of therapeutic polypeptides provides an advantage in producing a stable and homogenous formulation of such polypeptides. Certain advantages of crystals include greater ease of handling of the therapeutic compound in preparing pharmaceutical products; reduced degradation, denaturation and/or aggregation; the potential for creating a sustained release form of the therapeutic polypeptide to reduce the frequency of dosing; and the ability to use crystalline therapeutic polypeptides to form a pharmaceutical composition having a very high concentration of the therapeutic polypeptide. In addition, crystallization methods can produce a more homogenous population of polypeptides in the formulation, because only the addition of similarly configured polypeptide molecules will add to sustained growth of the crystal—when a limiting amount of polypeptides of variant structure have been incorporated into the crystal lattice, the resulting structural weaknesses in the crystal will prevent its further growth. Since incorporation into a crystalline form can ensure that a greater percentage of the polypeptides will be in an active form, administration of a smaller amount of the crystalline therapeutic peptides can produce a therapeutic effect equivalent to administration of a greater amount of a more heterogeneous polypeptide formulation.

Therefore, there is a need for crystalline formulations of therapeutic polypeptides.

SUMMARY OF THE INVENTION

For purposes of describing the invention, peptide sequences are set out either in one-letter or three-letter designations well known and understood in the art.

The present invention provides crystalline compounds that are capable of binding to and triggering a transmembrane signal through, i.e., activating, a c-Mpl receptor, the same receptor that mediates the activity of endogenous thrombopoietin (TPO). Thus, the compounds have thrombopoietic activity, i.e., the ability to stimulate, in vivo and in vitro, the production of platelets, and/or megakaryocytopoietic activity, i.e., the ability to stimulate, in vivo and in vitro, the production of platelet precursors.

In one embodiment, a crystalline compound that binds a c-Mpl receptor is provided that comprises the following general structure:

TMP1-(L1)n-TMP2 wherein TMP1 and TMP2 are each independently selected from the group of peptides comprising a core structure as set out herein;
L1 is a linker as described herein;
and n is 0 or 1;
and physiologically acceptable salts thereof.

In another embodiment, the crystalline compounds that bind a c-Mpl receptor comprise the general formula:

(V1)m-(L2)q-TMP1-(L1)n-TMP2-(L3)r-(V2)p wherein TMP1 and TMP2 are each independently selected from the group of peptides comprising a core structure as set out herein;
n is 1 or 0;
L1, L2 and L3 are linker groups which are each independently selected from the linker groups described herein;
V1 and V2 are each independently a vehicle as defined herein; m, p, q and r are each independently selected from the group consisting of 0 and 1, wherein at least one of m or p is 1, and further wherein if m is 0 then q is 0, and if p is 0, then r is 0;
and physiologically acceptable salts thereof.

In another aspect, the crystalline compound that binds to a c-Mpl receptor comprises the formula:

(L1)l-(TMP1)a-(L2)m-(TMP2)b-(L3)n-(TMP3)c-(L4)o-(TMP4)d-(L5)p wherein TMP1, TMP2, TMP3, and TMP4 are each independently selected from the group of peptides comprising a core structure as set out herein;
L1, L2, L3, L4 and L5 are each independently a linker as described herein;
a, b, c and d are each independently selected from the group consisting of 0 and 1;
l, m, n, o, and p are each independently selected from the group consisting of 0 and 1;
and physiologically acceptable salts thereof.

In yet another aspect, a crystalline compound is provided that binds to a c-Mpl receptor comprising the formula:

(V1)v-(L1)l-(TMP1)a-(L2)m-(TMP2)b-(L3)n-(TMP3)c-(L4)o-(TMP4)d-(L4)p-(V2)w wherein TMP1, TMP2, TMP3, and TMP4 are each independently selected from the group of peptides comprising a core structure as set out herein;
L1, L2, L3, L4 and L5 are each independently a linker as described herein;
a, b, c and d are each independently selected from the group consisting of 0 and 1;
l, m, n, o, and p are each independently selected from the group consisting of 0 and 1;
V1 and V2 are each independently a vehicle as described herein;
v and w are each independently an integer from 0 to 1 wherein at least one of v and w is 1, and further wherein when v is 0, l is 0 and when w is 0, p is 0; and physiologically acceptable salts thereof.

In one embodiment, the TMP core structure comprises the sequence:

(SEQ ID NO: 113)
X2-X3-X4-X5-X6-X7-X8-X9-X10 wherein,
X2 is selected from the group consisting of Glu, Asp, Lys, and Val;
X3 is selected from the group consisting of Gly and Ala;
X4 is Pro;
X5 is selected from the group consisting of Thr and Ser;
X6 is selected from the group consisting of Leu, Ile, Val, Ala, and Phe;

X7 is selected from the group consisting of Arg and Lys;

X8 is selected from the group consisting of Gln, Asn, and Glu;

X9 is selected from the group consisting of Trp, Tyr, Phe, Cys, and Ala;

X10 is selected from the group consisting of Leu, Ile, Val, Ala, Phe, Met, and Lys;

In addition to the core structure X2-X10 set forth above for any TMP, other related structures are also possible wherein one or more of the following is added to the TMP core structure: X1 is attached to the N-terminus and/or X11, X12, X13, and/or X14 are attached to the C-terminus, wherein X1, X12, X13, and X14 are as follows:

X1 is selected from the group consisting of Ile, Ala, Val, Leu, Ser, and Arg;

X11 is selected from the group consisting of Ala, Ile, Val, Leu, Phe, Ser, Thr, Lys, His, and Glu;

X12 is selected from the group consisting of Ala, Ile, Val, Leu, Phe, Gly, Ser, and Gln;

X13 is selected from the group consisting of Arg, Lys, Thr, Val, Asn, Gln, and Gly; and X14 is selected from the group consisting of Ala, Ile, Val, Leu, Phe, Thr, Arg, Glu, and Gly.

In another aspect, the TMP core structure comprises the sequence:

```
X1-X2-X3-X4-G-P-T-L-X9-X10-W-L-X13-X14-X15-X16-

X17-X18 (SEQ ID NO: 111)
``` wherein X1-X4, X9-X10, and X13-X18 are each independently an amino acid.

In one aspect, this core sequence is defined wherein:

X1 is selected from the group consisting of Ala, Val, Trp, Met, Gly, Tyr, Cys, Gln, Glu, Arg, and His;

X2 is selected from the group consisting of Ala, Val, Leu, Ile, Gly, Ser, and Cys;

X3 is selected from the group consisting of Leu, Ile, Pro, Trp, Gly, Ser, Asp, Lys, and Arg;

X4 is selected from the group consisting of Leu, Gly, Gln, Asp, Glu, and His;

X9 is selected from the group consisting of Lys and Arg;

X10 is selected from the group consisting of Gln and Glu;

X13 is selected from the group consisting of Ala, Val, Leu, Ser, Gln, Glu, and Arg;

X14 is selected from the group consisting of Ala, Trp, Thr, Tyr, Cys, and Gln;

X15 is selected from the group consisting of Val, Leu, Gly, Tyr, and Arg;

X16 is selected from the group consisting of Ala, Leu, Phe, Gly, and Arg;

X17 is selected from the group consisting of Ala, Val, Leu, Met, Gly, Cys, Gln, and Asn; and X18 is selected from the group consisting of Ala, Val, Pro, Met, Phe, Gly, Cys, Gln, and Lys.

In yet another aspect, the TMP core structure comprises the sequence:

```
                                        (SEQ ID NO: 112)
    X1-X2-R-E-G-P-T-L-R-Q-W-L-X13-W-R-R-X17-X18
``` wherein X1, X2, X13, X17 and X18 are each independently an amino acid.

In one aspect, this core structure is defined wherein:

X1 is selected from the group consisting of Ala, Val, Trp, Met, Gly, Tyr, Cys, Gln, Glu, Arg, and His;

X2 is selected from the group consisting of Ala, Val, Leu, Ile, Gly, Ser, and Cys;

X13 is selected from the group consisting of Ala, Val, Leu, Ser, Gln, Glu, and Arg;

X17 is selected from the group consisting of Ala, Val, Leu, Met, Gly, Cys, Gln, and Asn; and X18 is selected from the group consisting of Ala, Val, Pro, Met, Phe, Gly, Cys, Gln, and Lys.

In yet another aspect, a crystalline compound is provided that binds to a c-Mpl receptor comprising a sequence selected from the group consisting of SEQ ID NO: 6 to SEQ ID NO: 109, inclusive.

In another aspect, the crystalline compound is a dimer or multimer of a compound that binds a c-Mpl receptor comprising a sequence selected from the group consisting of SEQ ID NO: 6 to SEQ ID NO: 109.

Crystalline compounds are also provided which comprise a precipitant salt.

The compounds which are crystallized are prepared by standard synthetic methods, recombinant DNA techniques, or any other methods of preparing peptides and fusion proteins. Crystalline compounds that encompass non-peptide portions are synthesized by standard organic chemistry reactions, in addition to standard peptide chemistry reactions when applicable.

The crystalline compounds are used for therapeutic or prophylactic purposes by formulating them with appropriate pharmaceutical carrier materials and administering an effective amount to a patient, such as a human (or other mammal) in need thereof. The vehicle-linked crystalline compounds, in one aspect, have activity comparable to, or even greater than, naturally-occurring thrombopoietin.

In another aspect, methods of treating thrombocytopenic disorders are provided. In other aspects, the invention provides methods of increasing megakaryocytes or platelets and methods of producing compounds described herein.

In yet another aspect, pharmaceutical compositions are provided comprising a crystalline compound as described herein. The invention further contemplates use of a crystalline compound as described herein in the production of a medicament for the treatment of any condition as described herein.

In other aspects, polynucleotides are provided encoding the compounds disclosed herein, expression vectors comprising the polynucleotides and host cells comprising the expression vectors.

Derivatives of the crystalline compounds are also encompassed by this invention.

DETAILED DESCRIPTION OF THE PREFERRED EMBODIMENTS

Definition of Terms

The terms used throughout this specification are defined as follows, unless otherwise limited in specific instances.

The term "peptide" refers to molecules of 2 to 40 amino acids, molecules of 3 to 20 amino acids, and those of 6 to 15 amino acids. For example, peptides having a size selected from no greater than 35, no greater than 30, no greater than 25, no greater than 20 amino acids and/or no greater than 15 amino acids, are contemplated herein. Exemplary peptides may be randomly generated by any of the methods cited described herein, carried in a peptide library (e.g., a phage display library), derived by digestion of proteins, or chemically synthesized. Peptides include D and L form, either purified or in a mixture of the two forms.

The term "pharmacologically active" means that a substance so described is determined to have activity that affects a medical parameter (e.g., blood pressure, blood cell count, cholesterol level) or disease state (e.g., cancer, autoimmune disorders). Thus, pharmacologically active peptides comprise agonistic or mimetic and antagonistic peptides as defined below.

The term "thrombopoietin mimetic peptide," "TPO mimetic peptide" or "TMP" refers to a peptide that binds to the mpl receptor and/or has thrombopoietic activity, i.e., the ability to stimulate, in vivo or in vitro, the production of platelets or platelet precursors, including but not limited to megakaryocytes. Peptides of this type can be identified or derived as described in Cwirla et al. (1997), Science 276: 1696-9, U.S. Pat. Nos. 5,869,451 and 5,932,946, as well as International application WO 00/24770 published May 4, 2000, hereby incorporated by reference. Those of ordinary skill in the art appreciate that each of these references enables one to select different peptides than actually disclosed therein by following the disclosed procedures with different peptide libraries.

The term "c-Mpl-binding domain" refers to any amino acid sequence that binds the mpl receptor and comprises naturally occurring sequences or randomized sequences. Exemplary c-Mpl-binding domains can be identified or derived by phage display or other methods mentioned herein.

The term "c-Mpl receptor agonist" refers to a molecule that binds to the mpl receptor and increases or decreases one or more assay parameters as does endogenous thrombopoietin (eTPO), the native mpl receptor ligand.

The term "randomized" used in connection with peptide sequences refers to fully random sequences (e.g., selected by phage display methods or RNA-peptide screening) and sequences in which one or more residues of a naturally occurring molecule is replaced by an amino acid residue not present in that position in the naturally occurring molecule. Exemplary methods for creating and identifying randomized peptide sequences include phage display, *E. coli* display, ribosome display, RNA-peptide screening, chemical screening, and the like.

The term "dimer" as applied to peptides refers to molecules having two peptide chains associated covalently or non-covalently, with or without linkers. Peptide dimers wherein the peptides are linked C-terminus to N-terminus may also be referred to as "tandem repeats" or "tandem dimers." Peptide dimers wherein the peptides are linked C- to C-terminus, or N- to N-terminus may also be referred to as "parallel repeats" or "parallel dimers."

The term "multimer" as applied to Fc domains or molecules comprising Fc domains refers to molecules having two or more polypeptide chains associated covalently, noncovalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing (as defined herein) such a native Fc.

The terms "derivatizing" and "derivative" or "derivatized" involve processes and resulting compounds in which (1) the compound has a cyclic portion; for example, cross-linking between cysteinyl residues within the compound; (2) the compound is cross-linked or has a cross-linking site; for example, the compound has a cysteinyl residue and thus forms cross-linked dimers in culture or in vivo; (3) one or more peptidyl linkage is replaced by a non-peptidyl linkage; (4) the N-terminus is replaced by —$NRR^1$, $NRC(O)R^1$, —$NRC(O)OR^1$, —$NRS(O)_2R^1$, —NHC(O)NHR, a succinimide group, or substituted or unsubstituted benzyloxycarbonyl-NH— wherein R and $R^1$ and the ring substituents are as defined hereinafter; (5) the C-terminus is replaced by —C(O)$R^2$ or —$NR^3R^4$ wherein $R^2$, $R^3$ and $R^4$ are as defined hereinafter; and (6) compounds in which individual amino acid moieties are modified through treatment with agents capable of reacting with selected side chains or terminal residues. Derivatives are further described hereinafter.

"Bioefficacy" refers to the capacity to produce a desired biological effect. Bioefficacy of different compounds, or different dosages of the same compound, or different administrations of the same compound are generally normalized to the amount of compound(s) to permit appropriate comparison.

"Multidose administration" refers to a therapeutic or prophylactic treatment regimen which includes administration of more than one amount of a compound over a period of time.

"Comprising" means, inter alia and as defined herein, that a compound may include additional amino acids on either or both of the N- or C-termini of the given core structure sequence. However, as long as a core structure is present, the remaining chemical structure is relatively less important. Of course, any structure outside of the core structure should not significantly interfere with thrombopoietic activity of the compound. For example, an N-terminal Met residue is envisioned as falling within this invention.

Additionally, physiologically acceptable salts of the compounds of this invention are also encompassed herein. The term "physiologically acceptable salts" refers to any salts that are known or later discovered to be pharmaceutically acceptable. Some specific examples are: acetate; trifluoroacetate; hydrohalides, such as hydrochloride and hydrobromide; sulfate; citrate; tartrate; glycolate; and oxalate.

The term "vehicle" refers to a molecule that prevents degradation and/or increases half-life, reduces toxicity, reduces immunogenicity and/or increases biological activity of a therapeutic protein. Exemplary vehicles include an Fc domain (which is preferred) as well as a linear polymer (e.g., polyethylene glycol (PEG), polylysine, dextran, etc.); a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group (such as a steroid); a carbohydrate or oligosaccharide (e.g., dextran); any natural or synthetic protein, polypeptide or peptide that binds to a salvage receptor; albumin, including human serum albumin (HSA), leucine zipper domain, and other such proteins and protein fragments.

The term "native Fc" refers to molecule or sequence comprising the sequence of a non-antigen-binding fragment resulting from digestion of whole antibody, whether in monomeric or multimeric form. The original immunoglobulin source of the native Fc is preferably of human origin and may be any of the immunoglobulins, although IgG1 and IgG2 are preferred. Native Fcs are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms.

The term "Fc variant" refers to a molecule or sequence that is modified from a native Fc but still comprises a binding site for the salvage receptor, FcRn. International applications WO 97/34631 (published 25 Sep. 1997) and WO 96/32478 describe exemplary Fc variants, as well as interaction with the salvage receptor, and are hereby incorporated by reference in their entirety. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

The term "Fc domain" encompasses native Fc and Fc variant molecules and sequences as defined above. As with Fc variants and native Fcs, the term "Fc domain" includes molecules in monomeric or multimeric form, whether digested from whole antibody or produced by other means. In one embodiment, for example, the Fc region can be:

```
                                              (SEQ ID NO: 1)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

The terms "peptibody" and "peptibodies" refer to molecules comprising an antibody Fc domain attached to at least one peptide. Such peptibodies may be multimers or dimers or fragments thereof, and they may be derivatized.

"Isolated" as used herein refers to a polypeptide or other molecule that has been removed from the environment in which it naturally occurs.

"Substantially purified" as used herein refers to a polypeptide that is substantially free of other polypeptides present in the environment in which it naturally occurs or in which it was produced; a preparation of a polypeptide that has been substantially purified contains at least 90% by weight (or at least 95. %, at least 98%, or at least 99% by weight) of that polypeptide, wherein the weight of the polypeptide includes any carbohydrate, lipid, or other residues covalently attached to the polypeptide. A substantially purified polypeptide preparation may contain variation among polypeptide molecules within the preparation, with respect to extent and type of glycosylation or other post-translation modification, or with respect to conformation or extent of multimerization.

"Purified peptide" as used herein refers to an essentially homogenous peptide preparation; however, an essentially homogenous peptide preparation may contain variation among polypeptide molecules within the preparation, with respect to extent and type of glycosylation or other post-translation modification, or with respect to conformation or extent of multimerization.

The "percent identity" of two amino sequences can be determined by visual inspection and mathematical calculation, and the comparison can also be done by comparing sequence information using a computer program. The first step in determining percent identity is aligning the amino acid sequences to so as to maximize overlap and identities, while minimizing gaps in the alignment. The second step in determining percent identity is calculation of the number of identities between the aligned sequences, divided by the total number of amino acids in the alignment. When determining the percent identity that an amino acid sequence has "across the length of" a target amino acid sequence, the length of the target amino acid sequence is the minimum value for the number of total bases in the alignment. For example, when determining the percent identity of a first amino acid sequence of 50 amino acids "across the length of" a second amino acid sequence of amino acids 1 through 100 of hypothetical SEQ ID NO:X, if the first amino acid sequence is identical to amino acids 1 through 50 of hypothetical SEQ ID NO:X, the percent identity would be 50%. 50 amino acid identities divided by the total length of the alignment (100 amino acids). An exemplary computer program for aligning amino acid sequences and computing percent identity is the BLASTP program available for use via the National Library of Medicine website ncbi.nlm.nih.gov/gorf/wblast2.cgi, or the UW-BLAST 2.0 algorithm. Standard default parameter settings for UW-BLAST 2.0 are described at the following Internet site: sapiens.wustl.edu/blast/blast/README.html. In addition, the BLAST algorithm uses the BLOSUM62 amino acid scoring matrix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, Analysis of compositionally biased regions in sequence databases, *Methods Enzymol.* 266: 554-71) or segments consisting of short-periodicity internal repeats (as determined by the XNU program of Claverie and States (Computers and Chemistry, 1993)), and (B) a statistical significance threshold for reporting matches against database sequences, or E-score (the expected probability of matches being found merely by chance, according to the stochastic model of Karlin and Altschul (1990); if the statistical significance ascribed to a match is greater than this E-score threshold, the match will not be reported.); E-score threshold values are 0.5, 0.25, 0.1, 0.05, 0.01, 0.001, 0.0001, 1e–5, 1e–10, 1e–15, 1e–20, 1e–25, 1e–30, 1e–40, 1e–50, 1e–75, or 1e–100. Other programs used by those skilled in the art of sequence comparison can also be used to align amino acid sequences, such as, the Genetics Computer Group (GCG; Madison, Wis.) Wisconsin package version 10.0 program, 'GAP' (Devereux et al., 1984, *Nucl. Acids Res.* 12: 387). The default parameters for the 'GAP' program include: (1) The GCG implementation of a unary comparison matrix (containing a value of 1 for identities and 0 for non-identities) for nucleotides, and the weighted amino acid comparison matrix of Gribskov and Burgess, *Nucl. Acids Res.* 14:6745, 1986, as described by Schwartz and Dayhoff, eds., *Atlas of Polypeptide Sequence and Structure*, National Biomedical Research Foundation, pp. 353-358, 1979; or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps.

"An isolated peptide consisting essentially of an amino acid sequence" means that the polypeptide can optionally have, in addition to said amino acid sequence, additional material covalently linked to either or both ends of the polypeptide, said additional material between 1 and 10,000 additional amino acids covalently linked to either or both ends of the polypeptide; or between 1 and 1,000 additional amino acids covalently linked to either or both ends of the polypeptide; or between 1 and 100 additional amino acids covalently linked to either or both ends of the polypeptide. Covalent linkage of additional amino acids to either or both ends of the polypeptide according to the invention results in a combined amino acid sequence that is not naturally occurring.

"Mother liquor" as used herein means the buffer used for crystallization of a desired compound.

Compounds and Derivatives

Crystalline compounds are provided which bind a c-Mpl receptor and mimic the biological activity of thrombopoietin. These pharmacologically active crystalline compounds therefore posses an c-Mpl-binding domain and are c-Mpl receptor agonists. These TPO mimetics comprise peptides which bear no significant amino acid sequence homology with thrombopoietin yet stimulate thrombopoietin biological effects in most instances to an equal or greater degree than thrombopoietin.

In one embodiment, the crystalline compounds comprise the following general structure:

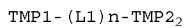

TMP1-(L1)n-TMP2₂ wherein TMP1 and TMP2 are each independently selected from the group of compounds comprising a core structure as defined herein;

L1 is a linker as described herein; and n is 0 or 1; and physiologically acceptable salts thereof.

Although many of the crystalline compounds of the invention are tandem dimers in that they possess two TMP moieties, other crystalline compounds of the invention are tandem multimers of the TMPs, i.e., crystalline compounds of the following exemplary structures:

TMP1-(L1)n-TMP2-(L2)o-TMP3;

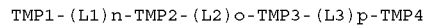

TMP1-(L1)n-TMP2-(L2)o-TMP3-(L3)p-TMP4

TMP1-(L1)n-TMP2-(L2)o-TMP3-(L3)p-TMP4-(L4)q-TMP5;

wherein TMP1, TMP2, TMP3, TMP4, and TMP5 have the same or different core structures, and wherein the core structure of each TMP is independently selected from the group of core structures as defined herein; and L1, L2, L3, and L4 are linkers as defined herein and are each optional, i.e., n, o, p, q are each independently 0 or 1; and physiological salts thereof.

The crystalline compounds in various embodiments have less than about 60, or less than about 40 amino acids in total (i.e., they will be peptides).

In another embodiment, the crystalline compounds are covalently attached to one or more vehicles, either directly or through linker groups. In general, the formula of this group of crystalline compounds is:

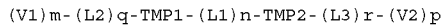

(V1)m-(L2)q-TMP1-(L1)n-TMP2-(L3)r-(V2)p wherein TMP1 and TMP2 each independently comprise a core structure as set out herein;

n is 0 or 1;

L1, L2 and L3 are linkers which are each independently selected from the linker groups described herein;

V1 and V2 are vehicles are described herein;

m, p, q and r are each independently selected from the group consisting of 0 and 1, wherein at least one of m or p is 1, and further wherein if m is 0 then q is 0, and if p is 0, then r is 0; and physiologically acceptable salts thereof.

Additionally, although many crystalline compounds of this embodiment include one or more tandem dimers in that they possess two linked TMP moieties, other crystalline compounds include tandem multimers of the TMPs, i.e., compounds of the following exemplary structures:

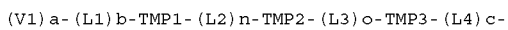

(V1)a-(L1)b-TMP1-(L2)n-TMP2-(L3)o-TMP3-(L4)c-

(V2)d;

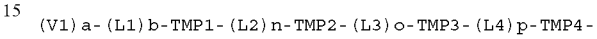

(V1)a-(L1)b-TMP1-(L2)n-TMP2-(L3)o-TMP3-(L4)p-TMP4-

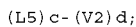

(L5)c-(V2)d;

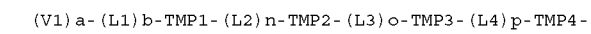

(V1)a-(L1)b-TMP1-(L2)n-TMP2-(L3)o-TMP3-(L4)p-TMP4-

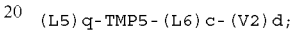

(L5)q-TMP5-(L6)c-(V2)d;

wherein TMP1, TMP2, TMP3, TMP4, and TMP5 each independently comprises a core structure as set out herein;

L1, L2, L3, L4, L5, and L6 are linkers which are optional, i.e., b, c, n, o, p, and q are 0 or 1, and wherein if a is 0, then b is 0 and if d is 0, then c is 0, V1 and V2 are vehicles as defined herein; and physiological salts thereof.

In one aspect, which is discussed in detail herein, V1 and/or V2 is an Fc domain. In this aspect, the Fc domain is monomeric or dimeric, and in cases where the Fc is dimeric, one or more TMP multimers can be attached to each Fc domain. Also contemplated are other examples wherein the TMP dimers or multimers are attached to both the N and C-termini of one or both Fc domains, including the case wherein TMP dimers or multimers are attached to all four termini of two Fc domains. In instances wherein the vehicle is an Fc domain, the crystalline compounds of this embodiment wherein the vehicle is an Fc domain will have from about 200 to 400 amino acids in total.

In various embodiments, each TMP sequence in the crystalline compound is different from all other, each TMP sequence is the same, or two or more TMP sequences are the same.

Core Structures

In one aspect crystalline compounds comprise one or more TMP core structures having the sequence:

(SEQ ID NO: 113)
X2-X3-X4-X5-X6-X7-X8-X9-X10, wherein,

X2 is selected from the group consisting of Glu, Asp, Lys, and Val;

X3 is selected from the group consisting of Gly and Ala;

X4 is Pro;

X5 is selected from the group consisting of Thr and Ser;

X6 is selected from the group consisting of Leu, Ile, Val, Ala, and Phe;

X7 is selected from the group consisting of Arg and Lys;

X8 is selected from the group consisting of Gln, Asn, and Glu;

X9 is selected from the group consisting of Trp, Tyr, Phe, Cys and Ala; and

X10 is selected from the group consisting of Leu, Ile, Val, Ala, Phe, Met, and Lys.

In addition to the TMP core structure X2-X10 set forth above in this aspect, other related TMP structures are also possible wherein one or more of the following is added to the core-structure: X1 is attached to the N-terminus and/or X11, X12, X13, and/or X14 are attached to the C-terminus, wherein X1, X11, X12, X13, and X14 are as follows:

X1 is selected from the group consisting of Ile, Ala, Val, Leu, Ser, and Arg;

X11 is selected from the group consisting of Ala, Ile, Val, Leu, Phe, Ser, Thr, Lys, His, and Glu;

X12 is selected from the group consisting of Ala, Ile, Val, Leu, Phe, Gly, Ser, and Gln;

X13 is selected from the group consisting of Arg, Lys, Thr, Val, Asn, Gln, and Gly; and X14 is selected from the group consisting of Ala, Ile, Val, Leu, Phe, Thr, Arg, Glu, and Gly.

In another aspect, crystalline compounds comprise one or more TMP core structures having the sequence:

```
X1-X2-X3-X4-G-P-T-L-X9-X10-W-L-X13-X14-X15-X16-
X17-X18; (SEQ ID NO: 111)
``` wherein X1-X4, X9-X10, and X13-X18 are each independently an amino acid. In one aspect, this core is defined wherein:

X1 is selected from the group consisting of Ala, Val, Trp, Met, Gly, Tyr, Cys, Gln, Glu, Arg, and His;

X2 is selected from the group consisting of Ala, Val, Leu, Ile, Gly, Ser, and Cys;

X3 is selected from the group consisting of Leu, Ile, Pro, Trp, Gly, Ser, Asp, Lys, and Arg;

X4 is selected from the group consisting of Leu, Gly, Gln, Asp, Glu, and His;

X9 is selected from the group consisting of Lys and Arg;

X10 is selected from the group consisting of Gln and Glu;

X13 is selected from the group consisting of Ala, Val, Leu, Ser, Gln, Glu, and Arg;

X14 is selected from the group consisting of Ala, Trp, Thr, Tyr, Cys, and Gln;

X15 is selected from the group consisting of Val, Leu, Gly, Tyr, and Arg;

X16 is selected from the group consisting of Ala, Leu, Phe, Gly, and Arg;

X17 is selected from the group consisting of Ala, Val, Leu, Met, Gly, Cys, Gln, and Asn; and X18 is selected from the group consisting of Ala, Val, Pro, Met, Phe, Gly, Cys, Gln, and Lys.

In yet another aspect, the TMP core structure comprises the sequence:

```
                                        (SEQ ID NO: 112)
X1-X2-R-E-G-P-T-L-R-Q-W-L-X13-W-R-R-X17-X18
``` wherein X1, X2, X13, X17 and X18 are each independently an amino acid.

In one embodiment, this core is defined wherein:

X1 is selected from the group consisting of Ala, Val, Trp, Met, Gly, Tyr, Cys, Gln, Glu, Arg, and His;

X2 is selected from the group consisting of Ala, Val, Leu, Ile, Gly, Ser, and Cys;

X13 is selected from the group consisting of Ala, Val, Leu, Ser, Gln, Glu, and Arg;

X17 is selected from the group consisting of Ala, Val, Leu, Met, Gly, Cys, Gln, and Asn; and X18 is selected from the group consisting of Ala, Val, Pro, Met, Phe, Gly, Cys, Gln, and Lys.

In each aspect described herein, the term "TMP" as part of a crystalline compound is used to mean a moiety made up of a core structure wherein the amino acids X are independently selected from among the 20 naturally-occurring amino acids. In another aspect, the invention embraces crystalline compounds where each amino acid X is independently selected from the group of atypical, non-naturally occurring amino acids well known in the art. In various aspects, the amino acids have either L or D stereochemistry (except for Gly, which is neither L nor D), and in still other aspects, the TMPs comprise a combination of stereochemistries. Crystalline compounds contemplated also include reverse TMP molecules wherein the amino terminal to carboxy terminal sequence of the amino acids is reversed. For example, the reverse of a molecule having the normal sequence X1-X2-X3 would be X3-X2-X1. The crystalline compounds also include retro-reverse TMP molecules wherein, like a reverse TMP, the amino terminal to carboxy terminal sequence of amino acids is reversed and residues that are normally "L" enantiomers in TMP are altered to the "D" stereoisomer form.

In one aspect, compounds are linear or cyclic. By "cyclic" is meant that at least two separated, i.e., non-contiguous, portions of the molecule are linked to each other. For example, the amino and carboxy terminus of the ends of the molecule are covalently linked to form a cyclic molecule. Alternatively, the molecule contains two or more Cys residues (e.g., in the linker), which are cyclized via disulfide bond formation. It is further contemplated that more than one tandem peptide dimer are linked to form a dimer of dimers. Thus, for example, a tandem dimer containing a Cys residue forms an intermolecular disulfide bond with a Cys of another such dimer.

In each aspect of the crystalline compounds provided, physiologically acceptable salts are encompassed. Examples of such salts include without limitation acetate, trifluoroacetate, hydrochloride, hydrobromide, sulfate, citrate, tartrate, glycolate, oxalate.

It is also contemplated that "derivatives" of the TMP core structures may be substituted for the above-described TMP structures. Such derivative TMP core structures include moieties wherein one or more of the following modifications have been made:

one or more of the peptidyl [—C(O)NR—] linkages (bonds) are replaced by a non-peptidyl linkage such as a —$CH_2$-carbamate linkage [—$CH_2$—OC(O)NR—]; a phosphonate linkage; a —$CH_2$-sulfonamide [—$CH_2$—$S(O)_2$NR—] linkage; a urea [—NHC(O)NH—] linkage; a —$CH_2$-secondary amine linkage; or an alkylated peptidyl linkage [—C(O)$NR^6$— where $R^6$ is lower alkyl];

peptides wherein the N-terminus is derivatized to a —$NRR^1$ group; to a —NRC(O)R group; to a —NRC(O)OR group; to a —$NRS(O)_2$R group; to a —NHC(O)NHR group, where R and $R^1$ are hydrogen or lower alkyl, with the proviso that R and $R^1$ are not both hydrogen; to a succinimide group; to a benzyloxycarbonyl-NH—(CBZ-NH—) group; or to a benzyloxycarbonyl-NH— group having from 1 to 3 substituents on the phenyl ring selected from the group consisting of lower alkyl, lower alkoxy, chloro, and bromo; and peptides wherein the free C terminus is derivatized to —C(O)$R^2$ where $R^2$ is selected from the group consisting of lower alkoxy and —$NR^3R^4$ where $R^3$ and $R^4$ are indepdendently selected from the group consisting of hydrogen and lower alkyl. By "lower" is meant a group having from 1 to 6 carbon atoms.

Additionally, modifications of individual amino acids are introduced into the TMP molecule by reacting targeted amino acid residues of the peptide with an organic derivatizing agent that is capable of reacting with selected side chains or terminal residues. The following are without limitation exemplary.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine guanidino group.

The specific modification of tyrosyl residues per se has been studied extensively, with particular interest in introducing spectral labels into tyrosyl residues by reaction with aromatic diazonium compounds or tetraniitromethane. Most commonly, N-acetylimidizole and tetranitromethane is used to form O-acetyl tyrosyl species and 3-nitro derivatives, respectively.

Carboxyl side groups (aspartyl or glutamyl) are selectively modified by reaction with carbodiimides (R'—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are deamidated to the corresponding glutamyl and aspartyl residues. Alternatively, these residues are deamidated under mildly acidic conditions.

Derivatization with bifunctional agents is useful for cross-linking the peptides or their functional derivatives to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

A disulfide bond is replaced with another, preferably-more stable, cross-linking moiety (e.g., an alkylene). See, e.g., Bhatnagar et al. (1996), J. Med. Chem. 39: 3814-9; Alberts et al. (1993) Thirteenth Am. Pep. Symp., 357-9.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains (Creighton, T. E., Proteins: Structure and Molecule Properties, W. H. Freeman & Co., San Francisco, pp. 79-86 (1983)), acetylation of the N-terminal amine, and, in some instances, amidation of the C-terminal carboxyl groups.

Any peptide containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized as described herein.

Additional useful peptide sequences may result from conservative and/or non-conservative modifications of the amino acid sequences of the TMPs disclosed herein. Conservative modifications will produce peptides having functional and chemical characteristics similar to those of the peptide from which such modifications are made. In contrast, substantial modifications in the functional and/or chemical characteristics of the peptides may be accomplished by selecting substitutions in the amino acid sequence that differ significantly in their effect on maintaining (a) the structure of the molecular backbone in the area of the substitution, for example, as a sheet or helical conformation, (b) the charge or hydrophobicity of the molecule at the target site, or (c) the size of the molecule.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., 1998, Acta Physiol. Scand. Suppl. 643:55-67; Sasaki et al., 1998, Adv. Biophys. 35:1-24, which discuss alanine scanning mutagenesis).

Desired amino acid substitutions (whether conservative or non-conservative) can be determined by those skilled in the art at the time such substitutions are desired. For example, amino acid substitutions can be used to identify important residues of the peptide sequence, or to increase or decrease the affinity of the peptide or vehicle-peptide molecules (see preceding formulae) described herein. Exemplary amino acid substitutions are set forth in Table 1.

TABLE 1

Amino Acid Substitutions

| Original Residues | Exemplary Substitutions | Preferred Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Set (S) | Thr, Ala, Cys | Thr |

TABLE 1-continued

Amino Acid Substitutions

| Original Residues | Exemplary Substitutions | Preferred Substitutions |
|---|---|---|
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In various embodiments, conservative amino acid substitutions also encompass non-naturally occurring amino acid residues which are typically incorporated by chemical peptide synthesis rather than by synthesis in biological systems.

Naturally occurring residues may be divided into classes based on common sidechain properties that may be useful for modifications of sequence. For example, non-conservative substitutions may involve the exchange of a member of one of these classes for a member from another class. Such substituted residues may be introduced into regions of the peptide that are homologous with non-human orthologs, or into the non-homologous regions of the molecule. In addition, one may also make modifications using P or G for the purpose of influencing chain orientation.

In making such modifications, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157: 105-131 (1982). It is known that certain amino acids may be substituted for other amino acids having a similar hydropathic index or score and still retain a similar biological activity. In making changes based upon the hydropathic index, the substitution of amino acids whose hydropathic indices are within +2 is preferred, those which are within +1 are particularly preferred, and those within +0.5 are even more particularly preferred.

It is also understood in the art that the substitution of like amino acids can be made effectively on the basis of hydrophilicity. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within +2 is preferred, those which are within +1 are particularly preferred, and those within +0.5 are even more particularly preferred. One may also identify epitopes from primary amino acid sequences on the basis of hydrophilicity. These regions are also referred to as "epitopic core regions."

A skilled artisan will be able to determine suitable variants using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a peptide to similar peptides. With such a comparison, one can identify residues and portions of the molecules that are conserved among similar polypeptides. It will be appreciated that changes in areas of a peptide that are not conserved relative to such similar peptides would be less likely to adversely affect the biological activity and/or structure of the peptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the peptide structure.

Additionally, one skilled in the art can review structure-function studies identifying residues in similar peptides that are important for activity or structure. In view of such a comparison, one can predict the importance of amino acid residues in a peptide that correspond to amino acid residues that are important for activity or structure in similar peptides. One skilled in the art may opt for chemically similar amino acid substitutions for such predicted important amino acid residues of the peptides.

One skilled in the art can also analyze the three-dimensional structure and amino acid sequence in relation to that structure in similar polypeptides. In view of that information, one skilled in the art may predict the alignment of amino acid residues of a peptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays know to those skilled in the art. Such data could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4): 422-427 (1996), Chou et al., Biochemistry, 13(2): 222-245 (1974); Chou et al., Biochemistry, 113(2): 211-222 (1974); Chou et al., Adv. Enzymol. Relat. Areas Mol. Biol., 47: 45-148 (1978); Chou et al., Ann. Rev. Biochem., 47: 251-276 and Chou et al., Biophys. J., 26: 367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al, Nucl. Acid. Res., 27(1): 244-247 (1999). It has been suggested (Brenner et al., Curr. Op. Struct. Biol., 7(3): 369-376 (1997)) that there are a limited number of folds in a given polypeptide or protein and that once a critical number of structures have been resolved, structural prediction will gain dramatically in accuracy.

Additional methods of predicting secondary structure include "threading" (Jones, D., Curr. Opin. Struct. Biol., 7(3): 377-87 (1997); Sippl et al., Structure, 4(1): 15-9 (1996)), "profile analysis" (Bowie et al., Science, 253: 164-170 (1991); Gribskov et al., Meth. Enzym., 183: 146-159 (1990); Gribskov et al., Proc. Nat. Acad. Sci., 84(13): 4355-8 (1987)), and "evolutionary linkage" (See Home, supra, and Brenner, supra).

Compounds of the present invention may be changed at the DNA level, as well. The DNA sequence of any portion of the compound may be changed to codons more compatible with the chosen host cell. For *E. coli*, which is the preferred host cell, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes. Thus, all modifications and derivitizations discussed herein apply equally to all aspects of the present invention, including but not limited to peptides, peptide dimers and multimers, linkers, and vehicles.

Another set of useful derivatives are the above-described molecules conjugated to toxins, tracers, or radioisotopes. Such conjugation is especially useful for molecules comprising peptide sequences that bind to tumor cells or pathogens. Such molecules may be used as therapeutic agents or as an aid to surgery (e.g., radioimmunoguided surgery or RIGS) or as diagnostic agents (e.g., radioimmunodiagnostics or RID).

As therapeutic agents, these conjugated derivatives possess a number of advantages. They facilitate use of toxins and radioisotopes that would be toxic if administered without the specific binding provided by the peptide sequence. They also can reduce the side-effects that attend the use of radiation and chemotherapy by facilitating lower effective doses of the conjugation partner.

Useful conjugation partners include:
radioisotopes, such as 90Yttrium, 131Iodine, 225Actinium, and 213Bismuth;
ricin A toxin, microbially derived toxins such as *Pseudomonas* endotoxin (e.g., PE38, PE40), and the like;
partner molecules in capture systems (see below);
biotin, streptavidin (useful as either partner molecules in capture systems or as tracers, especially for diagnostic use); and
cytotoxic agents (e.g., doxorubicin).

One useful adaptation of these conjugated derivatives is use in a capture system. In such a system, the molecule of the present invention would comprise a benign capture molecule. This capture molecule would be able to specifically bind to a separate effector molecule comprising, for example, a toxin or radioisotope. Both the vehicle-conjugated molecule and the effector molecule would be administered to the patient. In such a system, the effector molecule would have a short half-life except when bound to the vehicle-conjugated capture molecule, thus minimizing any toxic side-effects. The vehicle-conjugated molecule would have a relatively long half-life but would be benign and nontoxic. The specific binding portions of both molecules can be part of a known specific binding pair (e.g., biotin, streptavidin) or can result from peptide generation methods such as those described herein.

Such conjugated derivatives may be prepared by methods known in the art. In the case of protein effector molecules (e.g., *Pseudomonas* endotoxin), such molecules can be expressed as fusion proteins from correlative DNA constructs. Radioisotope conjugated derivatives may be prepared, for example, as described for the BEXA antibody (Coulter). Derivatives comprising cytotoxic agents or microbial toxins may be prepared, for example, as described for the BR96 antibody (Bristol-Myers Squibb). Molecules employed in capture systems may be prepared, for example, as described by the patents, patent applications, and publications from NeoRx. Molecules employed for RIGS and RID may be prepared, for example, by the patents, patent applications, and publications from NeoProbe.

Such derivatized moieties improve one or more characteristics including thrombopoietic activity, solubility, absorption, biological half life, and the like of the crystalline compounds. Alternatively, derivatized moieties result in compounds that have the same, or essentially the same, characteristics and/or properties of the compound that is not derivatized. These moieties alternatively eliminate or attenuate any undesirable side effect of the compounds and the like.

Linkers

As noted above, the crystalline compounds in one aspect are TMP dimers which are either bonded directly or are linked by a linker group. The monomeric TMP moieties are shown in the conventional orientation from N to C terminus reading from left to right. Accordingly, it can be seen that the crystalline compounds are all oriented so that the C terminus of TMP1 is attached either directly or through a linker to the N-terminus of TMP2. This orientation is referred to as a tandem orientation, and these crystalline compounds may be generally referred to as "tandem dimmers." These compounds are referred to as dimers even if TMP1 and TMP2 are structurally distinct. That is, both homodimers and heterodimers are envisioned.

The "linker" group ("L1") is optional. When it is present, it is not critical what its chemical structure is, since it serves primarily as a spacer. The linker is chosen so as not to interfere with the biological activity of the final compound and also so that immunogenicity of the final compound is not significantly increased. In one aspect, the linker is made up of amino acids linked together by peptide bonds. Thus, in one embodiment, the linker comprises $Y_n$, wherein Y is a naturally occurring amino acid or a stereoisomer thereof and "n" is any one of 1 through 20. The linker is therefore made up of from 1 to 20 amino acids linked by peptide bonds, wherein the amino acids are selected from the 20 naturally-occurring amino acids. In a more preferred embodiment, the 1 to 20 amino acids are selected from Gly, Ala, Pro, Asn, Gln, Cys, Lys. Thus, in one aspect, a linker comprises (Gly)n, wherein n is 1 through 20, and when n is greater than 1, up to half of the Gly residues may be substituted by another amino acid selected from the remaining 19 natural amino acids or a stereoisomer thereof. Linkers of the invention are described in more detailed below.

In various aspects, the linker is made up of a majority of amino acids that are sterically un-hindered, such as Gly, Gly-Gly [$(Gly)_2$], Gly-Gly-Gly [$(Gly)_3$] . . . $(Gly)_{20}$ (SEQ ID NO:114), Ala, Gly-Ala, Ala-Gly, Ala-Ala, etc. Other specific examples of linkers are:
$(Gly)_3Lys(Gly)_4$ (SEQ ID NO: 2);
$(Gly)_3AsnGlySer(Gly)_2$ (SEQ ID NO: 3) (this structure provides a site for glycosylation, when it is produced recombinantly in a mammalian cell system that is capable of glycosylating such sites);

```
(Gly)3Cys(Gly)4        (SEQ ID NO: 4);
and

GlyProAsnGly           (SEQ ID NO: 5).
```

To explain the above nomenclature, for example, (Gly)$_3$Lys (Gly)$_4$ (SEQ ID NO:2) means Gly-Gly-Gly-Lys-Gly-Gly-Gly-Gly (SEQ ID NO:2). Combinations of Gly and Ala are also preferred.

Non-peptide linkers are also contemplated. For example, in one aspect alkyl linkers such as —HN—(CH$_2$)$_s$—CO—, wherein s=2-20 are used. These alkyl linkers are optionally substituted by any non-sterically hindering group such as lower alkyl (e.g., C$_1$-C$_6$), lower acyl, halogen (e.g., Cl, Br), CN, NH$_2$, phenyl, etc.

Another type of non-peptide linker is a polyethylene glycol group, such as:

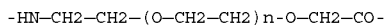

```
-HN-CH2-CH2-(O-CH2-CH2)n-O-CH2-CO-
``` wherein n is such that the overall molecular weight of the linker ranges from approximately 100 to 5000, preferably 100 to 500.

In general, a linker of a length of about 0-14 subunits (e.g., amino acids) is useful for the crystalline compounds of the various embodiment of this invention.

In another aspect, the peptide linkers are altered to form derivatives in the same manner as described above for the TMPs.

In one aspect as discussed above, compounds are linear or cyclic. In aspects of these embodiments, cyclization and/or dimer formation is effected through interactions between amino acid residues in the linker sequence.

Vehicles

In yet another embodiment, crystalline compounds of the present invention are linked or attached to a vehicle (V). A vehicle generally refers to a molecule that prevents degradation and/or increases half-life, reduces toxicity, reduces immunogenicity, or increases biological activity of a therapeutic protein. The vehicle (V) may be attached to a peptide through the N-terminus, C terminus, peptide backbone or a sidechain. Multiple vehicles may also be used; e.g., Fc's at each terminus or an Fc at a terminus and a PEG group at the other terminus or a sidechain.

In this aspect, crystalline compounds of the invention are covalently or noncovalently associated with a vehicle, such as a linear polymer (e.g., polyethylene glycol, polylysine, dextran, etc.), a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group (such as a steroid); or a carbohydrate or oligosaccharide. Other carriers include one or more water soluble polymer attachments such as polyoxyethylene glycol, or polypropylene glycol as described U.S. Pat. Nos. 4,640,835, 4,496,689, 4,301,144, 4,670,417, 4,791,192 and 4,179,337. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of these polymers.

Exemplary vehicles also include:
an Fc domain;
other proteins, polypeptides, or peptides capable of binding to a salvage receptor;
human serum albumin (HSA);
a leucine zipper (LZ) domain;
polyethylene glycol (PEG), including 5 kD, 20 kD, and 30 kD PEG, as well as other polymers;
dextran; and
other molecules known in the art to provide extended half-life and/or protection from proteolytic degradation or clearance.

In one aspect, the vehicle is polyethylene glycol (PEG). In this aspect, the PEG group is of any convenient molecular weight and in different aspects, the PEG group is straight chain or branched. The average molecular weight of the PEG generally ranges from about 2 kDa to about 100 kDa, from about 5 kDa to about 50 kDa, or from about 5 kDa to about 10 kDa.

The PEG groups is generally be attached to the crystalline compound via acylation, reductive alkylation, Michael addition, thiol alkylation or other chemoselective conjugation/ligation methods through a reactive group on the PEG moiety (e.g., an aldehyde, amino, ester, thiol, haloacetyl, maleimido or hydrazino group) to a reactive group on the target compound (e.g., an aldehyde, amino, ester, thiol, haloacetyl, maleimido or hydrazino group).

In another aspect, carbohydrate (oligosaccharide) groups are attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. In one aspect, X is one of the 19 naturally occurring amino acids not counting proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) are incorporated in the linker of the compounds of this invention and in one aspect are glycosylated by a cell during recombinant production of the polypeptide compounds (e.g., in mammalian cells such as CHO, BHK, COS). In other aspects, however, such sites are glycosylated by synthetic or semi-synthetic procedures known in the art.

An alternative vehicle would be a protein, polypeptide, peptide, antibody, antibody fragment, or small molecule (e.g., a peptidomimetic compound) capable of binding to a salvage receptor. For example, one could use as a vehicle a polypeptide as described in U.S. Pat. No. 5,739,277, issued Apr. 14, 1998 to Presta et al. Peptides could also be selected by phage display for binding to the FcRn salvage receptor. See, for example, WO 96/32478. Such salvage receptor-binding compounds are also included within the meaning of "vehicle" and are within the scope of this invention. Such vehicles should be selected for increased half-life (e.g., by avoiding sequences recognized by proteases) and decreased immunogenicity (e.g., by favoring non-immunogenic sequences, as discovered in antibody humanization).

Fc Domain Vehicles

A crystalline compound which includes an Fc domain as a vehicle moiety is referred to as a peptibody.

In one aspect, the Fc domains of the above crystalline compounds are selected from the human immunoglobulin IgG-1 heavy chain, see Ellison, J. W. et al., Nucleic Acids Res. 10:4071-4079 (1982), or any other Fc domain known in the art (e.g., other IgG classes including but not limited to IgG-2, IgG-3 and IgG-4, or other immunoglobulins).

It is well known that Fc domains of antibodies are made up of monomeric polypeptide segments that may be linked into dimeric or multimeric forms by disulfide bonds or by non-covalent association. The number of intermolecular disulfide bonds between monomeric subunits of native Fc molecules ranges from 1 to 4 depending on the class (e.g., IgG, IgA, IgE) or subclass (e.g., IgG1, IgG2, IgG3, IgA1, IgGA2) of antibody involved. The term "Fc" as used herein is generic to the monomeric, dimeric, and multimeric forms of Fc molecules. It should be noted that Fc monomers will spontaneously dimerize when the appropriate Cys residues are present unless particular conditions are present that prevent dimerization through disulfide bond formation. Even if the Cys residues that normally form disulfide bonds in the Fc dimer are removed or replaced by other residues, the monomeric chains will generally dimerize through non-covalent interactions: The term "Fc" herein is used to mean any of these forms: the native monomer, the native dimer (disulfide bond linked), modified dimers (disulfide and/or non-covalently linked), and modified monomers (i.e., derivatives).

Variants, analogs or derivatives of the Fc portion useful in the crystalline compounds are constructed by, for example, making various substitutions of residues or sequences.

Variant (or analog) polypeptides include insertion variants, wherein one or more amino acid residues supplement an Fc amino acid sequence. Insertions are located at either or both termini of the protein, or positioned within internal regions of the Fc amino acid sequence. Insertional variants with additional residues at either or both termini include for example, fusion proteins and proteins including amino acid tags or labels. For example, in one aspect, the Fc molecule optionally contains an N-terminal Met, especially when the molecule is expressed recombinantly in a bacterial cell such as *E. coli*.

In Fc deletion variants, one or more amino acid residues in an Fc polypeptide are removed. Deletions are effected at one or both termini of the Fc polypeptide, or with removal of one or more residues within the Fc amino acid sequence. Deletion variants, therefore, include all fragments of an Fc polypeptide sequence.

In Fc substitution variants, one or more amino acid residues of an Fc polypeptide are removed and replaced with alternative residues. In one aspect, the substitutions are conservative in nature, however, the invention embraces substitutions that ore also non-conservative. For example, in one embodiment, cysteine residues are deleted or replaced with other amino acids to prevent formation of some or all disulfide crosslinks of the Fc sequences. In one aspect, each cysteine residue is deleted or substituted with other amino acids, such as Ala or Ser. As another example, modifications are made to introduce amino acid substitutions to (1) ablate the Fc receptor binding site; (2) ablate the complement (C1q) binding site; and/or to (3) ablate the antibody dependent cell-mediated cytotoxicity (ADCC) site. Such sites are known in the art, and any known substitutions are within the scope of Fc as used herein. For example, see *Molecular Immunology, Vol. 29*, No. 5, 633-639 (1992) with regards to ADCC sites in IgG1.

In another aspect, one or more tyrosine residues are replaced by phenylalanine residues. In addition, other variant amino acid insertions, deletions (e.g., from 1-25 amino acids) and/or substitutions are also contemplated and are within the scope of the present invention. In one aspect, conservative amino acid substitutions are contemplated. In another aspect, substitutions include altered amino acids, such as peptidomimetics or D-amino acids.

In another embodiment, Fc sequences of the TMP compound are derivatized, i.e., bearing modifications other than insertion, deletion, or substitution of amino acid residues. In one aspect, the modifications are covalent in nature, and include for example, chemical bonding with polymers, lipids, other organic, and inorganic moieties. In various aspects, derivatives of the invention increase circulating half-life, or improve targeting capacity for the polypeptide to desired cells, tissues, or organs.

Additional members of the class of molecules designated as Fc herein are those that are described in WO 97/34631, the disclosure of which is incorporated by reference.

As noted, Fc variants are suitable vehicles within the scope of this invention. A native Fc may be extensively modified to form an Fc variant, provided binding to the salvage receptor is maintained; see, for example WO 97/34631 and WO 96/32478. In such Fc variants, one may remove one or more sites of a native Fc that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). Even when cysteine residues are removed, the single chain Fc domains can still form a dimeric Fc domain that is held together non-covalently.

2. A native Fc is modified to make it more compatible with a selected host cell. For example, one may remove the PA sequence near the N-terminus of a typical native Fc, which may be recognized by a digestive enzyme in *E. coli* such as proline iminopeptidase. One may also add an N-terminal methionine residue, especially when the molecule is expressed recombinantly in a bacterial cell such as *E. coli*.

3. A portion of the N-terminus of a native Fc is removed to prevent N-terminal heterogeneity when expressed in a selected host cell. For this purpose, one may delete any of the first 20 amino acid residues at the N-terminus, particularly those at positions 1, 2, 3, 4 and 5.

4. One or more glycosylation sites are removed. Residues that are typically glycosylated (e.g., asparagine) may confer cytolytic response. Such residues may be deleted or substituted with unglycosylated residues (e.g., alanine).

5. Sites involved in interaction with complement, such as the C1q binding site, are removed. For example, one may delete or substitute the EKK sequence of human IgG1. Complement recruitment may not be advantageous for the molecules of this invention and so may be avoided with such an Fc variant.

6. Sites are removed that affect binding to Fc receptors other than a salvage receptor. A native Fc may have sites for interaction with certain white blood cells that are not required for the fusion molecules of the present invention and so may be removed.

7. The ADCC site is removed. ADCC sites are known in the art; see, for example, Molec. Immunol. 29 (5): 633-9 (1992)

with regard to ADCC sites in IgG1. These sites, as well, are not required for the fusion molecules of the present invention and so may be removed.

8. When the native Fc is derived from a non-human-antibody, the native Fc may be humanized. Typically, to humanize a native Fc, one will substitute selected-residues in the non-human native Fc with residues that are normally found in human native Fc. Techniques for antibody humanization are well known in the art.

In various embodiments, the Fc domain is positioned at the N or C terminus of TMP1 or TMP2 or at both the N and C termini of the TMPs.

When the Fc chain is fused at the N-terminus of the TMP or linker, such fusion will generally occur at the C-terminus of the Fc chain, and vice versa.

Exemplary TMPs

The various components of the crystalline compounds having been broadly defined, non-limited exemplary peptides are shown below. Single letter amino acid abbreviations are used, and the linker is shown separated by dashes for clarity. As used below, BrAc means bromoacetyl (BrCH$_2$C(O)).

Non-limiting exemplary TMP core sequences are set out below.

```
GAREGPTLRQWLEWVRVG    (SEQ ID NO: 6)
RDLDGPTLRQWLPLPSVQ    (SEQ ID NO: 7)
ALRDGPTLKQWLEYRRQA    (SEQ ID NO: 8)
ARQEGPTLKEWLFWVRMG    (SEQ ID NO: 9)
EALLGPTLREWLAWRRAQ    (SEQ ID NO: 10)
MARDGPTLREWLRTYRMM    (SEQ ID NO: 11)
WMPEGPTLKQWLFHGRGQ    (SEQ ID NO: 12)
HIREGPTLRQWLVALRMV    (SEQ ID NO: 13)
QLGHGPTLRQWLSWYRGM    (SEQ ID NO: 14)
ELRQGPTLHEWLQHLASK    (SEQ ID NO: 15)
VGIEGPTLRQWLAQRLNP    (SEQ JD NO: 16)
WSRDGPTLREWLAWRAVG    (SEQ ID NO: 17)
AVPQGPTLKQWLLWRRCA    (SEQ ID NO: 18)
RIREGPTLKEWLAQRRGF    (SEQ ID NO: 19)
RFAEGPTLREWLEQRKLV    (SEQ ID NO: 20)
DRFQGPTLREWLAAIRSV    (SEQ ID NO: 21)
AGREGPTLREWLNMRVWQ    (SEQ ID NO: 22)
ALQEGPTLRQWLGWGQWG    (SEQ ID NO: 23)
YCDEGPTLKQWLVCLGLQ    (SEQ ID NO: 24)
WCKEGPTLREWLRWGFLC    (SEQ ID NO: 25)
CSSGGPTLREWLQCRRMQ    (SEQ ID NO: 26)
CSWGGPTLKQWLQCVRAK    (SEQ ID NO: 27)
CQLGGPTLREWLACRLGA    (SEQ ID NO: 28)
CWEGGPTLKEWLQCLVER    (SEQ ID NO: 29)
CRGGGPTLHQWLSCFRWQ    (SEQ ID NO: 30)
CRDGGPTLRQWLACLQQK    (SEQ ID NO: 31)
ELRSGPTLKEWLVWRLAQ    (SEQ ID NO: 32)
GCRSGPTLREWLACREVQ    (SEQ ID NO: 33)
TCEQGPTLRQWLLCRQGR    (SEQ ID NO: 34)
```

Non-limiting exemplary dimeric compounds are set out below.

```
                                          (SEQ. ID NO: 35)
    IEGPTLRQWLAARA-GPNG-IEGPTLRQWLAARA
                                          (SEQ. ID NO: 36)
IEGPTLRQCLAARA-GGGGGGGG-IEGPTLRQCLAARA (cyclic)
    |_____|

(SEQ. ID NO: 37)
IEGPTLRQCLAARA-GGGGGGGG-IEGPTLRQCLAARA (linear)
                                          (SEQ. ID NO: 38)
    IEGPTLRQALAARA-GGGGGGGG-IEGPTLRQALAARA
                                          (SEQ. ID NO: 39)
    IEGPTLRQWLAARA-GGGKGGGG-IEGPTLRQWLAARA
                                          (SEQ. ID NO: 40)
    IEGPTLRQWLAARA-GGGK(BrAc)GGGG-IEGPTLRQWLAARA
                                          (SEQ. ID NO: 41)
    IEGPTLRQWLAARA-GGGCGGGG-IEGPTLRQWLAARA
                                          (SEQ. ID NO: 42)
    IEGPTLRQWLAARA-GGGK(PEG)GGGG-IEGPTLRQWLAARA
                                          (SEQ. ID NO: 43)
    IEGPTLRQWLAARA-GGGC(PEG)GGGG-IEGPTLRQWLAARA
                                          (SEQ. ID NO: 44)
    IEGPTLRQWLAARA-GGGNGSGG-IEGPTLRQWLAARA
                                          (SEQ. ID NO: 45)
    IEGPTLRQWLAARA-GGGCGGGG-IEGPTLRQWLAARA
    IEGPTLRQWLAARA-GGGCGGGG-IEGPTLRQWLAARA
                                          (SEQ. ID NO: 46)
    IEGPTLRQWLAARA-GGGGGGGG-IEGPTLRQWLAARA
```

In each of the above compounds, an N-terminal Met (or M residue, using the one-letter code) is contemplated as well. Multimers (e.g., tandem and non-tandem, covalently bonded and non-covalently bonded) of the compounds, both monomeric and dimeric, are also contemplated.

Accordingly, the compounds of this group have structures as defined for the first group of compounds as described above, but these compounds are further fused to at least one Fc group either directly or through one or more linker groups.

Nonlimiting exemplary compounds modified to include an Fc domain are as follows:

```
                                          (SEQ. ID NO: 47)
    Fc-IEGPTLRQWLAARA-GPNG-IEGPTLRQWLAARA
                                          (SEQ. ID NO: 48)
    Fc-IEGPTLRQWLAARA-GPNG-IEGPTLRQWLAARA-Fc
                                          (SEQ. ID NO: 49)
    IEGPTLRQWLAARA-GGGGGGGG-IEGPTLRQWLAARA-Fc
                                          (SEQ. ID NO: 50)
    Fc-GG-IEGPTLRQWLAARA-GPNG-IEGPTLRQWLAARA
```

(SEQ. ID NO: 51)
Fc-IEGPTLRQWLAARA-GGGGGGGG-IEGPTLRQWLAARA (SEQ. ID NO: 52)
Fc-IEGPTLRQCLAARA-GGGGGGGG-IEGPTLRQCLAARA (cyclic)
   |_____|

(SEQ. ID NO: 53)
Fc-IEGPTLRQCLAARA-GGGGGGGG-IEGPTLRQCLAARA (linear)

(SEQ. ID NO: 54)
Fc-IEGPTLRQALAARA-GGGGGGGG-IEGPTLRQALAARA (SEQ. ID NO: 55)
Fc-IEGPTLRQWLAARA-GGGKGGGG-IEGPTLRQWLAARA (SEQ. ID NO: 56)
Fc-IEGPTLRQWLAARA-GGGCGGGG-IEGPTLRQWLAARA (SEQ. ID NO: 57)
Fc-IEGPTLRQWLAARA-GGGNGGGG-IEGPTLRQWLAARA (SEQ. ID NO: 58)
Fc-IEGPTLRQWLAARA-GGGCGGGG-IEGPTLRQWLAARA
                     |
Fc-IEGPTLRQWLAARA-GGGCGGGG-IEGPTLRQWLAARA (SEQ. ID NO: 59)
Fc-GGGGG-IEGPTLRQWLAARA-GGGGGGGG-IEGPTLRQWLAARA

In each of the above compounds, an additional N-terminal Met (or M residue, using the one-letter code) is contemplated as well. In these compounds, the Met residue is attached at the N-terminus of the Fc group in those cases wherein there is an Fc group attached to the N-terminus of the TMP. In those cases wherein the Fc group is attached at the C-terminus of the TMP, the Met residues is attached to the N-terminus of the TMP group.

In each of the above cases Fc is preferably the Fc region of the human immunoglobulin IgG1 heavy chain or a biologically active fragment, derivative, or dimer thereof, see Ellison, J. W. et al., Nucleic Acids Res. 10:4071-4079 (1982). In one aspect, the Fc sequence shown in SEQ ID NO: 1 is used in the above compounds. In alternative aspects, in the above compounds the Fc is a dimeric form of the sequence of SEQ ID NO: 1 and each Fc chain is attached to a TMP tandem dimer.

Still more exemplary compounds are shown below:

(SEQ ID NO 60)
CSSGGPTLREWLQCRRMQ-GGGGG-CSSGGPTLREWLQCRRMQ (SEQ ID NO 61)
QLGHGPTLRQWLSWYRGM-(Gly)$_3$Lys(Gly)$_4$-
ALRDGPTLKQWLEYRRQA;

(SEQ ID NO 62)
RFAEGPTLREWLEQRKLV-GGG(PEG)GGG-RFAEGPTLREWLEQRKLV.

(SEQ ID NO: 63)
HIREGPTLRQWLVALRMV-GGG(PEG)GGG-HIREGPTLRQWLVALRMV (SEQ ID NO: 64)
Fc-TCEQGPTLRQWLLCRQGR-GGGKGGG-TCEQGPTLRQWLLCRqGR-Fc (SEQ ID NO: 65)
Fc-QLGHGPTLRQWLSWYRGM-GPNG-ELRSGPTLKEWLVWRLAq (SEQ ID NO: 66)
CSWGGPTLKQWLQCVRAK-Fc
   |
SWGGPTLKQWLQCVRAK (SEQ ID NO: 67)
Fc-GGGKGGG-AVPQGPTLKQWLLWRRCA (SEQ ID NO: 68)
PEG-CSSGGPTLREWLQCRRMQ
        |
    CSSGGPTLREWLQCRRMQ (SEQ ID NO: 69)
Fc-GGGGG-YCDEGPTLKQWLVCLGLQ-GGGGG-
YCDEGPTLKQWLVCLGLQ (SEQ ID NO: 70)
CSWGGPTLKQWLQCVRAK-GGGAGGG-CSWGGPTLKQWLQCVRAK-
GGGAGGG-CSWGGPTLKQWLQCVRAK-GGGAGGG-Fc (SEQ ID NO: 71)
VGIEGPTLRQWLAQRLNP-GGGCGGG-VGIEGPTLRQWLAQRLNP-PEG (SEQ ID NO: 72)
Fc-ELRSGPTLKEWLVWRLAq-GGGG-ELRSGPTLKEWLVWRLAQ (SEQ ID NO: 73)
Fc-ALRDGPTLKQWLEYRRQA-GGGKGGG-
ALRDGPTLKQWLEYRRQA-Fc (SEQ ID NO: 74)
ALRDGPTLKQWLEYRRQA-ALRDGPTLKQWLEYRRQA (SEQ ID NO: 75)
EALLGPTLREWLAWRRAQ-EALLGPTLREWLAWRRAQ (SEQ ID NO: 76)
AVPQGPTLKQWLLWRRCA-AVPQGPTLKQWLLWRRCA (SEQ ID NO: 77)
YCDEGPTLKQWLVCLGLQ-YCDEGPTLKQWLVCLGLQ (SEQ ID NO: 78)
CSSGGPTLREWLQCRRMQ-CSSGGPTLREWLQCRRMQ (SEQ ID NO: 79)
CSWGGPTLKQWLQCVRAK-CSWGGPTLKQWLQCVRAK (SEQ ID NO: 80)
ALRDGPTLKQWLELYRRQA-GGGGG-ALRDGPTLKQWLEYRRQA (SEQ ID NO: 81)
EALLGPTLREWLAWRRAQ-GGGGG-EALLGPTLREWLAWRRAQ (SEQ ID NO: 82)
AVPQGPTLKQWLLWRRCA-GGGGG-AVPQGPTLKQWLLWRRCA (SEQ ID NO: 83)
YCDEGPTLKQWLVCLGLQ-GGGGG-YCDEGPTLKQWLVCLGLQ (SEQ ID NO: 84)
CSSGGPTLREWLQCRRMQ-GGGGG-CSSGGPTLREWLQCRRMQ (SEQ ID NO: 85)
CSWGGPTLKQWLQCVRAK-GGGGG-CSWGGPTLKQWLQCVRAK (SEQ ID NO: 86)
Fc-GGGGG-ALRDGPTLKQWLEYRRQA (SEQ ID NO: 87)
Fc-GGGGG-EALLGPTLREWLAWRRAQ (SEQ ID NO: 88)
Fc-GGGGG-AVPQGPTLKQWLLWRRCA (SEQ ID NO: 89)
Fc-GGGGG-YCDEGPTLKQWLVCLGLQ (SEQ ID NO: 90)
Fc-GGGGG-CSSGGPTLREWLQCRRMQ (SEQ ID NO: 91)
Fc-GGGGG-CSWGGPTLKQWLQCVRAK (SEQ ID NO: 92)
Fc-GGGGG-ALRDGPTLKQWLEYRRQA-GGGGG-
ALRDGPTLKQWLEYRRQA

-continued

```
                                       (SEQ ID NO: 93)
Fc-GGGGG-EALLGPTLREWLAWRRAQ-GGGGG-
EALLGPTLREWLAWRRAQ
                                       (SEQ ID NO: 94)
Fc-GGGGG-AVPQGPTLKQWLLWRRCA-GGGGG-
AVPQGPTLKQWLLWRRCA
                                       (SEQ ID NO: 95)
Fc-GGGGG-YCDEGPTLKQWLVCLGLQ-GGGGG-
YCDEGPTLKQWLVCLGLQ
                                       (SEQ ID NO: 96)
Fc-GGGGG-CSSGGPTLREWLQCRRMQ-GGGGG-
CSSGGPTLREWLQCRRMQ
                                       (SEQ ID NO: 97)
Fc-GGGGG-CSWGGPTLKQWLQCVRAK-GGGGG-
CSWGGPTLKQWLQCVRAK
                                       (SEQ ID NO: 98)
ALRDGPTLKQWLEYRRQA-GGGGG-ALRDGPTLKQWLEYRRQA-
GGGGG-Fc
                                       (SEQ ID NO: 99)
EALLGPTLREWLAWRRAQ-GGGGG-EALLGPTLREWLAWRRAQ-
GGGGG-Fc
                                       (SEQ ID NO: 100)
AVPQGPTLKQWLLWRRCA-GGGGG-AVPQGPTLKQWLLWRRCA-
GGGGG-Fc
                                       (SEQ ID NO: 101)
YCDEGPTLKQWLVCLGLQ-GGGGG-YCDEGPTLKQWLVCLGLQ-
GGGGG-Fc
                                       (SEQ ID NO: 102)
CSSGGPTLREWLQCRRMQ-GGGGG-CSSGGPTLREWLQCRRMQ-
GGGGG-Fc
                                       (SEQ ID NO: 103)
CSWGGPTLKQWLQCVRAK-GGGGG-CSWGGPTLKQWLQCVRAK-
GGGGG-Fc
                                       (SEQ ID NO: 104)
ALRDGPTLKQWLEYRRQA-GGGGG-Fc
                                       (SEQ ID NO: 105)
EALLGPTLREWLAWRRAQ-GGGGG-Fc
                                       (SEQ ID NO: 106)
AVPQGPTLKQWLLWRRCA-GGGGG-Fc
                                       (SEQ ID NO: 107)
YCDEGPTLKQWLVCLGLQ-GGGGG-Fc
                                       (SEQ ID NO: 108)
CSSGGPTLREWLQCRRMQ-GGGGG-Fc
                                       (SEQ ID NO: 109)
CSWGGPTLKQWLQCVRAK-GGGGG-Fc
```

Variant peptides are also contemplated which have at least 50%, at least 60%, at least 70%, at least 75%, at least 80%, at least 85%, at least 90%, at least 95%, at least 96%, at least 97%, at least 98% and at least 99% identity ("percent identity") with any of the exemplary crystalline compounds described here and possess a desired bioefficacy. It is understood that certain variants may possess a greater, equal or lesser degree of bioefficacy than the peptide to against which its percent identity is measured. Those variants with greater bioefficacy are important to evoke a greater biological response and possibly in a shorter period of time. Those with equal bioefficacy are important in those instances in which a patient may become refractory to treatment with another crystalline compound against which it's percent identity is determined. Those variants with lesser bioefficacy are important in instances which do not require the more substantial response evoked by the crystalline compound against which percent identity is determined. Variants of this type also provide an alternative therapeutic for those patients which may experience an inhibitory immunological response against a first-administered crystalline compound.

Methods of Making

The compounds described herein are made in a variety of ways. Since many of the compounds are peptides, or include a peptide, methods for synthesizing peptides are of particular relevance here. In one aspect, solid phase synthesis techniques are used. Suitable techniques are well known in the art, and include those described in Merrifield, in Chem. Polypeptides, pp. 0.335-61 (Katsoyannis and Panayotis eds. 1973); Merrifield, J. Am. Chem. Soc. 85:2149 (1963); Davis et al., Biochem. Intl. 10:394-414 (1985); Stewart and Young, Solid Phase Peptide Synthesis (1969); U.S. Pat. No. 3,941,763; Finn et al., The Proteins, 3rd ed., vol. 2, pp. 105-253 (1976); and Erickson et al., The Proteins, 3rd ed., vol. 2, pp. 257-527 (1976). Solid phase synthesis is the preferred technique of making individual peptides since it is the most cost-effective method of making small peptides.

In another aspect, peptides are made in transformed host cells using recombinant DNA techniques. To do so, a recombinant DNA molecule coding for the peptide, or a peptide-vehicle fusion, is prepared. Methods of preparing such DNA and/or RNA molecules are well known in the art. For example, sequences coding for the peptides are excised from DNA using suitable restriction enzymes. The relevant sequences are obtained using the polymerase chain reaction (PCR) with the inclusion of useful restriction sites for subsequent cloning. Alternatively, the DNA/RNA molecule is synthesized using chemical synthesis techniques, such as the phosphoramidite method. In another aspect, a combination of these or other techniques is used.

Also provided are vectors encoding the peptides in an appropriate host. The vector comprises the DNA molecule that encodes the peptides operatively linked to appropriate expression control sequences. Methods of effecting this operative linking, either before or after the peptide-encoding DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector comprising the peptide-encoding DNA molecule is used to transform an appropriate host. This transformation is performed using methods well known in the art.

Any of a large number of available and well-known host cells are used in the practice of this invention. The selection of a particular host is dependent upon a number of factors recognized by the art. These factors include, for example, compatibility with the chosen expression vector, toxicity to the host cell of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence.

Within these general guidelines, useful microbial hosts include bacteria (such as *E. coli*), yeast (such as *Saccharomyces* sp. and *Pichia pastoris*) and other fungi, insects, plants, mammalian (including human) cells in culture, or other hosts known in the art. The transformed host is cultured under conventional fermentation conditions so that the desired peptides are expressed. Such fermentation conditions are well known in the art. The peptides are then purified from the fermentation culture or from the host cells in which they are expressed. These purification methods are also well known in the art.

Depending on the host cell utilized to express a compound of the invention, carbohydrate (oligosaccharide) groups may conveniently be attached to sites that are known to be glycosylation sites in proteins.

In another aspect, compounds that contain derivatized-peptides or which contain non-peptide groups are synthesized by well-known organic chemistry techniques. For example, solid phase synthesis techniques is used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is a routine technique of making individual peptides since it is the most cost-effective method of making small peptides.

Purifying Polypeptides for Crystallization

Purification of the expressed peptides is performed by any standard method. When the peptide is produced intracellularly, the particulate debris is removed, for example, by centrifugation or ultrafiltration. When the peptide is secreted into the medium, supernatants from such expression systems is first concentrated using standard polypeptide concentration filters. Protease inhibitors are optionally added to inhibit proteolysis and antibiotics are optionally included to prevent the growth of microorganisms. Peptides are in one aspect produced in the presence of chaperone or accessory proteins in order to obtain a desired peptide conformation, or in another aspect are subjected to conditions such as oxidizing and/or reducing conditions after production in order to induce refolding or changes in peptide conformation (see, for example, WO 02/068455).

In one embodiment, a peptide is purified using, for example, hydroxyapatite chromatography, gel electrophoresis, dialysis, and affinity chromatography, and any combination of purification techniques known or yet to discovered. For example, protein A can be used to purify peptides expressed to include a Fc domain that is based on human gamma 1, gamma 2, or gamma 4 heavy chains (Lindmark et al., 1983, J. Immunol. Meth. 62:1-13), where the Fc domain contains the portion of the constant domain involved in binding to protein A. Protein G is recommended for human gamma 3 (Guss et al., 1986, EMBO J. 5:1567-1575). In other aspects, techniques for peptide purification are utilized, depending on need, including but not limited to fractionation on an ion-exchange column, precipitation with ethanol or other alcohols, reverse phase HPLC, FPLC, chromatography on silica, chromatography on heparin SEPHAROSET™, chromatography on an anion or cation exchange resin (such as a polyaspartic acid column), hydrophobic interaction chromatography, chromatofocusing, SDS-PAGE, and ammonium sulfate precipitation can also be utilized depending on need.

Production of Crystals, Crystal Formulations, and Compositions:

Polypeptide crystals are grown by controlled crystallization of compounds from aqueous solutions or from aqueous solutions containing organic solvents or additives. Solution conditions that are controlled include, for example, the rate of evaporation of solvent, organic solvents or additives, the presence of appropriate co-solutes and buffers, pH, and temperature. A comprehensive review of the various factors affecting the crystallization of proteins has been published by McPherson, 1985, Methods Enzymol 114: 112-120 as well as Coligan, et al., (Eds) *Current Protocols in Protein Science*, John Wiley & Sons, Inc., (1995-2002), pp. 17.4.1-17.4.25. In addition, McPherson and Gilliland, 1988, J Crystal Growth, 90: 51-59 have compiled comprehensive lists of polypeptides that have been crystallized, as well as the conditions under which they were crystallized. A compendium of crystals and crystallization recipes, as well as a repository of coordinates of solved protein structures, is maintained by the Protein Data Bank at the Brookhaven National Laboratory (www.rcsb.org/pdb/; Bernstein et al., 1977, J Mol Biol 112: 535-542). These references are used to determine the conditions necessary for crystallization of a peptide, as a prelude to the formation of appropriate polypeptide crystals and can guide the crystallization strategy for other polypeptide. It should be noted, however, that the conditions reported in most of the above-cited references have been optimized to yield, in most instances, a few large, diffraction quality crystals. Accordingly; it will be appreciated by those of skill in the art that some degree of adjustment of these conditions to provide a high yielding process for the large scale production of polypeptide crystals may be necessary.

In general, crystals are produced by combining the polypeptide to be crystallized with an appropriate aqueous solvent or aqueous solvent containing appropriate crystallization agents, such as salts or organic solvents or additives. The solvent is combined with the peptide and may be subjected to agitation at a temperature determined experimentally to be appropriate for the induction of crystallization and acceptable for the maintenance of peptide activity and stability. The solvent can optionally include co-solutes, such as divalent cations, co-factors, or chaotropes, as Well as buffer species to control pH. "Co-solutes means" for crystallization include compounds that can supply a co-solute to facilitate crystallization of a peptide. Examples of co-solute means include ammonium acetate, ammonium chloride, ammonium fluoride, ammonium formate, ammonium nitrate, ammonium phosphate, ammonium sulfate, cadmium chloride, cadmium sulfate, calcium acetate, calcium chloride, cesium chloride, cobaltous chloride, $CH_3(CH_2)_{15}N(CH_3)_3{}^+Br^-$ (CTAB), di-ammonium citrate, di-ammonium hydrogen phosphate, di-ammonium phosphate, di-ammonium tartrate, di-potassium phosphate, di-sodium phosphate, di-sodium tartrate, DL-malic acid, ferric chloride, L-proline, lithium acetate, lithium chloride, lithium nitrate, lithium sulfate, magnesium acetate, magnesium chloride, magnesium formate, magnesium nitrate, magnesium sulfate, nickel chloride, potassium acetate, potassium bromide, potassium chloride, potassium citrate, potassium fluoride, potassium formate, potassium nitrate, potassium phosphate, potassium sodium tartrate, potassium sulfate, potassium thiocyanate, sodium acetate, sodium bromide, sodium chloride, sodium citrate, sodium fluoride, sodium formate, sodium malonate, sodium nitrate, sodium phosphate, sodium sulfate, sodium thiocyanate, succinic acid, tacsimate, tri-ammonium citrate, tri-lithium citrate, trimethylamine N-oxide, tri-potassium citrate, tri-sodium citrate, zinc acetate, zinc sulfate, and other compounds that function to supply co-solutes. "Crystallization buffering means" include compounds that maintain the pH of a solution in a desired range to facilitate crystallization of a peptide. Examples of crystallization buffering means include ACES (N-(2-acetamido)-2-aminoethanesulfonic acid), BES (N,N-bis(2-hydroxyethyl)-2-aminoethanesulfonic acid), Bicine (N,N-Bis(2-hydroxyethyl)glycine), BIS-TRIS (2,2-bis(hydroxymethyl)-2,2',2"-nitrilotriethanol), boric acid, CAPS (3-[cyclohexylamino]-1-propanesulfonic acid), EPPS (HEPPS, 4-(2-Hydroxyethyl)piperazine-1-propanesulfonic acid), Gly-Gly ($NH_2CH_2CONHCH_2COOH$, glycyl-glycine), HEPES (4-(2-hydroxyethyl)piperazine-1-ethanesulfonic acid), imidazole, MES (2-morpholinoethanesulfonic acid), MOPS (3-(N-morpholino)propanesulfonic acid), PIPES (piperazine-1,4-bis(2-ethanesulfonic acid)), sodium acetate, sodium bicarbonate, sodium phosphate monobasic (sodium dihydrogen phosphate), TAPS(N-[tris(hydroxymethyl)methyl]-3-aminopropanesulfonic acid), TAPSO (N-[tris(hydroxymethyl)methyl]-3-amino-2-hydroxypropanesulfonic acid), TES (N-[tris(hydroxymethyl)methyl]-2-aminoethanesulfonic acid), Tricine (N-[tris(hydroxymethyl)methyl]glycine), Tris-HCl, TRIZMA (2-amino-2-(hydroxymethyl)-1,3-propanediol), and other compounds that function to maintain a solution at or near a specified pH.

The need for co-solutes, buffers, etc. and their concentrations are determined experimentally to facilitate crystallization. Some examples of suitable crystallization conditions for a peptide as described herein are described in Examples below. Additional descriptions of methods for crystallization of peptides are found in U.S. Patent Application No. 20020136719 and WO2005/012353, the disclosures of which are incorporated by reference herein in their entireties.

In an industrial-scale process, the controlled precipitation leading to crystallization is carried out by the simple combination of peptide, precipitant, co-solutes and, optionally, buffers in a batch process. As another option, peptides are crystallized by using peptide precipitates as the starting material ("seeding"). In this case, peptide precipitates are added to a crystallization solution and incubated until crystals form. Alternative laboratory crystallization methods, such as dialysis or vapor diffusion, are optionally adopted. McPherson, supra and Gilliland, supra, include a comprehensive list of suitable conditions in their reviews of the crystallization literature. Occasionally, in cases in which the crystallized peptide is to be crosslinked, incompatibility between an intended crosslinking agent and the crystallization medium might require exchanging the crystals into a more suitable solvent system.

According to one embodiment of this invention, peptide crystals, crystal formulations and compositions are prepared by the following process: first, the peptide is crystallized. Next, excipients or ingredients as described herein are added directly to the mother liquor. Alternatively, the crystals are suspended in a solution of excipient or other formulary ingredients, after the mother liquor is removed, for a minimum of 1 hour to a maximum of 24 hours. The excipient concentration is typically between about 0.01 to 30% W/W, which corresponds to a peptide crystal concentration of 99.99 to 70% W/W, respectively. In one embodiment, the excipient concentration is between about 0.1 to 10%, which corresponds to a crystal concentration of 99.9 to 90% W/W, respectively. The mother liquor is removed from the crystal slurry either by filtration or by centrifugation. Subsequently, the crystals are washed optionally with solutions of 50 to 100% one or more organic solvents or additives such as, for example, ethanol, methanol, isopropanol or ethyl acetate, either at room temperature or at temperatures between −20° C. to 25° C. The crystals are then dried either by passing a stream of nitrogen, air, or inert gas over the crystals. Alternatively, the crystals are dried by air drying or by lyophilization or by vacuum drying. The drying is carried out for a minimum 1 hour to a maximum of 72 hours after washing, until the moisture content of the final product is below 1.0% by weight, most preferably below 5%. Finally, micronizing of the crystals is performed if necessary. The drying of polypeptide crystals is the removal of water, organic solvent or additive, or liquid polymer by means including drying with $N_2$, air, or inert gases; vacuum oven drying; lyophilization; washing with a volatile organic solvent or additive followed by evaporation of the solvent; or evaporation in a fume hood. Typically, drying is achieved when the crystals become a free-flowing powder. Drying may be carried out by passing a stream of gas over wet crystals. The gas may be selected from the group consisting of: nitrogen, argon, helium, carbon dioxide, air or combinations thereof. The peptide crystals of the invention can be further processed to achieve a desired particle size distribution by micronizing in a suitable mill, such as a jet mill, and the components of the particle or powder formulation may be mixed before or after micronizing. The diameter of the particles achieved can be in the range of 0.1 to 100 micrometers, or in the range of 0.2 to 10 micrometers, or in the range of 10 to 50 micrometers, or in the range of 0.5 to 2 micrometers. For formulations to be administered by inhalation, in one embodiment the particles formed from the peptide crystals are in the range of 0.5 to 1 micrometers.

According to one embodiment, when preparing peptide crystals, peptide crystal formulations or compositions, enhancers, such as surfactants are not added during crystallization. Excipients or ingredients are added to the mother liquor after crystallization, at a concentration of between about 1-10% W/W, alternatively at a concentration of between about 0.1-25% W/W, alternatively at a concentration of between about 0.1-50% W/W. These concentrations correspond to crystal concentrations of 99-90% W/W, 99.9-75% W/W and 99.9-50% W/W; respectively. The excipient or ingredient is incubated with the crystals in the mother liquor for about 0.1-3 hrs, alternatively the incubation is carried out for 0.1-12 hrs, alternatively the incubation is carried out for 0.1-24 hrs.

In another embodiment, the ingredient or excipient is dissolved in a solution other than the mother liquor, and the peptide crystals are removed from the mother liquor and suspended in the excipient or ingredient solution. The ingredient or excipient concentrations and the incubation times are the same as those described above.

Peptide Crystals

As used herein, "crystal" or "crystalline" refers to one form of the solid state of matter, which is distinct from the amorphous solid state form. Crystals display characteristic features including a lattice structure, characteristic shapes, and optical properties such as refractive index and birefringence. A crystal consists of atoms arranged in a pattern that repeats periodically in three dimensions (C. S. Barrett, Structure of Metals, 2nd ed., McGraw-Hill, New York, 1952, p. 1). In contrast, amorphous material is a non-crystalline solid form of matter, sometimes referred to as an amorphous precipitate. Such precipitates have no molecular lattice structure characteristic of the crystalline solid state and do not display birefringence or other spectroscopic characteristics typical of the crystalline forms of matter.

Peptide crystals are peptide molecules arranged in a crystal lattice. Peptide crystals contain a pattern of specific peptide-peptide interactions that are repeated periodically in three dimensions. The peptide crystals of this invention are to be distinguished from amorphous solid forms or precipitates of peptides, such as those obtained by lyophilizing a peptide solution.

In peptide crystals, the peptide molecules form asymmetric units which are arranged together to form symmetric units. The geometric structure of the symmetric units of peptide crystals can be cubic, hexagonal, monoclinic, orthorhombic, tetragonal, triclinic, or trigonal. The overall structure of the crystals in their entirely can be in the form of bipyramids, cubes, needles, plates, prisms, rhomboids, rods, or spheres, or combinations thereof. Crystals that are of the "cubic" structural class can more specifically have octadecahedral or dodecahedral crystal forms. The diameter of the crystals is defined as the Martin's diameter. It is measured as the length of the line, parallel to the ocular scale, that divides the randomly oriented crystals into two equal projected areas. Crystals in forms such as needles or rods will also have a maximal dimension that is referred to herein as the length of the crystal.

"Crystalline compounds" as used herein refers to peptides as described herein in crystalline states wherein the peptides are optionally (i) bound to a vehicle as described herein, (ii) bound to one or more other peptides, including peptide(s) of the same or difference sequence(s), and/or a linker, (iii) bound to a moiety other than a peptide, i.e., bound to non-peptide moiety. As discussed herein, the crystalline compounds optionally include a precipitant salt.

Maintaining Crystal Structure

In order to use crystalline compounds as prepared herein as a peptide source for preparing formulations and compositions, the problem of protein crystal dissolution outside the crystallization solution has to be overcome. In order to maintain crystal structure, in the production of the crystalline compounds, several approaches are used.

1. Crystals remain in the mother liquor in the course of producing crystalline compounds encapsulated with polymeric carriers. Many compounds used in protein crystallization, such as salts, PEG and organic solvents, are compatible with polymer processing conditions.

2. The rate of crystal dissolution outside the mother liquor depends on conditions, such as pH, temperature, presence of metal ions, Such as zinc, copper; and calcium, and concentration of precipitants. By varying these conditions, dissolution of crystals is slowed for several hours.

0.3. The mother liquor is removed by filtration and the remaining crystalline paste dried by air, under vacuum, by washing with water miscible organic solvents and/or by lyophilization or spray drying.

4. The crystal size and shape is manipulated and controlled in the course of crystallization resulting in a range of crystal morphologies, each having different-dissolution kinetics and subsequently different sustained release profiles compared to amorphous proteins.

5. The mother liquor is removed by centrifugation and the remaining crystalline material is suspended in a pharmaceutically acceptable carrier.

Formulations for Therapeutic Administration

As used herein, a "composition" is understood to mean a mixture comprising at least two components. In particular, compositions are provided comprising a crystalline compound, or prepared using a crystalline compound. In one embodiment, the composition or formulation comprising or prepared using a crystalline compound is prepared such that it is suitable for administration to a patient in need thereof. Compositions to be administered for pharmaceutical purposes to patients are substantially sterile and do not contain any agents that are unduly toxic or infectious to the recipient.

In one embodiment of the invention, crystalline compounds are administered in the form of a physiologically acceptable composition (also referred to herein as a pharmaceutical composition or as a pharmaceutical formulation) comprising a crystalline compound that is formulated with one or more of the following: physiologically acceptable carriers, excipients, or diluents. Such carriers, excipients, or diluents are nontoxic to recipients at the dosages and concentrations employed. Ordinarily, the preparation of such compositions entails combining the crystalline compound with one or more of the following: buffers, antioxidants such as ascorbic acid, low molecular weight polypeptides (such as those having fewer than 10 amino acids), proteins, amino acids, carbohydrates such as glucose, sucrose or dextrins, chelating agents such as EDTA, glutathione and other stabilizers and excipients. In liquid formulations, neutral buffered saline or saline mixed with conspecific serum albumin are exemplary appropriate diluents. In accordance with appropriate industry standards, preservatives may also be added, such as benzyl alcohol. Further examples of components that may be employed in pharmaceutical formulations are presented in Remington's Pharmaceutical Sciences, 16$^{th}$ Ed., Mack Publishing Company, Easton, Pa., 1980, and in the Handbook of Pharmaceutical Excipients, published jointly by the American. Pharmaceutical Association and the Pharmaceutical Society of Great Britain.

In one embodiment, it is contemplated that the formulation of the invention is prepared in a bulk formulation and as such, the components of the pharmaceutical composition are adjusted so that they are higher than would be required for administration, and are diluted appropriately prior to administration. In another aspect, the crystalline compounds are formulated as a solid crystalline or powder formulation in forms suitable for storage and handling, and in forms suitable for inhalation or pulmonary administration, for example in the form of powders for the preparation of aerosol formulations. In a further embodiment, the crystalline compounds are formulated in a liquid solution of such crystals, or in a slurry of such crystals. In another embodiment, the crystalline compounds are used to prepare a liquid formulation, such as an aqueous formulation, for therapeutic administration.

Components of Pharmaceutical Formulations

The present pharmaceutical composition is prepared by combining, in addition to a crystalline compound as described herein, one or more of the following types of ingredients or excipients listed in the paragraphs below, many or all of which are available from commercial suppliers. It will be understood one of ordinary skill in the art that the combining of the various components to be included in the composition can be done in any appropriate order, namely, the buffer can be added first, middle or last and the tonicity modifier can also be added first, middle or last. It is also to be understood by one of ordinary skill in the art that some of these chemicals can be incompatible in certain combination's, and accordingly, are easily substituted with different chemicals that have similar properties but are compatible in the relevant mixture. There is knowledge in the art regarding the suitability of various combinations of excipients and other ingredients or materials present in, for example, the containers used for storage of the pharmaceutical composition and/or the devices used for therapeutic administration (see, for example, Akers, 2002, J Pharm Sci 91: 2283-2300).

Acidifying agents ("acidifying means"): acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid, and other suitable acids.

Active ingredients: additional active ingredients can also be included in the presently described composition, for example, to reduce injection site discomfort. Such active ingredients include, but are not limited to non-steroidal anti-inflammatory drugs such as, for example, tromethamine, in an appropriate dosage.

Aerosol propellants ("propellant means"): butane, dichlorodifluoromethane, dichlorotetrafluoroethane, isobutane, propane, trichloromonofluoromethane.

Aggregation inhibitors ("aggregation inhibiting means") reduce a polypeptide's tendency to associate in inappropriate or unwanted ternary or quaternary complexes. Suitable aggregation inhibitors include the amino acids L-arginine and/or, L-cysteine, which can act to reduce aggregation of polypeptides containing an Fc domain over long periods, e.g., two years or more. The concentration of the aggregation inhibitor in the formulation can be between about 1 mM to 1M, or about 10 mM to about 200 mM, or about 10 mM to about 100 mM, or about 15 mM to about 75 mM, or about 25 mM.

Alcohol denaturants ("denaturant means"): denatonium benzoate, methyl isobutyl ketone, sucrose octacetate.

Alkalizing agents ("alkalizing means"): strong ammonia solution, ammonium carbonate, diethanolamine, diisopropanolamine, potassium hydroxide, sodium bicarbonate, sodium borate, sodium carbonate, sodium hydroxide, trolamine.

Anticaking agents ("anticaking means"): calcium silicate, magnesium silicate, colloidal silicon dioxide, talc.

Antifoaming agents ("antifoaming means"): dimethicone, simethicone.

Antioxidants ("antioxidant means") may be included in the formulations of the present invention. Anti-oxidants contemplated for use in the preparation of the formulations include amino acids such as glycine and lysine, chelating agents such as EDTA and DTPA, and free-radical scavengers such as sorbitol and mannitol. Additional antioxidants include ascorbic acid, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, sodium thiosulfate, sulfur dioxide, tocopherol, and tocopherols excipient. Also contemplated for use in inhibiting oxidation is nitrogen or carbon dioxide overlay. Nitrogen or carbon dioxide overlay can be introduced to the headspace of a vial or prefilled syringe during the filling process.

Buffering agents ("formulation buffering means") maintain the pH of the pharmaceutical formulation in a desired range. When the pH of the pharmaceutical composition is set at or near physiological levels, comfort of the patient upon administration is maximized. In particular, in certain embodiments the pH of a pharmaceutical composition is within a pH range of about 4.0 to 8.4, or a pH range of about 5.0 to 8.0, or a pH range of about 5.8 to 7.4, or about 6.2 to 7.0. It is to be understood that the pH can be adjusted as necessary to maximize stability and solubility of the polypeptide in a particular formulation and as such, a pH outside of physiological ranges, yet tolerable to the patient, is within the scope of the invention. Various buffers suitable for use in the pharmaceutical composition of the invention include histidine, alkali salts (sodium or potassium phosphate or their hydrogen or dihydrogen salts), sodium citrate/citric acid, sodium acetate/ acetic acid, potassium citrate, maleic acid, ammonium acetate, tris-(hydroxymethyl)-aminomethane (tris), various forms of acetate and diethanolamine, ammonium carbonate, ammonium phosphate, boric acid, lactic acid, phosphoric acid, potassium metaphosphate, potassium phosphate monobasic, sodium lactate solution, and any other pharmaceutically acceptable pH buffering agent known in the art. pH-adjusting agents such as hydrochloric-acid, sodium hydroxide, or a salt thereof, may also be included in order to obtain the desired pH. One suitable buffer is sodium phosphate for maintaining pharmaceutical compositions at or near pH 6.2. In another example, acetate is a more efficient buffer at pH 5 than pH 6 so less acetate may be used in a solution at pH 5 than at pH 6. The concentration of the buffer in the formulation can be between about 1 mM to about 1M, or about 10 mM to about 200 mM.

Chelating agents ("chelating means", also called sequestering agents): edetate disodium, ethylenediaminetetraacetic acid and salts, edetic acid.

Coating agents ("coating means"): sodium carboxymethylcellulose, cellulose acetate, cellulose acetate phthalate, ethylcellulose, gelatin, pharmaceutical glaze, hydroxypropyl cellulose, hydroxypropyl methyl cellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein.

Colors ("coloring means"): caramel; erythrosine (FD&C Red No. 3); FD&C Red No. 40; FD&C Yellow No. 5; FD&C Yellow No. 6; FD&C Blue No. 1; red, yellow, black, blue or blends; ferric oxide.

Complexing agents ("complex-forming means"): ethylenediaminetetraacetic acid and salts (EDTA), edetic acid, gentisic acid ethanolamide, oxyquinoline sulfate.

Desiccants ("dessicating means"): calcium chloride, calcium sulfate, silicon dioxide.

Filtering aids ("filtering means"): powdered cellulose, purified siliceous earth.

Flavors and perfumes ("flavoring means"): anethole, anise oil, benzaldehyde, cinnamon oil, cocoa, ethyl vanillin, menthol, methyl salicylate, monosodium glutamate, orange flower oil, orange oil, peppermint, peppermint oil, peppermint spirit, rose oil, stronger rose water, thymol, tolu balsam tincture, vanilla, vanilla tincture, vanillin.

Humectants ("moisture-retaining means"): glycerin, hexylene glycol, propylene glycol, sorbitol.

Ointment bases ("ointment means"): lanolin, anhydrous lanolin, hydrophilic ointment, white ointment, yellow ointment, polyethylene glycol ointment, petrolatum, hydrophilic petrolatum, white petrolatum, rose water ointment, squalane.

Plasticizers ("plasticizing means"): castor oil, diacetylated monoglycerides, diethyl phthalate, glycerin, mono- and diacetylated monoglycerides, polyethylene glycol, propylene glycol, triacetin, triethyl citrate.

Polymer membranes: cellulose acetate.

Polymeric carriers ("carrier means" are polymers used for encapsulation of polypeptide crystals for delivery of polypeptide, including biological delivery. Such polymers include biocompatible and biodegradable polymers. The polymeric carrier may be a single polymer type or it may be composed of a mixture of polymer types. Polymers useful as the polymeric carrier, include for example, poly (acrylic acid), poly (cyanoacrylates), poly (amino acids), poly (anhydrides), poly (depsipeptide), poly (esters) such as poly (lactic acid) or PLA, poly (lactic-co-glycolic acid) or PLGA, poly (B-hydroxybutyrate), poly (caprolactone) and poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, natural and synthetic polypeptides, alginate, cellulose and cellulose derivatives, collagen, fibrin, gelatin, hyaluronic acid, oligosaccharides, glycaminoglycans, sulfated polysaccharides, or any conventional material that will encapsulate polypeptide crystals.

Preservatives (or "preserving means"), such as antimicrobial preservatives, contemplated for use in the formulations of the present invention, such as multi-dose formulations, include benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, and thymol. The amount of preservative included will be in the range of 0% to 2% (w/v) or about 1% (w/v).

Solubilizing agents and stabilizers ("solubilizing means" or "stabilizing means", also referred to as emulsifying agents, co-solutes, or co-solvents) that increase the solubility of the polypeptide and/or stabilize the polypeptide while in solution (or in dried or frozen forms) can also be added to a pharmaceutical composition. Examples of solubilizing and stabilizing agents include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA (HSA), or recombinant HA), dextran, PVA, hydroxypropyl methylcellulose (HPMC), polyethyleneimine, gelatin, polyvinylpyrrolidone (PVP), hydroxyethylcellulose (HEC); non-aqueous solvents such as: polyhydric alcohols (e.g., PEG, ethylene glycol and glycerol), dimethysulfoxide (DMSO), and dimethylformamide (DMF); amino acids such as: proline, L-methionine, L-serine, sodium glutamic acid, alanine, glycine, lysine hydrochloride, sarcosine, and gamma-aminobutyric acid; surfactants such as: Tween-80, Tween-20; SDS, polysorbate, polyoxyethylene copolymer; and miscellaneous stabilizing excipients such as: potassium phosphate, sodium acetate, ammonium sulfate, magnesium sulfate, sodium sulfate, trimethylamine N-oxide, betaine, metal ions (e.g., zinc, copper, calcium, manganese, and magnesium), CHAPS, monolaurate, 2-O-beta-mannoglycerate; or any of the following: acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax; wetting and/or solubilizing agents such as benzalkonium chloride, benzethonium chloride, cetylpyridinium chloride, docusate sodium, nonoxynol 9, nonoxynol 10, octoxynol 9, polyoxyl 50 stearate, tyloxapol; or any combination of the above. The concentration of solubilizers/stabilizers in the formulation can be between about 0.001 to weight percent, or about 0.1 to 2 weight percent. In one embodiment, the stabilizer is selected from sorbitan mono-9-octadecenoate poly(oxy-1,2-ethanediyl) derivatives, including but not limited to, polysorbate 80 or polysorbate 20. The amount of polysorbate 20 or 80 to be used in this embodiment is in the range of 0.001% to 0.1% (w/v), such as 0.005% (w/v), in single use or in multi-dose formulations. In another embodiment, free L-methionine in the range of 0.05 mM to 50 mM is included in the formulation: the amount of free L-methionine is 0.05 mM to 5 mM for single use formulations, and 1 mM to 10 mM for multi-dose formulations.

Solvents ("means for dissolving"): acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water.

Sorbents (also called adsorbents, "adsorbing means"): powdered cellulose, charcoal, purified siliceous earth; and carbon dioxide sorbents: barium hydroxide lime, soda lime.

Stiffening agents ("stiffening means"): hydrogenated castor oil, cetostearyl alcohol, cetyl alcohol, cetyl esters wax, hard fat, paraffin, polyethylene excipient, stearyl alcohol, emulsifying wax, white wax, yellow wax.

Suppository bases ("suppository means"): cocoa butter, hard fat, polyethylene glycol.

Suspending and/or viscosity-increasing agents ("viscosity-increasing means"): acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum.

Sweetening agents ("sweetening means"): aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup.

Tablet binders ("tablet binding means"): acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup.

Tablet and/or capsule diluents ("diluent means"): calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar.

Tablet disintegrants ("tablet disintegrant means"): alginic acid, microcrystalline cellulose, croscarmellose sodium, corspovidone, polacrilin potassium, sodium starch glycolate, starch, pregelatinized starch.

Tablet and/or capsule lubricants ("lubricating means"): calcium stearate, glyceryl behenate, magnesium stearate, light mineral oil, polyethylene glycol, sodium stearyl fumarate, stearic acid, purified stearic acid, talc, hydrogenated vegetable oil, zinc stearate.

Tonicity modifiers ("tonicity modifying-means") are understood to be molecules that contribute to the osmolality of a solution. The osmolality of a pharmaceutical composition is preferably regulated in order to maximize the active ingredient's stability and also to minimize discomfort to the patient upon administration. Serum is approximately 300+/−50 milliosmolals per kilogram. It is generally preferred that a pharmaceutical composition be isotonic with serum, i.e., having the same or similar osmolality, which is achieved by addition of a tonicity modifier, thus it is contemplated that the osmolality will be from about 180 to about 420 milliosmolals, however, it is to be understood that the osmolality can be either higher or lower as specific conditions require. Examples of tonicity modifiers suitable for modifying osmolality include, but are not limited to amino acids (e.g., arginine, cysteine, histidine and glycine), salts (e.g., sodium chloride, potassium chloride and sodium citrate) and/or saccharides (e.g., sucrose, glucose, dextrose, glycerin, and mannitol). The concentration of the tonicity modifier in the formulation can be between about 1 mM to 1M, or about 10 mM to about 200 mM. In one embodiment, the tonicity modifier is sodium chloride within a concentration range of 0 mM to 200 mM. In another embodiment, the tonicity modifier is sorbitol or trehalose and no sodium chloride is present.

Vehicles ("vehicle means"): flavored and/or sweetened (aromatic elixir, compound benzaldehyde elixir, iso-alcoholic elixir, peppermint water, sorbitol solution, syrup, tolu balsam syrup); oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); solid carriers such as sugar spheres; sterile (bacteriostatic water for injection, bacteriostatic sodium chloride injection).

Water-repelling agent ("water-repelling means"): cyclomethicone, dimethicone, simethicone.

In certain embodiments, the pharmaceutical composition comprises a compound selected from the followings or any combination thereof: salts of 1) amino acids such as glycine, arginine, aspartic acid, glutamic acid, lysine, asparagine, glutamine, proline; 2) carbohydrates, e.g. monosaccharides such as glucose, fructose, galactose, mannose, arabinose, xylose, ribose; 3) disaccharides, such as lactose, trehalose, maltose, sucrose; 4) polysaccharides, such as maltodextrins, dextrans, starch, glycogen; 5) alditols, such as mannitol, xylitol, lactitol, sorbitol; 6) glucuronic acid, galacturonic acid; 7) cyclodextrins, such as methyl cyclodextrin, hydroxypropyl-B-cyclodextrin and alike; 8) inorganic salts, such as sodium chloride, potassium chloride, magnesium chloride, phosphates of sodium and potassium, boric acid ammonium carbonate and ammonium phosphate; 9) organic salts, such as acetates, citrate, ascorbate, lactate; 10) emulsifying or solubilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; 11) viscosity increasing reagents like, agar, alginic acid and its salts, guar gum, pectin, polyvinyl alcohol, polyethylene oxide, cellulose and its derivatives propylene carbonate, polyethylene glycol, hexylene glycol, tyloxapol; and 12) particular ingredients such as sucrose, trehalose, lactose, sorbitol, lactitol, inositol, salts of sodium and potassium such as acetate, phosphates, citrates, borate, glycine, arginine, polyethylene oxide, polyvinyl alcohol, polyethylene glycol, hexylene glycol, methoxy polyethylene glycol, gelatin, hydroxypropyl-β-cyclodextrin.

Solid Crystalline Formulations

Solid formulations of crystalline compounds are suited for pulmonary administration, which is useful for biological macromolecules which are difficult to deliver by other routes of administration. (See, for example, PCT patent applications WO 96/32152, WO 95/24183 and WO 97/41833).

Solid formulations include crystals that have been substantially isolated from liquid solution or dried, and are present as free crystals or as particles in for example powder form. In the present context the expression "powder" refers to a collection of essentially dry particles, i.e. the moisture content being below about 10% by weight, or below 6% by weight, or below 4% by weight. In one embodiment the invention provides a method for aerosolizing a dose of crystalline compound comprising providing the crystalline compound as a dry powder, dispersing an amount of the dry powder in a gas stream to form an aerosol, and capturing the aerosol in a chamber for subsequent inhalation.

Crystalline compounds or powders are optionally combined with carriers or surfactants. Suitable carrier agents include 1) carbohydrates, e.g. monosaccharides such as fructose, galactose, glucose, sorbose, and the like; 2) disaccharides, such as lactose, trehalose and the like; 3) polysaccharides, such as raffinose, maltodextrins, dextrans, and the like; 4) alditols, such as mannitol, xylitol, and the like; 5) inorganic salts, such as sodium chloride, and the like; and 6) organic salts, such as sodium citrate, sodium ascorbate, and the like. In certain embodiments, the carrier is selected from the group consisting of trehalose, raffinose, mannitol, sorbitol, xylitol, inositol, sucrose, sodium chloride, and sodium citrate. In one aspect, surfactants are selected from the group consisting of salts of fatty acids, bile salts or phospholipids. Fatty acids salts include salts of $C_{10-14}$ fatty acids, such as sodium caprate, sodium laurate, and sodium myristate. Bile salts include salts of ursodeoxycholate, taurocholate, glycocholate, and taurodihydrdfusidate. In one embodiment, the surfactant is a salt of taurocholate such as sodium taurocholate. Phospholipids surfactants include lysophosphatidylcholine. The molar ratio of crystalline polypeptide to surfactant in a powder formulation of the present invention is for example 9:1 to 1:9, or between 5:1 to 1:5, or between 3:1 to 1:3.

Crystals in Solution or Slurries

In one embodiment, the invention provides a method for rendering peptide crystals suitable for storage in suspensions comprising replacing the crystallization buffer (the mother liquor) with a non-aqueous solvent. In yet another embodiment, the crystalline slurry is rendered solid by spinning out the first solvent and washing the remaining crystalline solid using a second organic solvent or additive to remove water, followed by evaporation of the non-aqueous solvent. Non-aqueous slurries of crystalline therapeutic peptides are useful for subcutaneous delivery.

In one such embodiment, the peptide crystals of the invention are combined with liquid organic additives with the object of stabilizing the peptide crystals. Such a mixture can be characterized as an aqueous-organic mixture that comprises n % organic additive, where n is between 1 and 99 and m % aqueous solution, where m is 100−n. Examples of organic additives include phenolic compounds, such as m-cresol or phenol or a mixture thereof, and acetone, methyl alcohol, methyl isobutyl ketone, chloroform, 1-propanol, isopropanol, 2-propanol, acetonitrile, 1-butanol, 2-butanol, ethyl alcohol, cyclohexane, dioxane, ethyl acetate, dimethylformamide, dichloroethane, hexane, isooctane, methylene chloride, tert-butyl alcohol, toluene, carbon tetrachloride, or combinations thereof.

Liquid Formulations

One embodiment of the present invention is directed to an aqueous formulation that allows for stable long-term storage of a pharmaceutical composition wherein a crystalline compound is the active ingredient used in the preparation of the pharmaceutical composition. This formulation is useful, in part, because it is more convenient to use for the patient, as this formulation does not require any extra steps such as rehydrating. As used herein, a solution or liquid formulation is meant to mean a liquid preparation that contains one or more chemical substances dissolved in a suitable solvent or mixture of mutually miscible solvents.

Reconstitution is the dissolution of peptide crystals or crystal formulations or compositions in an appropriate buffer or pharmaceutical formulation.

Sustained-Release Forms

In one preferred embodiment of the invention, sustained-release forms (also called "controlled-release" forms) of crystalline compounds are used including sustained- or controlled-release forms comprise crystalline compounds and a substance (the "sustained-release means") for extending the physical release or biological availability of the crystalline compound over a desired period of time. Sustained-release forms suitable for use in the disclosed methods include, but are not limited to, crystalline compounds that are encapsulated in sustained-release means such as a slowly-dissolving biocompatible polymer (for example, the polymeric carriers described herein, the alginate microparticles described in U.S. Pat. No. 6,036,978, or the polyethylene-vinyl acetate and poly(lactic-glucolic acid) compositions described in U.S. Pat. No. 6,083,534), admixed with such a polymer (including topically applied hydrogels), and or encased in a biocompatible semi-permeable implant. Further embodiments of the invention include additional sustained-release forms such as polymeric microparticles, wherein a mixture of the active ingredient and sustained-release means such as polymers (for example, PLGA) are dispersed within a continuous phase, and the resulting dispersion is directly lyophilized to remove water and organic solvents or additives and form said microparticles (U.S. Pat. No. 6,020,004); injectable gel compositions-comprising a biodegradable anionic polysaccharide such as an alginate ester, a polypeptide, and at least one bound polyvalent metal ion (U.S. Pat. No. 6,432,449); injectable biodegradable polymeric matrices having reverse thermal gelation properties and optionally pH-responsive gelation/ de-gelation properties (U.S. Pat. Nos. 6,541,033 and 6,451, 346); biocompatible polyol:oil suspensions, such as those wherein the suspension comprises polyol in the range of from about 15% to about 30% by weight (U.S. Pat. No. 6,245,740). Such sustained release forms are suitable for continuous delivery of crystalline compounds through administration in the form of a depot, wherein the depot can be an implant, or can be in the form of injectable microspheres, nanospheres, or gels. The above listed U.S. patents (U.S. Pat. Nos. 6,036,978; 6,083,534; 6,020,004; 6,432,449; 6,541,033; 6,451,346, and 6,245,740) are incorporated in their entirety by reference herein. In addition, sustained- or controlled-release forms of crystalline compounds of the invention comprise types of sustained release means such as those described in Kim, C., 2000, "Controlled Release Dosage Form Design", Techonomic Publishing Co., Lancaster Pa., which include the following: natural polymers (gelatin, sodium alginic acid, xanthan gum, arabic gum, or chitosan), semi-synthetic polymers or cellulose derivatives (methylcellulose, ethylcellulose, hydroxyethylcellulose, hydroxypropylcellulose, hydroxyethylmethylcellulose, hydroxypropylmethylcellulose, sodium carboxymethylcellulose, cellulose acetate, cellulose acetate butyrate, cellulose acetate proprionate, cellulose acetatephthalate, or hydroxypropylmethylcellulose phthalate), and synthetic polymers (ion exchange resins (methacrylic acid, sulfonated polystyrene/divinylbenzene), polyacrylic acid (Carbopol), poly(MMA/MAA), poly (MMA/DEAMA), poly(MMA/EA), poly(vinylacetate phthalate), poly(vinyl alcohol), poly(vinyl pyrrolidone), poly (lactic acid), poly(glycolic acid), poly(lactic/glycolic acid), polyethylene glycol, polyethylene oxide, poly(dimethyl silicone), poly(hydroxyethyl methacrylate), poly(ethylene/vinyl acetate), poly(ethylene/vinyl alcohol), polybutadiene, poly (anhydride), poly(orthoester), and poly(glutamic acid)).

Further embodiments of the invention include crystalline compounds encapsulated in at least one polymeric carrier to form microspheres by virtue of encapsulation within the matrix of the polymeric carrier to preserve their native and biologically active tertiary structure, as described in U.S. Pat. No. 6,541,606, which is incorporated in its entirety by reference herein. Crystalline compounds or formulations thereof to be encapsulated are suspended in a polymeric carrier such as PLGA which is dissolved in an organic solvent or additive. Such encapsulated crystalline compounds maintain the biological activity of the peptide for a longer period of time than a peptides in solution when stored under comparable conditions.

Testing Formulations for Polypeptide Stability and Biological Activity

In yet another embodiment, the invention provides a method for accelerated stability testing of the stability of a crystalline compound in a pharmaceutical composition of the invention comprising the steps of testing the activity of the peptide formulated according to the invention prior to storage, i.e., time zero; storing the composition at 37° C. for one month and measuring the stability of the polypeptide; and comparing the stability form time zero to the one month time point. This information is helpful for early elimination of batches or lots that appear to have good stability initially, yet do not store well for longer periods.

Moreover, the present pharmaceutical composition provides improved long-term storage such that the active crystalline compound is stable over the course of storage either in liquid or frozen states. As used herein, the phrase "long-term" storage is understood to mean that the pharmaceutical composition can be stored for three months or more, for six months or more, and preferably for one year or more. Long term storage is also understood to mean that the pharmaceutical composition is stored either as a liquid at 2-8° C. or is frozen, e.g., at −20° C. or colder. It is also contemplated that the composition can be frozen and thawed more than once. The term "stable" with respect to long-term storage is understood to mean that the active polypeptide of the pharmaceutical composition does not lose more than 20%, or more preferably 15%, or even more preferably 10%, and most preferably 5% of its activity relative to activity of the composition at the beginning of storage. Activity of the peptide can be assayed by any one of a number of assays, including ligand-binding assays such as ELISA assays, where ligand, for example c-Mpl, is bound to a solid support, test and control preparations of peptides are added, and binding of the peptide to the ligand is detected using labeled anti-Ig antibodies directed to the Fc domain of the peptide.

Administration and Dosing

As used herein, "administration of crystalline compound" or "administration of crystalline peptides" means the administration of a pharmaceutical composition comprising a crystalline compound or prepared using a crystalline compound.

The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors.

The crystalline compounds may be administered by an initial bolus followed by a continuous infusion to maintain therapeutic circulating levels of drug product. As another example, the crystalline compound may be administered as a one-time dose. Those of ordinary skill in the art will readily optimize effective dosages and administration regimens as determined by good medical practice and the clinical condition of the individual patient. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (I 990, Mack Publishing Co., Easton, Pa. 18042) pages 1435-

1712, the disclosure of which is hereby incorporated by reference. Such formulations may influence the physical state, stability, rate of in vivo release, and rate of in vivo clearance of the administered agents. Depending on the route of administration, a suitable dose may be calculated according to body weight, body surface area or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in the human clinical trials discussed above. Appropriate dosages may be ascertained through use of established assays for determining blood levels dosages in conjunction with appropriate dose-response data. The final dosage regimen will be determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels and duration of treatment for various diseases and conditions.

Any efficacious route of administration may be used to therapeutically administer the crystalline compound. Appropriate dosages are determined in standard dosing trials, and may vary according to the chosen route of administration. If injected, the crystalline compound is administered, for example, via intra-articular, intravenous, intramuscular, intralesional, intraperitoneal, or subcutaneous routes by bolus injection or by continuous infusion. Other suitable means of administration include sustained release from implants, depots (implanted or injected), suppositories, aerosol inhalation, eyedrops, oral preparations, including pills, syrups, lozenges, or chewing gum, and topical preparations such as lotions, gels, sprays, ointments, or other suitable techniques. When a crystalline compound is administered in combination with one or more other biologically active compounds, in one aspect these are administered by the same or by different routes, and are administered simultaneously, separately, or sequentially.

In the following exemplary and non-limiting dosing regimens, the amount of crystalline compound administered is understood to be the amount of crystalline compound for pharmaceutical compositions comprising crystalline compounds, or the amount of peptide for pharmaceutical compositions prepared using crystalline peptide.

In one embodiment of the invention, a crystalline compound is administered one time per week to treat a medical disorder or condition disclosed herein, in another embodiment is administered at least two times per week, and in another embodiment is administered at least three times per week. An adult patient is a person who is 18 years of age or older. If injected, the effective amount of the crystalline compound per adult dose ranges from 1-20 mg/m$^2$ of body surface area, and preferably is about 5-12 mg/m$^2$. Alternatively, a flat dose is administered in a range from 5-100 mg/dose. Exemplary dose ranges for a flat dose to be administered by subcutaneous injection are 5-25 mg/dose, 25-50 mg/dose, and 50-100 mg/dose. In one embodiment of the invention, the various indications described below are treated by administering a preparation acceptable for injection containing or prepared from crystalline compound at 25 mg peptide per dose, or alternatively, containing 50 mg per dose. The 25 mg or 50 mg dose may be administered repeatedly, particularly for chronic conditions. If a route of administration other than injection is used, the dose is appropriately adjusted in accord with standard medical practices. In many instances, an improvement in a patient's condition will be obtained by injecting a dose of about 25 mg of crystalline compound one to three times per week over a period of at least three weeks, or a dose of 50 mg of crystalline compound one or two times per week for at least three weeks, though treatment for longer periods may be necessary to induce the desired degree of improvement. For incurable chronic conditions, the regimen may be continued indefinitely, with adjustments being made to dose and frequency if such are deemed necessary by the patient's physician.

For pediatric patients (age 4-17), a suitable regimen involves the subcutaneous injection of 0.4 mg/kg of body weight, up to a maximum of 25 mg per dose of crystalline compound, administered by subcutaneous injection one or more times per week.

In addition to human patients, crystalline compounds are useful in the treatment of medical conditions as described herein afflicting non-human animals, such as pets (dogs, cats, birds, primates, etc.), domestic farm animals (horses cattle, sheep, pigs, birds, etc.), or any animal that suffers from a condition comparable to one of the conditions described herein. In such instances, an appropriate dose may be determined according to the animal's body weight. For example, a dose of 0.2-1 mg/kg may be used. Alternatively, the dose is determined according to the animal's surface area, an exemplary dose ranging from 0.1-20 mg/m$^2$ of body surface area, or more preferably, from 5-12 mg/m$^2$ of body surface area. For small animals, such as dogs or cats, a suitable dose is 0.4 mg/kg of body weight. In another embodiment, A crystalline compound is administered by injection or other suitable route one or more times per week until the animal's condition is improved, or it may be administered indefinitely.

Combination Therapy

The invention further includes the administration of a crystalline compound concurrently with one or more other drugs that are administered to the same patient in combination with the pharmaceutical composition comprising the crystalline compound, or prepared using a crystalline compound, each drug being administered according to a regimen suitable for that medicament. "Concurrent administration" encompasses simultaneous or sequential treatment with the components of the combination, as well as regimens in which the drugs are alternated, or wherein one component is administered long-term and the other(s) are administered intermittently. Components may be administered in the same or in separate compositions, and by the same or different routes of administration.

Thus, therapeutic methods, compositions and crystalline compounds are also employed, alone or in combination with other cytokines, soluble mpl receptor, hematopoietic factors, interleukins, growth factors or antibodies in the treatment of disease states characterized by other symptoms as well as platelet deficiencies. For example, it is anticipated that the crystalline compounds are useful in treating some forms of thrombocytopenia in combination with general stimulators of hematopoiesis, such as IL-3 or GM-CSF. Other megakaryocytic stimulatory factors, i.e., meg-CSF, stem cell factor (SCF), leukemia inhibitory factor (LIF), oncostatin M (OSM), or other molecules with megakaryocyte stimulating activity may also be employed with mpl ligand.

Additional exemplary cytokines or hematopoietic factors for such co-administration include IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1., bone morphogenic protein-2, bone morphogenic protein-3, bone morphogenic protein-4, bone morphogenic protein-5, bone morphogenic protein-6, bone morphogenic protein-7; bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2, cytokine-induced neutrophil chemotactic factor 2, endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor 1, glial cell line-derived neutrophic factor receptor 2, growth related protein, growth related protein, growth related protein, growth related protein, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor, platelet derived growth factor receptor, pre-B cell growth stimulating factor, stem cell factor receptor, TNF, including TNF0, TNF1, TNF2, transforming growth factor, transforming growth factor, transforming growth factor 1, transforming growth factor 1.2, transforming growth factor 2, transforming growth factor 3, transforming growth factor 5, latent transforming growth factor 1, transforming growth factor binding protein I, transforming growth factor binding protein II, transforming growth factor binding protein III, tumor necrosis factor receptor type I, tumor necrosis factor receptor type II, urokinase-type plasminogen activator receptor, vascular endothelial growth factor, and chimeric proteins and biologically or immunologically active fragments thereof. It may further be useful to administer, either simultaneously or sequentially, an effective amount of a soluble mammalian c-Mpl receptor, which appears to have an effect of causing megakaryocytes to fragment into platelets once the megakaryocytes have reached mature form. Thus, administration of a crystalline compound (to enhance the number of mature megakaryocytes) followed by administration of the soluble c-Mpl receptor (to inactivate the ligand and allow the mature megakaryocytes to produce platelets) is expected to be a particularly effective means of stimulating platelet production. The dosage recited above would be adjusted to compensate for such additional components in the therapeutic composition. Progress of the treated patient can be monitored by conventional methods.

Uses of the Compounds

The crystalline compounds described herein have the ability to bind to and/or activate the c-Mpl receptor, and/or have the ability to stimulate the production (both in vivo and in vitro) of platelets ("thrombopoietic activity") and platelet precursors ("megakaryocytopoietic activity"). To measure the activity (-ies) of these compounds, one can utilize standard assays, such as those described in WO95/26746.

The conditions to be treated by the methods and compositions of the present invention are generally those which involve an existing megakaryocyte/platelet deficiency or an expected or anticipated megakaryocyte/platelet deficiency in the future (e.g., because of planned surgery or platelet donation). Such conditions may be the result of a deficiency (temporary or permanent) of active c-Mpl ligand in vivo. The generic term for platelet deficiency is thrombocytopenia, and hence the methods and compositions of the present invention are generally available for prophylactically or therapeutically treating thrombocytopenia in patients in need thereof.

The World Health Organization has classified the degree of thrombocytopenia on the number of circulating platelets in the individual (Miller, et al., Cancer 47:210-211 (1981)). For example, an individual showing no signs of thrombocytopenia (Grade 0) will generally have at least 100,000 platelets/$mm^3$. Mild thrombocytopenia (Grade 1) indicates a circulating level of platelets between 79,000 and 99,000/$mm^3$. Moderate thrombocytopenia (Grade 2) shows between 50,000 and 74,000 platelets/$mm^3$ and severe thrombocytopenia is characterized by between 25,000 and 49,000 platelets/$mm^3$. Life-threatening or debilitating thrombocytopenia is characterized by a circulating concentration of platelets of less than 25,000/$mm^3$.

Thrombocytopenia (platelet deficiencies) may be present for various reasons, including chemotherapy and other therapy with a variety of drugs, radiation therapy, surgery, accidental blood loss, and other specific disease conditions. Exemplary specific disease conditions that involve thrombocytopenia and may be treated in accordance with this invention are: aplastic anemia; idiopathic or immune thrombocytopenia (ITP), including idiopathic thrombocytopenic purpura associated with breast cancer; HIV associated ITP and HIV-related thrombotic thrombocytopenic purpura; metastatic tumors which result in thrombocytopenia; systemic lupus erythematosus; including neonatal lupus syndrome splenomegaly; Fanconi's syndrome; vitamin B12 deficiency; folic acid deficiency; May-Hegglin anomaly; Wiskott-Aldrich syndrome; chronic liver disease; myelodysplastic syndrome associated with thrombocytopenia; paroxysmal nocturnal hemoglobinuria; acute profound thrombocytopenia following C7E3 Fab (Abciximab) therapy; alloimmune thrombocytopenia, including maternal alloimmune thrombocytopenia; thrombocytopenia associated with antiphospholipid antibodies and thrombosis; autoimmune thrombocytopenia; drug-induced immune thrombocytopenia, including carboplatin-induced thrombocytopenia, heparin-induced thrombocytopenia; fetal thrombocytopenia; gestational thrombocytopenia; Hughes' syndrome; lupoid thrombocytopenia; accidental and/or massive blood loss; myeloproliferative disorders; thrombocytopenia in patients with malignancies; thrombotic thrombocytopenia purpura, including thrombotic microangiopathy manifesting as thrombotic thrombocytopenic purpura/hemolytic uremic syndrome in cancer patients; autoimmune hemolytic anemia; occult jejunal diverticulum perforation; pure red cell aplasia; autoimmune thrombocytopenia; nephropathia epidemica; rifampicin-associated acute renal failure; Paris-Trousseau thrombocytopenia; neonatal alloimmune thrombocytopenia; paroxysmal nocturnal hemoglobinuria; hematologic changes in stomach cancer; hemolytic uremic syndromes in childhood; hematologic manifestations related to viral infection including hepatitis A virus and CMV-associated thrombocytopenia. Also, certain treatments for AIDS result in thrombocytopenia (e.g., AZT). Certain wound healing disorders might also benefit from an increase in platelet numbers.

With regard to anticipated platelet deficiencies, e.g., due to future surgery, a compound of the present invention could be administered several days to several hours prior to the need for platelets. With regard to acute situations, e.g., accidental and massive blood loss, a compound of this invention could be administered along with blood or purified platelets.

The crystalline compounds are also useful in stimulating certain cell types other than megakaryocytes if such cells are found to express c-Mpl receptor. Conditions associated with such cells that express the c-Mpl receptor, which are responsive to stimulation by the c-Mpl ligands, are also within the scope of this invention.

The crystalline compounds are also used in any situation in which production of platelets or platelet precursor cells is desired, or in which stimulation of the c-Mpl receptor is desired. Thus, for example, the crystalline compounds are used to treat any condition in a mammal wherein there is a need of platelets, megakaryocytes, and the like. Such conditions are described in detail in the following exemplary sources: WO95/26746; WO95/21919; WO95/18858; WO95/21920 and are incorporated herein.

The crystalline compounds are also useful in maintaining the viability or storage life of platelets and/or megakaryocytes and related cells. Accordingly, it could be useful to include an effective amount of one or more such crystalline compounds in a composition containing such cells. In cases where the crystalline compounds are added to compositions of platelets and/or megakaryocytes and related cells, the amount to be included will generally be ascertained experimentally by techniques and assays known in the art. An exemplary range of amounts is 0.1 µg-1 mg crystalline compound per $10^6$ cells.

EXAMPLES

Example 1

Screening of Crystallization Conditions

Initial screening of crystallization conditions was carried out using a bulk preparation of a peptide described herein with commercially available sparse-matrix and random screens (Hampton Research and Emerald BioSystems). Additional screening was performed around initial conditions that produced crystals or crystalline forms. Peptide concentrations were 10-20 mg/ml for the screening experiments.

Initial screens that produced crystals or crystal forms after one day at room temperature:

| | | |
|---|---|---|
| 1. | P1 #1 | 0.2M sodium fluoride, 20% w/v PEG 3350, pH 7.1 |
| 2. | P1 #2 | 0.2M potassium fluoride, 20% w/v PEG 3350, pH 7.2 |
| 3. | P1 #3 | 0.2M ammonium fluoride, 20% w/v PEG 3350, pH 6.2 |
| 4. | P1 #4 | 0.2M lithium chloride anhydrous, 20% w/v PEG 3350, pH 6.7 |
| 5. | P1 #4 | 0.2M potassium formate, 20% w/v PEG 3350, pH 7.3 |
| 6. | P1 #22 | 0.2M lithium acetate dihydrate, 20% w/v PEG 3350, pH 7.8 |
| 7. | P1 #24 | 0.2M sodium acetate trihydrate, 20% w/v PEG 3350, pH 7.9 |
| 8. | P1 #27 | 0.2M calcium acetate hydrate, 20% w/v PEG 3350, pH 7.3 |
| 9. | P1 #28 | 0.2M potassium acetate, 20% w/v PEG 3350, pH 7.8 |
| 10. | P1 #29 | 0.2M ammonium acetate, 20% w/v PEG 3350, pH 7.1 |
| 11. | P1 #30 | 0.2M di-ammonium hydrogen phosphate, 20% w/v PEG 3350, pH 7.9 |
| 12. | P1 #44 | 0.2M tri-lithium citrate tetrahydrate, 20% w/v PEG 3350, pH 8.1 |
| 13. | P1 #46 | 0.2M tri-sodium citrate dihydrate, 20% w/v PEG 3350, pH 8.2 |
| 14. | P1 #47 | 0.2M tri-potassium citrate monohydrate, 20% w/v PEG 3350, pH 8.3 |
| 15. | P1 #48 | 0.2M di-ammonium hydrogen citrate, 20% w/v PEG 3350, pH 5.0 |

Initial screens that produced crystals or crystal forms after two days at room temperature:

| | | |
|---|---|---|
| 1. | CSI #2 | 0.4M potassium sodium tartrate |
| 2. | CSI #25 | 0.1M imidazole pH 6.5, 1M sodium acetate |
| 3. | CSI #34 | 0.1M sodium acetate pH 4.6, 2M sodium formate |
| 4. | CSI #35 | 0.1M sodium HEPES pH 7.5, 0.8M sodium di-hydrogen phosphate, 0.8M potassium di-hydrogen phosphate |
| 5. | CSII #2 | 0.5M sodium chloride, 0.01M magnesium chloride heahydrate, 0.01M hexadecyltrimetyl ammonium bromide |
| 6. | CSII #16 | 0.5M sodium chloride, 0.1M tri-sodium citrate pH 5.6, 2% v/v ethylene imine polymer |
| 7. | CSII #22 | 0.1M MES pH 6.5, 12% w/v PEG 20,000 |
| 8. | CSII #23 | 1.6M ammonium sulfate, 0.1M MES pH 6.5, 10% v/v dioxane |

Subsequent experiments centered around expansions of a few of the most promising conditions:

| | |
|---|---|
| CSII #22 | 0.1M MES pH 6.5, 12% w/v PEG 20,000; resulting in crystals forming in conditions spanning 0.1M MES pH 5.8-7.1 |
| CSII #23 | 1.6M ammonium sulfate, 0.1M MES pH 6.5, 10% v/v dioxane |
| CSI #34 | 0.1M sodium acetate pH 4.6, 2M sodium formate |
| CSI #35 | 0.1M sodium HEPES pH 7.5, 0.8M sodium di-hydrogen phosphate, 0.8M potassium di-hydrogen phosphate |

Additional commercially available sparse matrix and random screens produced additional crystals or crystalline forms at room temperature.

| | |
|---|---|
| PSS 100% #25 | 15% isopropanol, 1M (NH4)3 citrate/ammonium hydroxide pH 8.5 |
| PSS 100% #33 | 30% isopropanol, 10% PEG 1500, 0.2M lithium sulfate, 0.1M acetate pH 5.5 |
| PSS 100% #34 | 40% isopropanol, 15% PEG 8000, 0.1M imidazole pH 6.5 |
| PSS 100% #41 | 25% PEG 400, 20% PEG 3350, 0.1M MgCl2, 0.1M Tris base pH 8.5 |
| PSS 100% #49 | 25% PEG 3350, 4% isopropanol, 0.1M CaCl2, 0.1M HEPES pH 7.5 |
| PSS 100% #51 | 20% PEG 8000, 3% MPD, 0.1M imidazole pH 6.5 |
| PSS 100% #52 | 20% PEG 8000, 10% isopropanol, 0.2M ammonium sulfate, 0.1M HEPES pH 7.5 |
| PSS 100% #60 | 0.5% PEG 4000, 1M k2H phosphate/NaH2 phosphate pH 7.5 |
| PSS 100% #64 | 15% PEG 8000, 0.5M (NH4)3 citrate/ammonium hydroxide pH 8.5 |
| PSS 67% #21 | 1.005M ammonium sulfate, 8.04% isopropanol, 0.1M imidazole pH 6.5 |
| PSS 67% #35 | 13.4% isopropanol, 10.05% PEG 3350, 0.2M (NH4)3 citrate/citric acid pH 7.5 |
| PSS 67% #36 | 20.1% isopropanol, 20.1% PEG 3350, 0.1M Tris base pH 8.5 |
| PSS 67% #38 | 26.8% PEG 400, 3.35% PEG 3350, 0.1M acetate pH 5.5 |
| PSS 67% #39 | 26.8% PEG 400, 10.05% PEG 1000, 0.15M K2H phosphate/NaH2 phosphate pH 6.5 |
| PSS 67% #41 | 16.75% PEG 400, 13.4% PEG 3350, 0.1M mgCl2, 0.1M Tris base |
| PSS 67% #42 | 20.1% PEG 1500, 2.01% MPD, 0.2M MgSO4, 0.1M acetate pH 5.5 |
| PSS 67% #47 | 16.75% PEG 3350, 3.35% PEG 400, 0.1M acetate pH 5.5 |
| PSS 67% #48 | 16.75% PEG 3350, 10.05% MPD, 0.2M lithium sulfate, 0.1M imidazole pH 6.5 |
| PSS 67% #49 | 16.75% PEG 3350, 2.68% isopropanol, 0.1M CaCl2, 0.1M HEPES pH 7.5 |
| PSS 67% #51 | 13.4% PEG 8000, 6.7% isopropanol, 0.2M ammonium sulfate, 0.1M HEPES pH7.5 |
| PSS 67% #53 | 13.4% PEG 8000, 13.4% PEG 400, 0.1M MgCl2, 0.1M Tris pH 8.5 |
| PSS 67% #60 | 0.34% PEG 4000, 0.67M K2H psophate/NaH2 phosphate |
| PSS 33% #3 | 0.66M ammonium sulfate, 0.33% MPD, 0.1M HEPES pH 7.5 |
| PSS 33% #4 | 0.66M ammonium sulfate, 1.65% PEG 4000, 1M MgSO4, 0.1M Tris pH 8.5 |
| PSS 33% #5 | 1.287M NaCl, 0.66% PEG 400, 0.1M MgCl2, 0.1M acetate pH 5.5 |
| PSS 33% #6 | 0.99M NaCl, 1.65% MPD, 0.1M CaCl2, 0.1M imidazole pH 6.5 |
| PSS 33% #7 | 1.32M NaCl, 1.65% isopropanol, 0.1M HEPES pH 7.5 |
| PSS 33% #10 | 6.6% glycerol, 0.825M K2H phosphate/NaH2 phosphate pH 7.5 |
| PSS 33% #23 | 1.32M NaCl, 3.3% PEG 400, 0.1M HEPES pH 7.5 |
| PSS 33% #25 | 4.95% isopropanol, 0.33M (NH4)3 citrate/ammonium hydroxide pH 8.5 |
| PSS 33% #34 | 13.2% isopropanol, 4.95% PEG 8000, 0.1M imidazole pH 6.5 |
| PSS 33% #35 | 6.6% isopropanol, 4.95% PEG 3350, 0.2M (NH4)3 citrate/citric acid pH 7.5 |
| PSS 33% #36 | 9.9% isopropanol, 9.9% PEG 3350, 0.1M Tris pH 8.5 |
| PSS 33% #39 | 13.2% PEG 400, 4.95% PEG 1000, 0.15M K2H phosphate/NaH2 phosphate pH 6.5 |
| PSS 33% #41 | 8.25% PEG 400, 6.6% PEG 3350, 0.1M MgCl2, 0.1M Tris pH 8.5 |
| PSS 33% #43 | 9.9% PEG 1500, 3.3% isopropanol, 0.1M CaCl2, 0.1M HEPES pH 7.5 |
| PSS 33% #45 | 9.9% PEG 1500, 2.64% MPD, 0.1M Tris base pH 8.5 |
| PSS 33% #49 | 8.25% PEG 3350, 1.32% isopropanol, 0.1M CaCl2, 0.1M HEPES pH 7.5 |
| PSS 33% #50 | 6.6% PEG 8000, 3.3% PEG 400, 0.5M NaCl, 0.1M acetate pH 5.5 |
| PSS 33% #51 | 6.6% PEG 8000, 0.99% MPD, 0.1M imidazole pH 6.5 |
| PSS 33% #52 | 6.6% PEG 8000, 3.3% isopropanol, 0.2M ammonium sulfate, 0.5M HEPES pH 7.5 |
| PSS 33% #54 | 0.693M Na formate, 8.25% PEG 3350, 0.1M CaCl2, 0.1M acetate pH 4.5 |
| PSS 33% #57 | 0.825M NaCl, 3.96% PEG 1500, 0.495% MPD, 0.1M acetate pH 5.5 |
| PSS 33% #58 | 0.66M NaCl, 6.6% PEG 3350, 0.1M MgCl2, 0.1M imidazole pH 6.5 |
| PSS 33% #59 | 0.99M Na formate, 1.32% PEG 8000, 0.1M imidazole pH 6.5 |
| PSS 33% #61 | 3.3% PEG 3350, 0.462M K2H phosphate/NaH2 phosphate pH 7.5 |
| PSS 33% #64 | 4.95% PEG 8000, 0.165M (NH4)3 citrate/ammonium hydroxide pH 8.5 |

Additional commercially available sparse matrix and random screens produced additional crystals or crystalline forms at 15° C.

| | |
|---|---|
| PSS 100% #25 | 15% isopropanol, 1M (NH4)3 citrate/ammonium hydroxide pH 8.5 |
| PSS 100% #33 | 30% isopropanol, 10% PEG 1500, 0.2M lithium sulfate, 0.1M acetate pH 5.5 |
| PSS 100% #34 | 40% isopropanol, 15% PEG 8000, 0.1M imidazole pH 6.5 |
| PSS 100% #47 | 25% PEG 3350, 5% PEG 400, 0.1M acetate pH 5.5 |
| PSS 67% #2 | 1.34M ammonium sulfate, 6.7% glycerol, 0.1M MgSO4, 0.1M imidazole pH 6.5 |
| PSS 67% #16 | 1.34M lithium sulfate, 3.35% PEG 400, 0.1M MgSO4, 0.1M acetate pH 5.5 |

-continued

| | |
|---|---|
| PSS 67% #35 | 13.4% isopropanol, 10.05% PEG 3350, 0.2M (NH4)3 citrate/citric acid pH 7.5 |
| PSS 67% #38 | 26.8% PEG 400, 3.35% PEG 3350, 0.1M acetate pH 5.5 |
| PSS 67% #39 | 26.8% PEG 400, 10.05% PEG 1000, 0.15M K2H phosphate/NaH2 phosphate pH 6.5 |
| PSS 67% #41 | 16.75% PEG 400, 13.4% PEG 3350, 0.1M MgCl2, 0.1M Tris base |
| PSS 67% #48 | 16.75% PEG 3350, 10.05% MPD, 0.2M lithium sulfate, 0.1M imidazole pH 6.5 |
| PSS 67% #49 | 16.75% PEG 3350, 2.68% isopropanol, 0.1M CaCl2, 0.1M HEPES pH 7.5 |
| PSS 67% #52 | 13.4% PEG 8000, 6.7% isopropanol, 0.2M ammonium sulfate, 0.1M HEPES pH 7.5 |
| PSS 67% #53 | 13.4% PEG 8000, 13.4% PEG 400, 0.1M MgCl2, 0.1M Tris pH 8.5 |
| PSS 67% #59 | 2.01M Na formate, 2.68% PEG 8000, 0.1M imidazole pH 6.5 |
| PSS 67% #64 | 10.05% PEG 8000, 0.335M (NH4)3 citrate/ammonium hydroxide pH 8.5 |
| PSS 33% #2 | 0.66M ammonium sulfate, 3.3% glycerol, 0.1M MgSO4, 0.1M imidazole pH 6.5 |
| PSS 33% #3 | 0.66M ammonium sulfate, 0.33% MPD, 0.1M HEPES pH 7.5 |
| PSS 33% #5 | 1.287M NaCl, 0.66% PEG 400, 0.1M MgCl2, 0.1M acetate pH 5.5 |
| PSS 33% #7 | 1.32M NaCl, 1.65% isopropanol, 0.1M HEPES pH 7.5 |
| PSS 33% #8 | 1.65% isopropanol, 0.825M K2H phosphate/NaH2 phosphate pH 6.5 |
| PSS 33% #9 | 0.66% PEG 400, 0.66M H2H phosphate/NaH2 phosphate pH 5.5 |
| PSS 33% #10 | 6.6% glycerol, 0.825M K2H phosphate/NaH2 phosphate pH 7.5 |
| PSS 33% #13 | 1.65% isopropanol, 0.66M (NH4)3 citrate/citric acid pH 6.5 |
| PSS 33% #14 | 1.65% PEG 400, 0.66M (NH4)3 citrate/citric acid pH 6.5 |
| PSS 33% #23 | 1.32M NaCl, 3.3% PEG 400, 0.1M HEPES pH 7.5 |
| PSS 33% #26 | 0.66M Na formate, 4.95% isopropanol, 0.825% PEG 3350, 0.1M Tris base pH 8.5 |
| PSS 33% #35 | 6.6% isopropanol, 4.95% PEG 3350, 0.2M (NH4)3 citrate/citric acid pH 7.5 |
| PSS 33% #36 | 9.9% isopropanol, 9.9% PEG 3350, 0.1M Tris pH 8.5 |
| PSS 33% #39 | 13.2% PEG 400, 4.95% PEG 1000, 0.15M K2H phosphate/NaH2 phosphate pH 6.5 |
| PSS 33% #41 | 8.25% PEG 400, 6.6% PEG 3350, 0.1M MgCl2, 0.1M Tris pH 8.5 |
| PSS 33% #42 | 9.9% PEG 1500, 0.99% MPD, 0.2M MgSO4, 0.1M acetate pH 5.5 |
| PSS 33% #44 | 9.9% PEG 1500, 6.6% PEG 400, 0.1M HEPES pH 7.5 |
| PSS 33% #48 | 8.25% PEG 3350, 4.95% MPD, 0.2M lithium sulfate, 0.1M imidazole pH 6.5 |
| PSS 67% #49 | 16.75% PEG 3350, 2.68% isopropanol, 0.1M CaCl2, 0.1M HEPES pH 7.5 |
| PSS 67% #50 | 6.6% PEG 8000, 3.3% PEG 400, 0.5M NaCl, 0.1M acetate pH 5.5 |
| PSS 67% #52 | 13.4% PEG 8000, 6.7% isopropanol, 0.2M ammonium sulfate, 0.1M HEPES pH 7.5 |
| PSS 67% #53 | 13.4% PEG 8000, 13.4% PEG 400, 0.1M MgCl2, 0.1M Tris pH 8.5 |
| PSS 67% #54 | 0.693M sodium formate, 8.25% PEG 3350, 0.1M CaCl2, 0.1M acetate pH 4.5 |
| PSS 33% #58 | 0.66M NaCl, 6.6% PEG 3350, 0.1M MgCl2, 0.1M imidazole pH 6.5 |
| PSS 33% #59 | 0.99M Na formate, 1.32% PEG 8000, 0.1M imidazole pH 6.5 |
| PSS 33% #61 | 3.3% PEG 3350, 0.462M K2H phosphate/NaH2 phosphate pH 7.5 |

Additional commercially available sparse matrix and random screens produced additional crystals or crystalline forms at 4° C.

| | |
|---|---|
| PSS 67% #11 | 5.36% MPD, 0.67M K2H phosphate/NaH2 phosphate pH 8.5 |
| PSS 67% #21 | 1.005M ammonium sulfate, 8.04% isopropanol, 0.1M imidazole pH 6.5 |
| PSS 67% #24 | 13.4% PEG 400, 0.536M K2H phosphate/NaH2 phosphate pH 7.5 |
| PSS 67% #28 | 20.1% MPD, 10.05% PEG 8000, 0.1M CaCl2, 0.1M acetate pH 5.5 |
| PSS 67% #29 | 20.1% MPD, 6.7% PEG 3350, 0.2M ammonium sulfate, 0.1M imidazole pH 6.5 |
| PSS 67%#35 | 13.4% isopropanol, 10.05% PEG 3350, 0.2M (NH4)3 citrate/citric acid pH 7.5 |
| PSS 67% #49 | 16.75% PEG 3350, 2.68% isopropanol, 0.1M CaCl2, 0.1M HEPES pH 7.5 |
| PSS 67% #51 | 13.4% PEG 8000, 2.01M MPD, 0.1M imidazole pH 6.5 |
| PSS 67% #52 | 13.4% PEG 8000, 6.7% isopropanol, 0.2M ammonium sulfate, 0.1M HEPES pH 7.5 |
| PSS 67% #61 | 6.7% PEG.3350, 0.938M K2H phosphate/NaH2 phosphate pH 7.5 |

These data are not an exhaustive presentation of crystallization data.

Example 2

Binding Assays

Binding affinity for a crystalline compound is measured by any assay known or available to those skilled in the art, including but not limited to BIAcore measurements, ELISA assays, competition assays, etc.

Bioactivity is measured in vivo or in vitro by any assay known or available to those skilled in the art. Exemplary assays include, but are not limited to, cell-based assays, i.e., megakaryocyte proliferation assays, 32D cell assays (an IL-3 dependent clone of murine 32D cells that have been transfected with human mpl receptor, described in greater detail in WO 95/26746), CD34+ assays, CD61 cell assays, etc. Bioactivity is also measured by various in vivo animal assays.

What is claimed is:

1. A crystal of a peptide produced under conditions selected from the group consisting of:
   (a) 0.1 M MES pH 6.S, 12% W/v PEG 20,000, pH 5.8-7.1
   (b) 1.6M ammonium sulfate, O.1 M MES pH 6.5, 10% v/v dioxane
   (c) 0.1 M sodium acetate pH 4.6, 2 M sodium formate, and
   (d) 0.1 M sodium HEPES pH 7.5, 0.8M sodium di-hydrogen phosphate, 0.8 M potassium di-hydrogen phosphate;

wherein the peptide has the sequence of SEQ ID NO: 46 or SEQ ID NO: 59.

2. The crystal of claim 1 wherein the peptide has the sequence of SEQ ID NO: 46, further including a vehicle.

3. The crystal of claim 2 wherein the vehicle is an immunoglobulin constant (Fc) domain.

4. The crystal of any one of claim 1, 2 or 3 further comprising a precipitant salt.

* * * * *

SEQUENCE LISTING

```
<160> NUMBER OF SEQ ID NOS: 114

<210> SEQ ID NO 1
<211> LENGTH: 227
<212> TYPE: PRT
<213> ORGANISM: Artificial sequence
<220> FEATURE:
<223> OTHER INFORMATION: Synthetic peptide

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 2
<211> LENGTH: 8
<212> TYPE: PRT
<213> ORGANISM: Artificial sequence
<220> FEATURE:
<223> OTHER INFORMATION: Synthetic peptide

<400> SEQUENCE: 2

Gly Gly Gly Lys Gly Gly Gly Gly
```

```
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Gly Gly Gly Asn Gly Ser Gly Gly
1               5

<210> SEQ ID NO 4
<211> LENGTH: 8
<212> TYPE: PRT
<213> ORGANISM: Artificial sequence
<220> FEATURE:
<223> OTHER INFORMATION: Synthetic peptide

<400> SEQUENCE: 4

Gly Gly Gly Cys Gly Gly Gly Gly
1               5

<210> SEQ ID NO 5
<211> LENGTH: 4
<212> TYPE: PRT
<213> ORGANISM: Artificial sequence
<220> FEATURE:
<223> OTHER INFORMATION: Synthetic peptide

<400> SEQUENCE: 5

Gly Pro Asn Gly
1

<210> SEQ ID NO 6
<211> LENGTH: 18
<212> TYPE: PRT
<213> ORGANISM: Artificial sequence
<220> FEATURE:
<223> OTHER INFORMATION: Synthetic peptide

<400> SEQUENCE: 6

Gly Ala Arg Glu Gly Pro Thr Leu Arg Gln Trp Leu Glu Trp Val Arg
1               5                   10                  15

Val Gly

<210> SEQ ID NO 7
<211> LENGTH: 18
<212> TYPE: PRT
<213> ORGANISM: Artificial sequence
<220> FEATURE:
<223> OTHER INFORMATION: Synthetic peptide

<400> SEQUENCE: 7

Arg Asp Leu Asp Gly Pro Thr Leu Arg Gln Trp Leu Pro Leu Pro Ser
1               5                   10                  15

Val Gln

<210> SEQ ID NO 8
<211> LENGTH: 18
<212> TYPE: PRT
<213> ORGANISM: Artificial sequence
<220> FEATURE:
<223> OTHER INFORMATION: Synthetic peptide
```

```
<400> SEQUENCE: 8

Ala Leu Arg Asp Gly Pro Thr Leu Lys Gln Trp Leu Glu Tyr Arg Arg
1               5                   10                  15

Gln Ala

<210> SEQ ID NO 9
<211> LENGTH: 18
<212> TYPE: PRT
<213> ORGANISM: Artificial sequence
<220> FEATURE:
<223> OTHER INFORMATION: Synthetic peptide

<400> SEQUENCE: 9

Ala Arg Gln Glu Gly Pro Thr Leu Lys Glu Trp Leu Phe Trp Val Arg
1               5                   10                  15

Met Gly

<210> SEQ ID NO 10
<211> LENGTH: 18
<212> TYPE: PRT
<213> ORGANISM: Artificial sequence
<220> FEATURE:
<223> OTHER INFORMATION: Synthetic peptide

<400> SEQUENCE: 10

Glu Ala Leu Leu Gly Pro Thr Leu Arg Glu Trp Leu Ala Trp Arg Arg
1               5                   10                  15

Ala Gln

<210> SEQ ID NO 11
<211> LENGTH: 18
<212> TYPE: PRT
<213> ORGANISM: Artificial sequence
<220> FEATURE:
<223> OTHER INFORMATION: Synthetic peptide

<400> SEQUENCE: 11

Met Ala Arg Asp Gly Pro Thr Leu Arg Glu Trp Leu Arg Thr Tyr Arg
1               5                   10                  15

Met Met

<210> SEQ ID NO 12
<211> LENGTH: 18
<212> TYPE: PRT
<213> ORGANISM: Artificial sequence
<220> FEATURE:
<223> OTHER INFORMATION: Synthetic peptide

<400> SEQUENCE: 12

Trp Met Pro Glu Gly Pro Thr Leu Lys Gln Trp Leu Phe His Gly Arg
1               5                   10                  15

Gly Gln

<210> SEQ ID NO 13
<211> LENGTH: 18
<212> TYPE: PRT
<213> ORGANISM: Artificial sequence
<220> FEATURE:
<223> OTHER INFORMATION: Synthetic peptide

<400> SEQUENCE: 13

His Ile Arg Glu Gly Pro Thr Leu Arg Gln Trp Leu Val Ala Leu Arg
1               5                   10                  15
```

Met Val

```
<210> SEQ ID NO 14
<211> LENGTH: 18
<212> TYPE: PRT
<213> ORGANISM: Artificial sequence
<220> FEATURE:
<223> OTHER INFORMATION: Synthetic peptide

<400> SEQUENCE: 14
```

Gln Leu Gly His Gly Pro Thr Leu Arg Gln Trp Leu Ser Trp Tyr Arg
1               5                   10                  15

Gly Met

```
<210> SEQ ID NO 15
<211> LENGTH: 18
<212> TYPE: PRT
<213> ORGANISM: Artificial sequence
<220> FEATURE:
<223> OTHER INFORMATION: Synthetic peptide

<400> SEQUENCE: 15
```

Glu Leu Arg Gln Gly Pro Thr Leu His Glu Trp Leu Gln His Leu Ala
1               5                   10                  15

Ser Lys

```
<210> SEQ ID NO 16
<211> LENGTH: 18
<212> TYPE: PRT
<213> ORGANISM: Artificial sequence
<220> FEATURE:
<223> OTHER INFORMATION: Synthetic peptide

<400> SEQUENCE: 16
```

Val Gly Ile Glu Gly Pro Thr Leu Arg Gln Trp Leu Ala Gln Arg Leu
1               5                   10                  15

Asn Pro

```
<210> SEQ ID NO 17
<211> LENGTH: 18
<212> TYPE: PRT
<213> ORGANISM: Artificial sequence
<220> FEATURE:
<223> OTHER INFORMATION: Synthetic peptide

<400> SEQUENCE: 17
```

Trp Ser Arg Asp Gly Pro Thr Leu Arg Glu Trp Leu Ala Trp Arg Ala
1               5                   10                  15

Val Gly

```
<210> SEQ ID NO 18
<211> LENGTH: 18
<212> TYPE: PRT
<213> ORGANISM: Artificial sequence
<220> FEATURE:
<223> OTHER INFORMATION: Synthetic peptide

<400> SEQUENCE: 18
```

Ala Val Pro Gln Gly Pro Thr Leu Lys Gln Trp Leu Leu Trp Arg Arg
1               5                   10                  15

Cys Ala

```
<210> SEQ ID NO 19
<211> LENGTH: 18
<212> TYPE: PRT
<213> ORGANISM: Artificial sequence
<220> FEATURE:
<223> OTHER INFORMATION: Synthetic peptide

<400> SEQUENCE: 19

Arg Ile Arg Glu Gly Pro Thr Leu Lys Glu Trp Leu Ala Gln Arg Arg
1               5                   10                  15

Gly Phe

<210> SEQ ID NO 20
<211> LENGTH: 18
<212> TYPE: PRT
<213> ORGANISM: Artificial sequence
<220> FEATURE:
<223> OTHER INFORMATION: Synthetic peptide

<400> SEQUENCE: 20

Arg Phe Ala Glu Gly Pro Thr Leu Arg Glu Trp Leu Glu Gln Arg Lys
1               5                   10                  15

Leu Val

<210> SEQ ID NO 21
<211> LENGTH: 18
<212> TYPE: PRT
<213> ORGANISM: Artificial sequence
<220> FEATURE:
<223> OTHER INFORMATION: Synthetic peptide

<400> SEQUENCE: 21

Asp Arg Phe Gln Gly Pro Thr Leu Arg Glu Trp Leu Ala Ala Ile Arg
1               5                   10                  15

Ser Val

<210> SEQ ID NO 22
<211> LENGTH: 18
<212> TYPE: PRT
<213> ORGANISM: Artificial sequence
<220> FEATURE:
<223> OTHER INFORMATION: Synthetic peptide

<400> SEQUENCE: 22

Ala Gly Arg Glu Gly Pro Thr Leu Arg Glu Trp Leu Asn Met Arg Val
1               5                   10                  15

Trp Gln

<210> SEQ ID NO 23
<211> LENGTH: 18
<212> TYPE: PRT
<213> ORGANISM: Artificial sequence
<220> FEATURE:
<223> OTHER INFORMATION: Synthetic peptide

<400> SEQUENCE: 23

Ala Leu Gln Glu Gly Pro Thr Leu Arg Gln Trp Leu Gly Trp Gly Gln
1               5                   10                  15

Trp Gly

<210> SEQ ID NO 24
<211> LENGTH: 18
<212> TYPE: PRT
<213> ORGANISM: Artificial sequence
```

<220> FEATURE:
<223> OTHER INFORMATION: Synthetic peptide

<400> SEQUENCE: 24

Tyr Cys Asp Glu Gly Pro Thr Leu Lys Gln Trp Leu Val Cys Leu Gly
1               5                   10                  15
Leu Gln

<210> SEQ ID NO 25
<211> LENGTH: 18
<212> TYPE: PRT
<213> ORGANISM: Artificial sequence
<220> FEATURE:
<223> OTHER INFORMATION: Synthetic peptide

<400> SEQUENCE: 25

Trp Cys Lys Glu Gly Pro Thr Leu Arg Glu Trp Leu Arg Trp Gly Phe
1               5                   10                  15
Leu Cys

<210> SEQ ID NO 26
<211> LENGTH: 18
<212> TYPE: PRT
<213> ORGANISM: Artificial sequence
<220> FEATURE:
<223> OTHER INFORMATION: Synthetic peptide

<400> SEQUENCE: 26

Cys Ser Ser Gly Gly Pro Thr Leu Arg Glu Trp Leu Gln Cys Arg Arg
1               5                   10                  15
Met Gln

<210> SEQ ID NO 27
<211> LENGTH: 18
<212> TYPE: PRT
<213> ORGANISM: Artificial sequence
<220> FEATURE:
<223> OTHER INFORMATION: Synthetic peptide

<400> SEQUENCE: 27

Cys Ser Trp Gly Gly Pro Thr Leu Lys Gln Trp Leu Gln Cys Val Arg
1               5                   10                  15
Ala Lys

<210> SEQ ID NO 28
<211> LENGTH: 18
<212> TYPE: PRT
<213> ORGANISM: Artificial sequence
<220> FEATURE:
<223> OTHER INFORMATION: Synthetic peptide

<400> SEQUENCE: 28

Cys Gln Leu Gly Gly Pro Thr Leu Arg Glu Trp Leu Ala Cys Arg Leu
1               5                   10                  15
Gly Ala

<210> SEQ ID NO 29
<211> LENGTH: 18
<212> TYPE: PRT
<213> ORGANISM: Artificial sequence
<220> FEATURE:
<223> OTHER INFORMATION: Synthetic peptide

<400> SEQUENCE: 29

Cys Trp Glu Gly Gly Pro Thr Leu Lys Glu Trp Leu Gln Cys Leu Val
1               5                   10                  15

Glu Arg

<210> SEQ ID NO 30
<211> LENGTH: 18
<212> TYPE: PRT
<213> ORGANISM: Artificial sequence
<220> FEATURE:
<223> OTHER INFORMATION: Synthetic peptide

<400> SEQUENCE: 30

Cys Arg Gly Gly Gly Pro Thr Leu His Gln Trp Leu Ser Cys Phe Arg
1               5                   10                  15

Trp Gln

<210> SEQ ID NO 31
<211> LENGTH: 18
<212> TYPE: PRT
<213> ORGANISM: Artificial sequence
<220> FEATURE:
<223> OTHER INFORMATION: Synthetic peptide

<400> SEQUENCE: 31

Cys Arg Asp Gly Gly Pro Thr Leu Arg Gln Trp Leu Ala Cys Leu Gln
1               5                   10                  15

Gln Lys

<210> SEQ ID NO 32
<211> LENGTH: 18
<212> TYPE: PRT
<213> ORGANISM: Artificial sequence
<220> FEATURE:
<223> OTHER INFORMATION: Synthetic peptide

<400> SEQUENCE: 32

Glu Leu Arg Ser Gly Pro Thr Leu Lys Glu Trp Leu Val Trp Arg Leu
1               5                   10                  15

Ala Gln

<210> SEQ ID NO 33
<211> LENGTH: 18
<212> TYPE: PRT
<213> ORGANISM: Artificial sequence
<220> FEATURE:
<223> OTHER INFORMATION: Synthetic peptide

<400> SEQUENCE: 33

Gly Cys Arg Ser Gly Pro Thr Leu Arg Glu Trp Leu Ala Cys Arg Glu
1               5                   10                  15

Val Gln

<210> SEQ ID NO 34
<211> LENGTH: 18
<212> TYPE: PRT
<213> ORGANISM: Artificial sequence
<220> FEATURE:
<223> OTHER INFORMATION: Synthetic peptide

<400> SEQUENCE: 34

Thr Cys Glu Gln Gly Pro Thr Leu Arg Gln Trp Leu Leu Cys Arg Gln
1               5                   10                  15

Gly Arg

<210> SEQ ID NO 35
<211> LENGTH: 32
<212> TYPE: PRT
<213> ORGANISM: Artificial sequence
<220> FEATURE:
<223> OTHER INFORMATION: Synthetic peptide

<400> SEQUENCE: 35

Ile Glu Gly Pro Thr Leu Arg Gln Trp Leu Ala Ala Arg Ala Gly Pro
1               5                   10                  15

Asn Gly Ile Glu Gly Pro Thr Leu Arg Gln Trp Leu Ala Ala Arg Ala
            20                  25                  30

<210> SEQ ID NO 36
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (9)..(31)
<223> OTHER INFORMATION: Cyclic peptide

<400> SEQUENCE: 36

Ile Glu Gly Pro Thr Leu Arg Gln Cys Leu Ala Ala Arg Ala Gly Gly
1               5                   10                  15

Gly Gly Gly Gly Gly Gly Ile Glu Gly Pro Thr Leu Arg Gln Cys Leu
            20                  25                  30

Ala Ala Arg Ala
            35

<210> SEQ ID NO 37
<211> LENGTH: 36
<212> TYPE: PRT
<213> ORGANISM: Artificial sequence
<220> FEATURE:
<223> OTHER INFORMATION: Synthetic peptide

<400> SEQUENCE: 37

Ile Glu Gly Pro Thr Leu Arg Gln Cys Leu Ala Ala Arg Ala Gly Gly
1               5                   10                  15

Gly Gly Gly Gly Gly Gly Ile Glu Gly Pro Thr Leu Arg Gln Cys Leu
            20                  25                  30

Ala Ala Arg Ala
            35

<210> SEQ ID NO 38
<211> LENGTH: 36
<212> TYPE: PRT
<213> ORGANISM: Artificial sequence
<220> FEATURE:
<223> OTHER INFORMATION: Synthetic peptide

<400> SEQUENCE: 38

Ile Glu Gly Pro Thr Leu Arg Gln Ala Leu Ala Ala Arg Ala Gly Gly
1               5                   10                  15

Gly Gly Gly Gly Gly Gly Ile Glu Gly Pro Thr Leu Arg Gln Ala Leu
            20                  25                  30

Ala Ala Arg Ala
            35

<210> SEQ ID NO 39
<211> LENGTH: 36
<212> TYPE: PRT
<213> ORGANISM: Artificial sequence
<220> FEATURE:
<223> OTHER INFORMATION: Synthetic peptide

<400> SEQUENCE: 39

Ile Glu Gly Pro Thr Leu Arg Gln Trp Leu Ala Ala Arg Ala Gly Gly
1               5                   10                  15

Gly Lys Gly Gly Gly Gly Ile Glu Gly Pro Thr Leu Arg Gln Trp Leu
            20                  25                  30

Ala Ala Arg Ala
        35

<210> SEQ ID NO 40
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (18)..(19)
<223> OTHER INFORMATION: Bromoacetyl is between residues 18 and 19

<400> SEQUENCE: 40

Ile Glu Gly Pro Thr Leu Arg Gln Trp Leu Ala Ala Arg Ala Gly Gly
1               5                   10                  15

Gly Lys Gly Gly Gly Gly Ile Glu Gly Pro Thr Leu Arg Gln Trp Leu
            20                  25                  30

Ala Ala Arg Ala
        35

<210> SEQ ID NO 41
<211> LENGTH: 36
<212> TYPE: PRT
<213> ORGANISM: Artificial sequence
<220> FEATURE:
<223> OTHER INFORMATION: Synthetic peptide

<400> SEQUENCE: 41

Ile Glu Gly Pro Thr Leu Arg Gln Trp Leu Ala Ala Arg Ala Gly Gly
1               5                   10                  15

Gly Cys Gly Gly Gly Gly Ile Glu Gly Pro Thr Leu Arg Gln Trp Leu
            20                  25                  30

Ala Ala Arg Ala
        35

<210> SEQ ID NO 42
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (18)..(19)
<223> OTHER INFORMATION: PEG is between residues 18 and 19

<400> SEQUENCE: 42

Ile Glu Gly Pro Thr Leu Arg Gln Trp Leu Ala Ala Arg Ala Gly Gly
1               5                   10                  15

Gly Lys Gly Gly Gly Gly Ile Glu Gly Pro Thr Leu Arg Gln Trp Leu

Ala Ala Arg Ala
        35

<210> SEQ ID NO 43
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (18)..(19)
<223> OTHER INFORMATION: PEG is between residues 18 and 19

<400> SEQUENCE: 43

Ile Glu Gly Pro Thr Leu Arg Gln Trp Leu Ala Ala Arg Ala Gly Gly
1               5                   10                  15

Gly Cys Gly Gly Gly Gly Ile Glu Gly Pro Thr Leu Arg Gln Trp Leu
            20                  25                  30

Ala Ala Arg Ala
        35

<210> SEQ ID NO 44
<211> LENGTH: 36
<212> TYPE: PRT
<213> ORGANISM: Artificial sequence
<220> FEATURE:
<223> OTHER INFORMATION: Synthetic peptide

<400> SEQUENCE: 44

Ile Glu Gly Pro Thr Leu Arg Gln Trp Leu Ala Ala Arg Ala Gly Gly
1               5                   10                  15

Gly Asn Gly Ser Gly Gly Ile Glu Gly Pro Thr Leu Arg Gln Trp Leu
            20                  25                  30

Ala Ala Arg Ala
        35

<210> SEQ ID NO 45
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (1)..(36)
<223> OTHER INFORMATION: Dimeric peptide

<400> SEQUENCE: 45

Ile Glu Gly Pro Thr Leu Arg Gln Trp Leu Ala Ala Arg Ala Gly Gly
1               5                   10                  15

Gly Cys Gly Gly Gly Gly Ile Glu Gly Pro Thr Leu Arg Gln Trp Leu
            20                  25                  30

Ala Ala Arg Ala
        35

<210> SEQ ID NO 46
<211> LENGTH: 36
<212> TYPE: PRT
<213> ORGANISM: Artificial sequence
<220> FEATURE:
<223> OTHER INFORMATION: Synthetic peptide

<400> SEQUENCE: 46

```
Ile Glu Gly Pro Thr Leu Arg Gln Trp Leu Ala Ala Arg Ala Gly Gly
1               5                   10                  15

Gly Gly Gly Gly Gly Ile Glu Gly Pro Thr Leu Arg Gln Trp Leu
            20                  25                  30

Ala Ala Arg Ala
        35

<210> SEQ ID NO 47
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 47

Ile Glu Gly Pro Thr Leu Arg Gln Trp Leu Ala Ala Arg Ala Gly Pro
1               5                   10                  15

Asn Gly Ile Glu Gly Pro Thr Leu Arg Gln Trp Leu Ala Ala Arg Ala
            20                  25                  30

<210> SEQ ID NO 48
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1
<220> FEATURE:
<221> NAME/KEY: Binding
<222> LOCATION: (32)..(32)
<223> OTHER INFORMATION: Fc is bound to residue 32

<400> SEQUENCE: 48

Ile Glu Gly Pro Thr Leu Arg Gln Trp Leu Ala Ala Arg Ala Gly Pro
1               5                   10                  15

Asn Gly Ile Glu Gly Pro Thr Leu Arg Gln Trp Leu Ala Ala Arg Ala
            20                  25                  30

<210> SEQ ID NO 49
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (36)..(36)
<223> OTHER INFORMATION: Fc is bound to residue 36

<400> SEQUENCE: 49

Ile Glu Gly Pro Thr Leu Arg Gln Trp Leu Ala Ala Arg Ala Gly Gly
1               5                   10                  15

Gly Gly Gly Gly Gly Gly Ile Glu Gly Pro Thr Leu Arg Gln Trp Leu
            20                  25                  30

Ala Ala Arg Ala
        35

<210> SEQ ID NO 50
```

```
<211> LENGTH: 34
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 50

Gly Gly Ile Glu Gly Pro Thr Leu Arg Gln Trp Leu Ala Ala Arg Ala
1               5                   10                  15
Gly Pro Asn Gly Ile Glu Gly Pro Thr Leu Arg Gln Trp Leu Ala Ala
            20                  25                  30
Arg Ala

<210> SEQ ID NO 51
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 51

Ile Glu Gly Pro Thr Leu Arg Gln Trp Leu Ala Ala Arg Ala Gly Gly
1               5                   10                  15
Gly Gly Gly Gly Gly Gly Ile Glu Gly Pro Thr Leu Arg Gln Trp Leu
            20                  25                  30
Ala Ala Arg Ala
            35

<210> SEQ ID NO 52
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1
<220> FEATURE:
<221> NAME/KEY: Misc_feature
<222> LOCATION: (9)..(31)
<223> OTHER INFORMATION: Cyclic peptide

<400> SEQUENCE: 52

Ile Glu Gly Pro Thr Leu Arg Gln Cys Leu Ala Ala Arg Ala Gly Gly
1               5                   10                  15
Gly Gly Gly Gly Gly Gly Ile Glu Gly Pro Thr Leu Arg Gln Cys Leu
            20                  25                  30
Ala Ala Arg Ala
            35

<210> SEQ ID NO 53
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: Binding
```

```
<222> LOCATION: (1)..(1)
<223> OTHER INFORMATION: Fc is bound to residue 1

<400> SEQUENCE: 53

Ile Glu Gly Pro Thr Leu Arg Gln Cys Leu Ala Ala Arg Ala Gly Gly
1               5                   10                  15
Gly Gly Gly Gly Gly Gly Ile Glu Gly Pro Thr Leu Arg Gln Cys Leu
            20                  25                  30
Ala Ala Arg Ala
        35

<210> SEQ ID NO 54
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 54

Ile Glu Gly Pro Thr Leu Arg Gln Ala Leu Ala Ala Arg Ala Gly Gly
1               5                   10                  15
Gly Gly Gly Gly Gly Gly Ile Glu Gly Pro Thr Leu Arg Gln Ala Leu
            20                  25                  30
Ala Ala Arg Ala
        35

<210> SEQ ID NO 55
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 55

Ile Glu Gly Pro Thr Leu Arg Gln Trp Leu Ala Ala Arg Ala Gly Gly
1               5                   10                  15
Gly Lys Gly Gly Gly Gly Ile Glu Gly Pro Thr Leu Arg Gln Trp Leu
            20                  25                  30
Ala Ala Arg Ala
        35

<210> SEQ ID NO 56
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 56

Ile Glu Gly Pro Thr Leu Arg Gln Trp Leu Ala Ala Arg Ala Gly Gly
1               5                   10                  15
Gly Cys Gly Gly Gly Gly Ile Glu Gly Pro Thr Leu Arg Gln Trp Leu
            20                  25                  30
```

```
Ala Ala Arg Ala
        35

<210> SEQ ID NO 57
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 57

Ile Glu Gly Pro Thr Leu Arg Gln Trp Leu Ala Ala Arg Ala Gly Gly
1               5                   10                  15

Gly Asn Gly Ser Gly Gly Ile Glu Gly Pro Thr Leu Arg Gln Trp Leu
            20                  25                  30

Ala Ala Arg Ala
        35

<210> SEQ ID NO 58
<211> LENGTH: 36
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1
<220> FEATURE:
<221> NAME/KEY: Misc_feature
<222> LOCATION: (1)..(36)
<223> OTHER INFORMATION: Dimeric peptide

<400> SEQUENCE: 58

Ile Glu Gly Pro Thr Leu Arg Gln Trp Leu Ala Ala Arg Ala Gly Gly
1               5                   10                  15

Gly Cys Gly Gly Gly Gly Ile Glu Gly Pro Thr Leu Arg Gln Trp Leu
            20                  25                  30

Ala Ala Arg Ala
        35

<210> SEQ ID NO 59
<211> LENGTH: 41
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 59

Gly Gly Gly Gly Gly Ile Glu Gly Pro Thr Leu Arg Gln Trp Leu Ala
1               5                   10                  15

Ala Arg Ala Gly Gly Gly Gly Gly Gly Gly Ile Glu Gly Pro Thr
            20                  25                  30

Leu Arg Gln Trp Leu Ala Ala Arg Ala
        35                  40

<210> SEQ ID NO 60
```

```
<211> LENGTH: 41
<212> TYPE: PRT
<213> ORGANISM: Artificial sequence
<220> FEATURE:
<223> OTHER INFORMATION: Synthetic peptide

<400> SEQUENCE: 60

Cys Ser Ser Gly Gly Pro Thr Leu Arg Glu Trp Leu Gln Cys Arg Arg
1               5                   10                  15

Met Gln Gly Gly Gly Gly Cys Ser Ser Gly Gly Pro Thr Leu Arg
            20                  25                  30

Glu Trp Leu Gln Cys Arg Arg Met Gln
        35                  40

<210> SEQ ID NO 61
<211> LENGTH: 44
<212> TYPE: PRT
<213> ORGANISM: Artificial sequence
<220> FEATURE:
<223> OTHER INFORMATION: Synthetic peptide

<400> SEQUENCE: 61

Gln Leu Gly His Gly Pro Thr Leu Arg Gln Trp Leu Ser Trp Tyr Arg
1               5                   10                  15

Gly Met Gly Gly Gly Lys Gly Gly Gly Ala Leu Arg Asp Gly Pro
            20                  25                  30

Thr Leu Lys Gln Trp Leu Glu Tyr Arg Arg Gln Ala
        35                  40

<210> SEQ ID NO 62
<211> LENGTH: 42
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (21)..(22)
<223> OTHER INFORMATION: PEG is between residues 21 and 22

<400> SEQUENCE: 62

Arg Phe Ala Glu Gly Pro Thr Leu Arg Glu Trp Leu Glu Gln Arg Lys
1               5                   10                  15

Leu Val Gly Gly Gly Gly Gly Arg Phe Ala Glu Gly Pro Thr Leu
            20                  25                  30

Arg Glu Trp Leu Glu Gln Arg Lys Leu Val
        35                  40

<210> SEQ ID NO 63
<211> LENGTH: 42
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (21)..(22)
<223> OTHER INFORMATION: PEG is between residues 21 and 22

<400> SEQUENCE: 63

His Ile Arg Glu Gly Pro Thr Leu Arg Gln Trp Leu Val Ala Leu Arg
1               5                   10                  15

Met Val Gly Gly Gly Gly Gly His Ile Arg Glu Gly Pro Thr Leu
            20                  25                  30
```

```
Arg Gln Trp Leu Val Ala Leu Arg Met Val
        35                  40

<210> SEQ ID NO 64
<211> LENGTH: 42
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1
<220> FEATURE:
<221> NAME/KEY: Binding
<222> LOCATION: (42)..(42)
<223> OTHER INFORMATION: Fc is bound to residue 42

<400> SEQUENCE: 64

Thr Cys Glu Gln Gly Pro Thr Leu Arg Gln Trp Leu Leu Cys Arg Gln
 1               5                  10                  15

Gly Arg Gly Gly Gly Lys Gly Gly Thr Cys Glu Gln Gly Pro Thr
            20                  25                  30

Leu Arg Gln Trp Leu Leu Cys Arg Gly Arg
        35                  40

<210> SEQ ID NO 65
<211> LENGTH: 39
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 65

Gln Leu Gly His Gly Pro Thr Leu Arg Gln Trp Leu Ser Trp Tyr Arg
 1               5                  10                  15

Gly Met Gly Pro Asn Gly Glu Leu Arg Ser Gly Pro Thr Leu Lys Glu
            20                  25                  30

Trp Leu Val Trp Arg Leu Ala
        35

<210> SEQ ID NO 66
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: Misc feature
<222> LOCATION: (1)..(18)
<223> OTHER INFORMATION: Dimeric peptide
<220> FEATURE:
<221> NAME/KEY: Binding
<222> LOCATION: (18)..(18)
<223> OTHER INFORMATION: Fc is bound to residue 18

<400> SEQUENCE: 66

Cys Ser Trp Gly Gly Pro Thr Leu Lys Gln Trp Leu Gln Cys Val Arg
 1               5                  10                  15

Ala Lys

<210> SEQ ID NO 67
<211> LENGTH: 25
```

```
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 67

Gly Gly Gly Lys Gly Gly Gly Ala Val Pro Gln Gly Pro Thr Leu Lys
1               5                   10                  15

Gln Trp Leu Leu Trp Arg Arg Cys Ala
            20                  25

<210> SEQ ID NO 68
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: PEG is bound to residue 1
<220> FEATURE:
<221> NAME/KEY: Misc_feature
<222> LOCATION: (1)..(18)
<223> OTHER INFORMATION: Dimeric peptide

<400> SEQUENCE: 68

Cys Ser Ser Gly Gly Pro Thr Leu Arg Glu Trp Leu Gln Cys Arg Arg
1               5                   10                  15

Met Gln

<210> SEQ ID NO 69
<211> LENGTH: 46
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 69

Gly Gly Gly Gly Gly Tyr Cys Asp Glu Gly Pro Thr Leu Lys Gln Trp
1               5                   10                  15

Leu Val Cys Leu Gly Leu Gln Gly Gly Gly Gly Tyr Cys Asp Glu
            20                  25                  30

Gly Pro Thr Leu Lys Gln Trp Leu Val Cys Leu Gly Leu Gln
        35                  40                  45

<210> SEQ ID NO 70
<211> LENGTH: 75
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (75)..(75)
<223> OTHER INFORMATION: Fc is bound to residue 75

<400> SEQUENCE: 70

Cys Ser Trp Gly Gly Pro Thr Leu Lys Gln Trp Leu Gln Cys Val Arg
1               5                   10                  15
```

Ala Lys Gly Gly Gly Ala Gly Gly Cys Ser Trp Gly Gly Pro Thr
            20                  25                  30

Leu Lys Gln Trp Leu Gln Cys Val Arg Ala Lys Gly Gly Gly Ala Gly
        35                  40                  45

Gly Gly Cys Ser Trp Gly Gly Pro Thr Leu Lys Gln Trp Leu Gln Cys
    50                  55                  60

Val Arg Ala Lys Gly Gly Gly Ala Gly Gly Gly
65                  70                  75

<210> SEQ ID NO 71
<211> LENGTH: 43
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (43)..(43)
<223> OTHER INFORMATION: PEG is bound to residue 43

<400> SEQUENCE: 71

Val Gly Ile Glu Gly Pro Thr Leu Arg Gln Trp Leu Ala Gln Arg Leu
1               5                   10                  15

Asn Pro Gly Gly Gly Cys Gly Gly Gly Val Gly Ile Glu Gly Pro Thr
            20                  25                  30

Leu Arg Gln Trp Leu Ala Gln Arg Leu Asn Pro
        35                  40

<210> SEQ ID NO 72
<211> LENGTH: 39
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 72

Glu Leu Arg Ser Gly Pro Thr Leu Lys Glu Trp Leu Val Trp Arg Leu
1               5                   10                  15

Ala Gly Gly Gly Gly Glu Leu Arg Ser Gly Pro Thr Leu Lys Glu Trp
            20                  25                  30

Leu Val Trp Arg Leu Ala Gln
        35

<210> SEQ ID NO 73
<211> LENGTH: 43
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1
<220> FEATURE:
<221> NAME/KEY: Binding
<222> LOCATION: (43)..(43)
<223> OTHER INFORMATION: Fc is bound to residue 43

<400> SEQUENCE: 73

Ala Leu Arg Asp Gly Pro Thr Leu Lys Gln Trp Leu Glu Tyr Arg Arg
1               5                   10                  15

Gln Ala Gly Gly Gly Lys Gly Gly Ala Leu Arg Asp Gly Pro Thr
            20                  25                  30

Leu Lys Gln Trp Leu Glu Tyr Arg Arg Gln Ala
        35                  40

<210> SEQ ID NO 74
<211> LENGTH: 36
<212> TYPE: PRT
<213> ORGANISM: Artificial sequence
<220> FEATURE:
<223> OTHER INFORMATION: Synthetic peptide

<400> SEQUENCE: 74

Ala Leu Arg Asp Gly Pro Thr Leu Lys Gln Trp Leu Glu Tyr Arg Arg
1               5                   10                  15

Gln Ala Ala Leu Arg Asp Gly Pro Thr Leu Lys Gln Trp Leu Glu Tyr
            20                  25                  30

Arg Arg Gln Ala
        35

<210> SEQ ID NO 75
<211> LENGTH: 36
<212> TYPE: PRT
<213> ORGANISM: Artificial sequence
<220> FEATURE:
<223> OTHER INFORMATION: Synthetic peptide

<400> SEQUENCE: 75

Glu Ala Leu Leu Gly Pro Thr Leu Arg Glu Trp Leu Ala Trp Arg Arg
1               5                   10                  15

Ala Gln Glu Ala Leu Leu Gly Pro Thr Leu Arg Glu Trp Leu Ala Trp
            20                  25                  30

Arg Arg Ala Gln
        35

<210> SEQ ID NO 76
<211> LENGTH: 36
<212> TYPE: PRT
<213> ORGANISM: Artificial sequence
<220> FEATURE:
<223> OTHER INFORMATION: Synthetic peptide

<400> SEQUENCE: 76

Ala Val Pro Gln Gly Pro Thr Leu Lys Gln Trp Leu Leu Trp Arg Arg
1               5                   10                  15

Cys Ala Ala Val Pro Gln Gly Pro Thr Leu Lys Gln Trp Leu Leu Trp
            20                  25                  30

Arg Arg Cys Ala
        35

<210> SEQ ID NO 77
<211> LENGTH: 36
<212> TYPE: PRT
<213> ORGANISM: Artificial sequence
<220> FEATURE:
<223> OTHER INFORMATION: Synthetic peptide

<400> SEQUENCE: 77

Tyr Cys Asp Glu Gly Pro Thr Leu Lys Gln Trp Leu Val Cys Leu Gly
1               5                   10                  15

Leu Gln Tyr Cys Asp Glu Gly Pro Thr Leu Lys Gln Trp Leu Val Cys
            20                  25                  30

Leu Gly Leu Gln
        35

<210> SEQ ID NO 78
<211> LENGTH: 36
<212> TYPE: PRT
<213> ORGANISM: Artificial sequence
<220> FEATURE:
<223> OTHER INFORMATION: Synthetic peptide

<400> SEQUENCE: 78

Cys Ser Ser Gly Gly Pro Thr Leu Arg Glu Trp Leu Gln Cys Arg Arg
1               5                   10                  15

Met Gln Cys Ser Ser Gly Gly Pro Thr Leu Arg Glu Trp Leu Gln Cys
            20                  25                  30

Arg Arg Met Gln
        35

<210> SEQ ID NO 79
<211> LENGTH: 36
<212> TYPE: PRT
<213> ORGANISM: Artificial sequence
<220> FEATURE:
<223> OTHER INFORMATION: Synthetic peptide

<400> SEQUENCE: 79

Cys Ser Trp Gly Gly Pro Thr Leu Lys Gln Trp Leu Gln Cys Val Arg
1               5                   10                  15

Ala Lys Cys Ser Trp Gly Gly Pro Thr Leu Lys Gln Trp Leu Gln Cys
            20                  25                  30

Val Arg Ala Lys
        35

<210> SEQ ID NO 80
<211> LENGTH: 41
<212> TYPE: PRT
<213> ORGANISM: Artificial sequence
<220> FEATURE:
<223> OTHER INFORMATION: Synthetic peptide

<400> SEQUENCE: 80

Ala Leu Arg Asp Gly Pro Thr Leu Lys Gln Trp Leu Glu Tyr Arg Arg
1               5                   10                  15

Gln Ala Gly Gly Gly Gly Ala Leu Arg Asp Gly Pro Thr Leu Lys
            20                  25                  30

Gln Trp Leu Glu Tyr Arg Arg Gln Ala
        35                  40

<210> SEQ ID NO 81
<211> LENGTH: 41
<212> TYPE: PRT
<213> ORGANISM: Artificial sequence
<220> FEATURE:
<223> OTHER INFORMATION: Synthetic peptide

<400> SEQUENCE: 81

Glu Ala Leu Leu Gly Pro Thr Leu Arg Glu Trp Leu Ala Trp Arg Arg
1               5                   10                  15

Ala Gln Gly Gly Gly Gly Gly Glu Ala Leu Leu Gly Pro Thr Leu Arg
            20                  25                  30

Glu Trp Leu Ala Trp Arg Arg Ala Gln
        35                  40

<210> SEQ ID NO 82
<211> LENGTH: 41
<212> TYPE: PRT
<213> ORGANISM: Artificial sequence
<220> FEATURE:
<223> OTHER INFORMATION: Synthetic peptide

<400> SEQUENCE: 82

Ala Val Pro Gln Gly Pro Thr Leu Lys Gln Trp Leu Leu Trp Arg Arg
1               5                   10                  15

Cys Ala Gly Gly Gly Gly Gly Ala Val Pro Gln Gly Pro Thr Leu Lys
                20                  25                  30

Gln Trp Leu Leu Trp Arg Arg Cys Ala
            35                  40

<210> SEQ ID NO 83
<211> LENGTH: 41
<212> TYPE: PRT
<213> ORGANISM: Artificial sequence
<220> FEATURE:
<223> OTHER INFORMATION: Synthetic peptide

<400> SEQUENCE: 83

Tyr Cys Asp Glu Gly Pro Thr Leu Lys Gln Trp Leu Val Cys Leu Gly
1               5                   10                  15

Leu Gln Gly Gly Gly Gly Gly Tyr Cys Asp Glu Gly Pro Thr Leu Lys
                20                  25                  30

Gln Trp Leu Val Cys Leu Gly Leu Gln
            35                  40

<210> SEQ ID NO 84
<211> LENGTH: 41
<212> TYPE: PRT
<213> ORGANISM: Artificial sequence
<220> FEATURE:
<223> OTHER INFORMATION: Synthetic peptide

<400> SEQUENCE: 84

Cys Ser Ser Gly Gly Pro Thr Leu Arg Glu Trp Leu Gln Cys Arg Arg
1               5                   10                  15

Met Gln Gly Gly Gly Gly Gly Cys Ser Ser Gly Gly Pro Thr Leu Arg
                20                  25                  30

Glu Trp Leu Gln Cys Arg Arg Met Gln
            35                  40

<210> SEQ ID NO 85
<211> LENGTH: 41
<212> TYPE: PRT
<213> ORGANISM: Artificial sequence
<220> FEATURE:
<223> OTHER INFORMATION: Synthetic peptide

<400> SEQUENCE: 85

Cys Ser Trp Gly Gly Pro Thr Leu Lys Gln Trp Leu Gln Cys Val Arg
1               5                   10                  15

Ala Lys Gly Gly Gly Gly Gly Cys Ser Trp Gly Gly Pro Thr Leu Lys
                20                  25                  30

Gln Trp Leu Gln Cys Val Arg Ala Lys
            35                  40

<210> SEQ ID NO 86

```
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 86

Gly Gly Gly Gly Gly Ala Leu Arg Asp Gly Pro Thr Leu Lys Gln Trp
1               5                   10                  15

Leu Glu Tyr Arg Arg Gln Ala
            20

<210> SEQ ID NO 87
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 87

Gly Gly Gly Gly Gly Glu Ala Leu Leu Gly Pro Thr Leu Arg Glu Trp
1               5                   10                  15

Leu Ala Trp Arg Arg Ala Gln
            20

<210> SEQ ID NO 88
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 88

Gly Gly Gly Gly Gly Ala Val Pro Gln Gly Pro Thr Leu Lys Gln Trp
1               5                   10                  15

Leu Leu Trp Arg Arg Cys Ala
            20

<210> SEQ ID NO 89
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 89

Gly Gly Gly Gly Gly Tyr Cys Asp Glu Gly Pro Thr Leu Lys Gln Trp
1               5                   10                  15

Leu Val Cys Leu Gly Leu Gln
            20
```

```
<210> SEQ ID NO 90
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 90

Gly Gly Gly Gly Gly Cys Ser Ser Gly Gly Pro Thr Leu Arg Glu Trp
1               5                   10                  15

Leu Gln Cys Arg Arg Met Gln
            20

<210> SEQ ID NO 91
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 91

Gly Gly Gly Gly Gly Cys Ser Trp Gly Gly Pro Thr Leu Lys Gln Trp
1               5                   10                  15

Leu Gln Cys Val Arg Ala Lys
            20

<210> SEQ ID NO 92
<211> LENGTH: 46
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 92

Gly Gly Gly Gly Gly Ala Leu Arg Asp Gly Pro Thr Leu Lys Gln Trp
1               5                   10                  15

Leu Glu Tyr Arg Arg Gln Ala Gly Gly Gly Gly Ala Leu Arg Asp
            20                  25                  30

Gly Pro Thr Leu Lys Gln Trp Leu Glu Tyr Arg Arg Gln Ala
        35                  40                  45

<210> SEQ ID NO 93
<211> LENGTH: 46
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 93

Gly Gly Gly Gly Gly Glu Ala Leu Leu Gly Pro Thr Leu Arg Glu Trp
1               5                   10                  15
```

Leu Ala Trp Arg Arg Ala Gln Gly Gly Gly Gly Glu Ala Leu Leu
            20                  25                  30

Gly Pro Thr Leu Arg Glu Trp Leu Ala Trp Arg Arg Ala Gln
        35                  40                  45

<210> SEQ ID NO 94
<211> LENGTH: 46
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 94

Gly Gly Gly Gly Gly Ala Val Pro Gln Gly Pro Thr Leu Lys Gln Trp
1               5                   10                  15

Leu Leu Trp Arg Arg Cys Ala Gly Gly Gly Gly Ala Val Pro Gln
            20                  25                  30

Gly Pro Thr Leu Lys Gln Trp Leu Leu Trp Arg Arg Cys Ala
        35                  40                  45

<210> SEQ ID NO 95
<211> LENGTH: 46
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 95

Gly Gly Gly Gly Gly Tyr Cys Asp Glu Gly Pro Thr Leu Lys Gln Trp
1               5                   10                  15

Leu Val Cys Leu Gly Leu Gln Gly Gly Gly Gly Tyr Cys Asp Glu
            20                  25                  30

Gly Pro Thr Leu Lys Gln Trp Leu Val Cys Leu Gly Leu Gln
        35                  40                  45

<210> SEQ ID NO 96
<211> LENGTH: 46
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 96

Gly Gly Gly Gly Gly Cys Ser Ser Gly Gly Pro Thr Leu Arg Glu Trp
1               5                   10                  15

Leu Gln Cys Arg Arg Met Gln Gly Gly Gly Gly Cys Ser Ser Gly
            20                  25                  30

Gly Pro Thr Leu Arg Glu Trp Leu Gln Cys Arg Arg Met Gln
        35                  40                  45

<210> SEQ ID NO 97
<211> LENGTH: 46
<212> TYPE: PRT

<213> ORGANISM: Artificial sequence
<220> FEATURE:
<223> OTHER INFORMATION: Synthetic peptide
<220> FEATURE:
<221> NAME/KEY: Binding
<222> LOCATION: (1)..(1)
<223> OTHER INFORMATION: Fc is bound to residue 1

<400> SEQUENCE: 97

Gly Gly Gly Gly Gly Cys Ser Trp Gly Gly Pro Thr Leu Lys Gln Trp
1               5                   10                  15

Leu Gln Cys Val Arg Ala Lys Gly Gly Gly Gly Cys Ser Trp Gly
            20                  25                  30

Gly Pro Thr Leu Lys Gln Trp Leu Gln Cys Val Arg Ala Lys
        35                  40                  45

<210> SEQ ID NO 98
<211> LENGTH: 46
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (46)..(46)
<223> OTHER INFORMATION: Fc is bound to residue 46

<400> SEQUENCE: 98

Ala Leu Arg Asp Gly Pro Thr Leu Lys Gln Trp Leu Glu Tyr Arg Arg
1               5                   10                  15

Gln Ala Gly Gly Gly Gly Gly Ala Leu Arg Asp Gly Pro Thr Leu Lys
            20                  25                  30

Gln Trp Leu Glu Tyr Arg Arg Gln Ala Gly Gly Gly Gly Gly
        35                  40                  45

<210> SEQ ID NO 99
<211> LENGTH: 46
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (46)..(46)
<223> OTHER INFORMATION: Fc is bound to residue 46

<400> SEQUENCE: 99

Glu Ala Leu Leu Gly Pro Thr Leu Arg Glu Trp Leu Ala Trp Arg Arg
1               5                   10                  15

Ala Gln Gly Gly Gly Gly Gly Glu Ala Leu Leu Gly Pro Thr Leu Arg
            20                  25                  30

Glu Trp Leu Ala Trp Arg Arg Ala Gln Gly Gly Gly Gly
        35                  40                  45

<210> SEQ ID NO 100
<211> LENGTH: 46
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (46)..(46)
<223> OTHER INFORMATION: Fc is bound to residue 46

<400> SEQUENCE: 100

```
Ala Val Pro Gln Gly Pro Thr Leu Lys Gln Trp Leu Leu Trp Arg Arg
1               5                   10                  15

Cys Ala Gly Gly Gly Gly Gly Ala Val Pro Gln Gly Pro Thr Leu Lys
            20                  25                  30

Gln Trp Leu Leu Trp Arg Arg Cys Ala Gly Gly Gly Gly Gly
        35                  40                  45
```

<210> SEQ ID NO 101
<211> LENGTH: 46
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (46)..(46)
<223> OTHER INFORMATION: Fc is bound to residue 46

<400> SEQUENCE: 101

```
Tyr Cys Asp Glu Gly Pro Thr Leu Lys Gln Trp Leu Val Cys Leu Gly
1               5                   10                  15

Leu Gln Gly Gly Gly Gly Gly Tyr Cys Asp Glu Gly Pro Thr Leu Lys
            20                  25                  30

Gln Trp Leu Val Cys Leu Gly Leu Gln Gly Gly Gly Gly Gly
        35                  40                  45
```

<210> SEQ ID NO 102
<211> LENGTH: 46
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (46)..(46)
<223> OTHER INFORMATION: Fc is bound to residue 46

<400> SEQUENCE: 102

```
Cys Ser Ser Gly Gly Pro Thr Leu Arg Glu Trp Leu Gln Cys Arg Arg
1               5                   10                  15

Met Gln Gly Gly Gly Gly Gly Cys Ser Ser Gly Gly Pro Thr Leu Arg
            20                  25                  30

Glu Trp Leu Gln Cys Arg Arg Met Gln Gly Gly Gly Gly Gly
        35                  40                  45
```

<210> SEQ ID NO 103
<211> LENGTH: 46
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (46)..(46)
<223> OTHER INFORMATION: Fc is bound to residue 46

<400> SEQUENCE: 103

```
Cys Ser Trp Gly Gly Pro Thr Leu Lys Gln Trp Leu Gln Cys Val Arg
1               5                   10                  15

Ala Lys Gly Gly Gly Gly Gly Cys Ser Trp Gly Gly Pro Thr Leu Lys
            20                  25                  30

Gln Trp Leu Gln Cys Val Arg Ala Lys Gly Gly Gly Gly Gly
        35                  40                  45
```

```
<210> SEQ ID NO 104
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (23)..(23)
<223> OTHER INFORMATION: Fc is bound to residue 23

<400> SEQUENCE: 104

Ala Leu Arg Asp Gly Pro Thr Leu Lys Gln Trp Leu Glu Tyr Arg Arg
1               5                   10                  15

Gln Ala Gly Gly Gly Gly Gly
            20

<210> SEQ ID NO 105
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (23)..(23)
<223> OTHER INFORMATION: Fc is bound to residue 23

<400> SEQUENCE: 105

Glu Ala Leu Leu Gly Pro Thr Leu Arg Glu Trp Leu Ala Trp Arg Arg
1               5                   10                  15

Ala Gln Gly Gly Gly Gly Gly
            20

<210> SEQ ID NO 106
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (23)..(23)
<223> OTHER INFORMATION: Fc is bound to residue 23

<400> SEQUENCE: 106

Ala Val Pro Gln Gly Pro Thr Leu Lys Gln Trp Leu Leu Trp Arg Arg
1               5                   10                  15

Cys Ala Gly Gly Gly Gly Gly
            20

<210> SEQ ID NO 107
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (23)..(23)
<223> OTHER INFORMATION: Fc is bound to residue 23

<400> SEQUENCE: 107

Tyr Cys Asp Glu Gly Pro Thr Leu Lys Gln Trp Leu Val Cys Leu Gly
1               5                   10                  15

Leu Gln Gly Gly Gly Gly Gly
            20
```

<210> SEQ ID NO 108
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (23)..(23)
<223> OTHER INFORMATION: Fc is bound to residue 23

<400> SEQUENCE: 108

Cys Ser Ser Gly Gly Pro Thr Leu Arg Glu Trp Leu Gln Cys Arg Arg
1               5                   10                  15

Met Gln Gly Gly Gly Gly Gly
            20

<210> SEQ ID NO 109
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: Binding
<222> LOCATION: (23)..(23)
<223> OTHER INFORMATION: Fc is bound to residue 23

<400> SEQUENCE: 109

Cys Ser Trp Gly Gly Pro Thr Leu Lys Gln Trp Leu Gln Cys Val Arg
1               5                   10                  15

Ala Lys Gly Gly Gly Gly Gly
            20

<210> SEQ ID NO 110
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (1)..(1)
<223> OTHER INFORMATION: Xaa=Glu, Asp, Lys, or Val
<220> FEATURE:
<221> NAME/KEY: Misc_feature
<222> LOCATION: (2)..(2)
<223> OTHER INFORMATION: Xaa=Gly or Ala
<220> FEATURE:
<221> NAME/KEY: Misc_feature
<222> LOCATION: (4)..(4)
<223> OTHER INFORMATION: Xaa=Thr or Ser
<220> FEATURE:
<221> NAME/KEY: Misc_feature
<222> LOCATION: (5)..(5)
<223> OTHER INFORMATION: Xaa=Leu, Ile, Val, Ala, or Phe
<220> FEATURE:
<221> NAME/KEY: Misc_feature
<222> LOCATION: (6)..(6)
<223> OTHER INFORMATION: Xaa=Arg or Lys
<220> FEATURE:
<221> NAME/KEY: Misc_feature
<222> LOCATION: (7)..(7)
<223> OTHER INFORMATION: Xaa=Gln, Asn, or Glu
<220> FEATURE:
<221> NAME/KEY: Misc_feature
<222> LOCATION: (8)..(8)
<223> OTHER INFORMATION: Xaa=Trp, Tyr, Phe, Cys, or Ala
<220> FEATURE:
<221> NAME/KEY: Misc_feature
<222> LOCATION: (9)..(9)
<223> OTHER INFORMATION: Xaa=Leu, Ile, Val, Ala, Phe, Met, or Lys

<400> SEQUENCE: 110

Xaa Xaa Pro Xaa Xaa Xaa Xaa Xaa Xaa
1               5

<210> SEQ ID NO 111
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (1)..(1)
<223> OTHER INFORMATION: Xaa=Ala, Val, Trp, Met, Gly, Tyr, Cys, Gln,
      Arg, or His
<220> FEATURE:
<221> NAME/KEY: Misc_feature
<222> LOCATION: (2)..(2)
<223> OTHER INFORMATION: Xaa=Ala, Val, Leu, Ile, Gly, Ser, or Cys
<220> FEATURE:
<221> NAME/KEY: Misc_feature
<222> LOCATION: (3)..(3)
<223> OTHER INFORMATION: Xaa=Leu, Ile, Pro, Trp, Gly, Ser, Asp, Lys, or
      Arg
<220> FEATURE:
<221> NAME/KEY: Misc_feature
<222> LOCATION: (4)..(4)
<223> OTHER INFORMATION: Xaa=Leu, Gly, Gln, Asp, Glu, or His
<220> FEATURE:
<221> NAME/KEY: Misc_feature
<222> LOCATION: (9)..(9)
<223> OTHER INFORMATION: Xaa=Lys or Arg
<220> FEATURE:
<221> NAME/KEY: Misc_feature
<222> LOCATION: (10)..(10)
<223> OTHER INFORMATION: Xaa=Gln or Glu
<220> FEATURE:
<221> NAME/KEY: Misc_feature
<222> LOCATION: (13)..(13)
<223> OTHER INFORMATION: Xaa=Ala, Val, Leu, Ser, Gln, Glu, or Arg
<220> FEATURE:
<221> NAME/KEY: Misc_feature
<222> LOCATION: (14)..(14)
<223> OTHER INFORMATION: Xaa=Ala, Trp, Thr, Tyr, Cys, Gln
<220> FEATURE:
<221> NAME/KEY: Misc_feature
<222> LOCATION: (15)..(15)
<223> OTHER INFORMATION: Xaa=Val, Leu, Gly, Tyr, or Arg
<220> FEATURE:
<221> NAME/KEY: Misc_feature
<222> LOCATION: (16)..(16)
<223> OTHER INFORMATION: Xaa=Ala, Leu, Phe, Gly, or Arg
<220> FEATURE:
<221> NAME/KEY: Misc_feature
<222> LOCATION: (17)..(17)
<223> OTHER INFORMATION: Xaa=Ala, Val, Leu, Met, Gly, Cys, Gln, or Asn
<220> FEATURE:
<221> NAME/KEY: Misc_feature
<222> LOCATION: (18)..(18)
<223> OTHER INFORMATION: Xaa=Ala, Val, Pro, Met, Phe, Gly, Cys, Gln, or
      Lys

<400> SEQUENCE: 111

Xaa Xaa Xaa Xaa Gly Pro Thr Leu Xaa Xaa Trp Leu Xaa Xaa Xaa Xaa
1               5                   10                  15

Xaa Xaa

<210> SEQ ID NO 112
<211> LENGTH: 18
<212> TYPE: PRT
<213> ORGANISM: Artificial sequence
<220> FEATURE:
<223> OTHER INFORMATION: Synthetic peptide

```
<220> FEATURE:
<221> NAME/KEY: Misc_feature
<222> LOCATION: (1)..(1)
<223> OTHER INFORMATION: Xaa=Ala, Val, Trp, Met, Gly, Tyr, Cys, Gln,
      Glu, Arg, or His
<220> FEATURE:
<221> NAME/KEY: Misc_feature
<222> LOCATION: (2)..(2)
<223> OTHER INFORMATION: Xaa=Ala, Val, Leu, Ile, Gly, Ser, or Cys
<220> FEATURE:
<221> NAME/KEY: Misc_feature
<222> LOCATION: (13)..(13)
<223> OTHER INFORMATION: Xaa=Ala, Val, Leu, Ser, Gln, Glu, or Arg
<220> FEATURE:
<221> NAME/KEY: Misc_feature
<222> LOCATION: (17)..(17)
<223> OTHER INFORMATION: Xaa=Ala, Val, Leu, Met, Gly, Cys, Gln, or Asn
<220> FEATURE:
<221> NAME/KEY: Misc_feature
<222> LOCATION: (18)..(18)
<223> OTHER INFORMATION: Xaa=Ala, Val, Pro, Met, Phe, Gly, Cys, Gln, or
      Lys

<400> SEQUENCE: 112

Xaa Xaa Arg Glu Gly Pro Thr Leu Arg Gln Trp Leu Xaa Trp Arg Arg
1               5                   10                  15

Xaa Xaa

<210> SEQ ID NO 113
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa=Glu, Asp, Lys, or Val
<220> FEATURE:
<221> NAME/KEY: MISC_FEATURE
<222> LOCATION: (3)..(3)
<223> OTHER INFORMATION: Xaa=Gly or Ala
<220> FEATURE:
<221> NAME/KEY: MISC_FEATURE
<222> LOCATION: (4)..(4)
<223> OTHER INFORMATION: Xaa=Pro
<220> FEATURE:
<221> NAME/KEY: MISC_FEATURE
<222> LOCATION: (5)..(5)
<223> OTHER INFORMATION: Xaa=Thr or Ser
<220> FEATURE:
<221> NAME/KEY: MISC_FEATURE
<222> LOCATION: (6)..(6)
<223> OTHER INFORMATION: Xaa=Leu, Ile, Val, Ala or Phe
<220> FEATURE:
<221> NAME/KEY: MISC_FEATURE
<222> LOCATION: (7)..(7)
<223> OTHER INFORMATION: Xaa=Arg or Lys
<220> FEATURE:
<221> NAME/KEY: MISC_FEATURE
<222> LOCATION: (8)..(8)
<223> OTHER INFORMATION: Xaa=Gln, Asn or Glu
<220> FEATURE:
<221> NAME/KEY: MISC_FEATURE
<222> LOCATION: (9)..(9)
<223> OTHER INFORMATION: Xaa=Trp, Tyr, Phe, Cys or Ala
<220> FEATURE:
<221> NAME/KEY: MISC_FEATURE
<222> LOCATION: (10)..(10)
<223> OTHER INFORMATION: Xaa=Leu, Ile, Val, Ala, Phe, Met or Lys

<400> SEQUENCE: 113
```

```
Xaa Xaa Xaa Xaa Xaa Xaa Xaa Xaa Xaa
1               5

<210> SEQ ID NO 114
<211> LENGTH: 20
<212> TYPE: PRT
<213> ORGANISM: Artificial sequence
<220> FEATURE:
<223> OTHER INFORMATION: Synthetic peptide

<400> SEQUENCE: 114

Gly Gly Gly Gly Gly Gly Gly Gly Gly Gly Gly Gly Gly Gly Gly
1               5                   10                  15

Gly Gly Gly Gly
            20
```